United States Patent
Chang et al.

(10) Patent No.: US 11,203,614 B2
(45) Date of Patent: Dec. 21, 2021

(54) COMPOSITE POLYPEPTIDE HAVING A METAL BINDING MOTIF AND MOLECULAR CONSTRUCT COMPRISING THE SAME

(71) Applicant: Immunwork Inc., Taipei (TW)

(72) Inventors: Tse-Wen Chang, Taipei (TW);
Hsing-Mao Chu, Taipei (TW);
Wei-Ting Tian, Taipei (TW);
Yueh-Hsiang Yu, Taipei (TW)

(73) Assignee: IMMUNWORK INC., Taipei (TW)

( * ) Notice: Subject to any disclaimer, the term of this patent is extended or adjusted under 35 U.S.C. 154(b) by 0 days.

(21) Appl. No.: 16/830,249

(22) Filed: Mar. 25, 2020

(65) Prior Publication Data

US 2020/0308223 A1    Oct. 1, 2020

Related U.S. Application Data

(60) Provisional application No. 62/823,626, filed on Mar. 25, 2019.

(51) Int. Cl.
*A61K 47/65*    (2017.01)
*C07K 7/06*    (2006.01)

(52) U.S. Cl.
CPC ............ *C07K 7/06* (2013.01); *C07K 2319/00* (2013.01)

(58) Field of Classification Search
CPC .... A61K 47/542; A61K 47/547; A61K 47/65; A61K 47/6849; A61K 47/6887; A61K 51/1027; C07K 16/2803; C07K 16/2887; C07K 16/2896; C07K 2317/35; C07K 2317/40; C07K 2317/526; C07K 2317/64; C07K 2319/00; C07K 2319/30; C07K 7/06
See application file for complete search history.

(56) References Cited

U.S. PATENT DOCUMENTS 7,745,391 B2 *    6/2010    Mintz ................... A61P 31/00
514/19.3

OTHER PUBLICATIONS

UniProt F8WSR3, pp. 1-5. Integrated into UniProtKB/TrEMBL Oct. 19, 2011. (Year: 2011).*
UniProt A0A3M1Q1M2, pp. 1-3. Integrated into UniProtKB/TrEMBL Feb. 13, 2019. (Year: 2019).*
UniProt A0A5K0XR00, pp. 1-3. Integrated into UniProtKB/TrEMBL Dec. 11, 2019. (Year: 2019).*
UniProt A0A392SZH1, pp. 1-3. Integrated into UniProtKB/TrEMBL Dec. 5, 2018. (Year: 2018).*
UniProt A0A317NL79, pp. 1-3. Integrated into UniProtKB/TrEMBL Oct. 10, 2018. (Year: 2018).*
UniProt A0A0G2ZNQ5, pp. 1-3. Integrated into UniProtKB/TrEMBL Sep. 16, 2015. (Year: 2015).*
UniProt F3FYF6, pp. 1-4. Integrated into UniProtKB/TrEMBL Jun. 28, 2011. (Year: 2011).*
UniProt A0A061JGC3, pp. 1-3. Integrated into UniProtKB/TrEMBL Sep. 3, 2014. (Year: 2014).*

* cited by examiner

*Primary Examiner* — Julie Ha

(57) ABSTRACT

Disclosed herein are composite polypeptide. According to various embodiments, the composite polypeptide includes a parent polypeptide and a metal binding motif capable of forming a complex with a metal cation. The composite polypeptide may be conjugated with a linker unit having a plurality of functional elements to form a multi-functional molecular construct. Alternatively, multiple composite polypeptides may be conjugated to a linker unit to form a molecular construct, or a polypeptide bundle. Linker units suitable for conjugating with the composite polypeptide having the metal binding motif are also disclosed.

11 Claims, 37 Drawing Sheets
Specification includes a Sequence Listing.

SDS-PAGE

Western blot

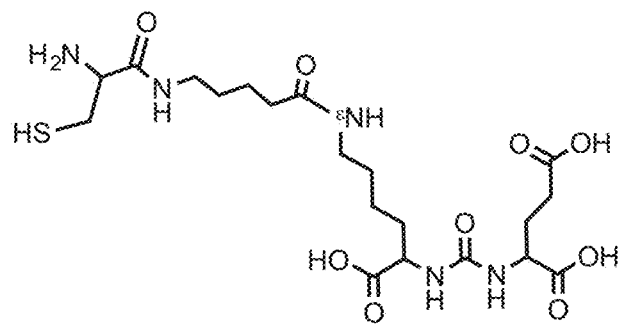
FIG. 37
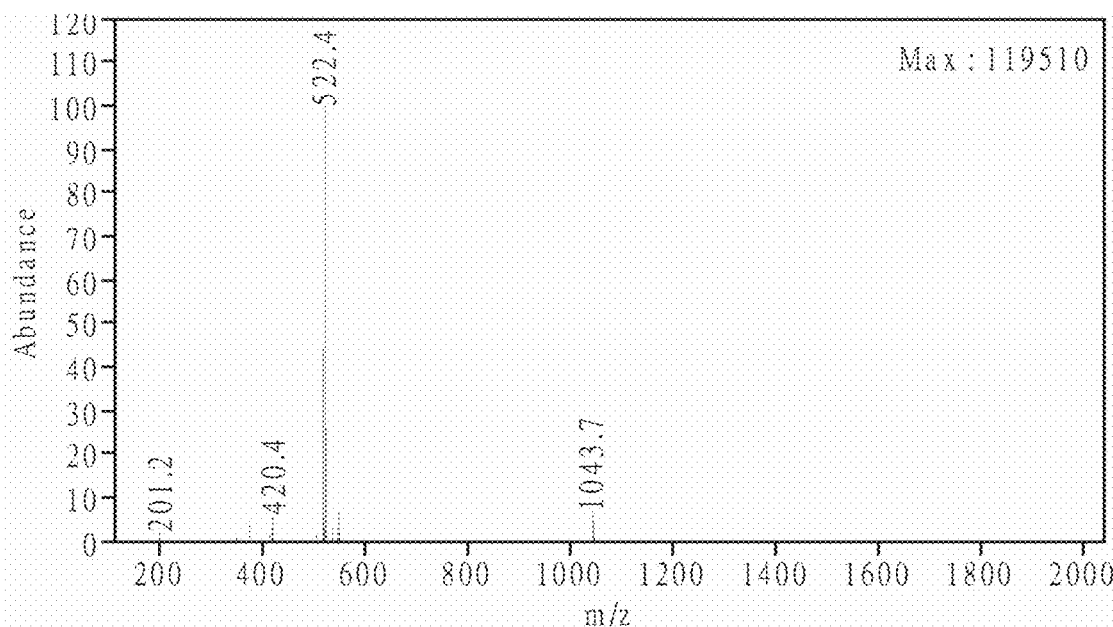
FIG. 38
CSNLSTCVLGKLSQELHKLQTYPRTNTGSGTP-(GGGS)₂-ACPGHA
SEQ ID No. 39
FIG. 39

SEQ ID No. 44

KGAGGKGAGGKG (SEQ ID No. 45)
EGEGEAGKGAG (SEQ ID NO: 46)

SEQUENCE LISTING

```
<160> NUMBER OF SEQ ID NOS: 47

<210> SEQ ID NO 1
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 2
<223> OTHER INFORMATION: Gly or Pro
<220> FEATURE:
<221> NAME/KEY: VARIANT
<222> LOCATION: 3
<223> OTHER INFORMATION: Gly or Ala

<400> SEQUENCE: 1

Cys Xaa Xaa His Ala
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Cys Gly Gly His Ala
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Cys Pro Gly His Ala
1               5

<210> SEQ ID NO 4
<211> LENGTH: 5
<212> TYPE: PRT
<213> ORGANISM: Artificial Sequence
<220> FEATURE:
```

```
<223> OTHER INFORMATION: Synthetic

<400> SEQUENCE: 4

Cys Gly Ala His Ala
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic

<400> SEQUENCE: 5

Cys Pro Ala His Ala
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

Gly Cys Gly Gly His Ala
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic

<400> SEQUENCE: 7

Ala Cys Pro Gly His Ala
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Gly Cys Pro Gly His Ala
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic

<400> SEQUENCE: 9

Gly Gly Gly Gly
1

<210> SEQ ID NO 10
<211> LENGTH: 18
<212> TYPE: PRT
<213> ORGANISM: Artificial Sequence
<220> FEATURE:
<223> OTHER INFORMATION: Synthetic
```

```
<400> SEQUENCE: 10

Gly Ser Thr Ser Gly Ser Gly Lys Pro Gly Ser Gly Glu Gly Ser Thr
1               5                   10                  15

Lys Gly

<210> SEQ ID NO 11
<211> LENGTH: 19
<212> TYPE: PRT
<213> ORGANISM: Artificial Sequence
<220> FEATURE:
<223> OTHER INFORMATION: Synthetic

<400> SEQUENCE: 11

Gly Gly Ser Gly Gly Ser Lys Gly Ser Lys Gly Ser Lys Gly Ser Lys
1               5                   10                  15

Gly Ser Lys

<210> SEQ ID NO 12
<211> LENGTH: 24
<212> TYPE: PRT
<213> ORGANISM: Artificial Sequence
<220> FEATURE:
<223> OTHER INFORMATION: Synthetic

<400> SEQUENCE: 12

Gly Gly Ser Gly Gly Ser Gly Lys Gly Gly Ser Gly Gly Ser Gly Lys
1               5                   10                  15

Gly Gly Ser Gly Gly Ser Gly Lys
            20

<210> SEQ ID NO 13
<211> LENGTH: 483
<212> TYPE: PRT
<213> ORGANISM: Artificial Sequence
<220> FEATURE:
<223> OTHER INFORMATION: Synthetic

<400> SEQUENCE: 13

Glu Ile Val Leu Thr Gln Ser Pro Ala Ile Met Ser Ala Ser Pro Gly
1               5                   10                  15

Glu Arg Val Thr Met Thr Cys Ser Ala Ser Ser Gly Val Asn Tyr Met
                20                  25                  30

His Trp Tyr Gln Gln Lys Pro Gly Thr Ser Pro Arg Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Asp Tyr Ser Leu Thr Ile Ser Ser Met Glu Pro Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys Arg Gly Ser Thr Ser Gly Ser Gly
            100                 105                 110

Lys Pro Gly Ser Gly Glu Gly Ser Thr Lys Gly Gln Val Gln Leu Val
        115                 120                 125

Gln Pro Gly Ala Glu Val Val Lys Pro Gly Ala Ser Val Lys Leu Ser
    130                 135                 140

Cys Lys Thr Ser Gly Tyr Thr Phe Thr Ser Asn Trp Met His Trp Val
145                 150                 155                 160
```

```
Lys Gln Ala Pro Gly Gln Gly Leu Glu Trp Ile Gly Glu Ile Asp Pro
                165                 170                 175
Ser Asp Ser Tyr Thr Asn Tyr Asn Gln Asn Phe Gln Gly Lys Ala Lys
            180                 185                 190
Leu Thr Val Asp Lys Ser Thr Ser Thr Ala Tyr Met Glu Val Ser Ser
        195                 200                 205
Leu Arg Ser Asp Asp Thr Ala Val Tyr Tyr Cys Ala Arg Gly Ser Asn
    210                 215                 220
Pro Tyr Tyr Ala Met Asp Tyr Trp Gly Gln Gly Thr Ser Val Thr
225                 230                 235                 240
Val Ser Ser Gly Gly Gly Ala Ser Asp Lys Thr His Thr Cys Pro Pro
                245                 250                 255
Cys Pro Ala Pro Glu Leu Leu Gly Gly Pro Ser Val Phe Leu Phe Pro
            260                 265                 270
Pro Lys Pro Lys Asp Thr Leu Met Ile Ser Arg Thr Pro Glu Val Thr
        275                 280                 285
Cys Val Val Val Asp Val Ser His Glu Asp Pro Glu Val Lys Phe Asn
    290                 295                 300
Trp Tyr Val Asp Gly Val Glu Val His Asn Ala Lys Thr Lys Pro Arg
305                 310                 315                 320
Glu Glu Gln Tyr Asn Ser Thr Tyr Arg Val Val Ser Val Leu Thr Val
                325                 330                 335
Leu His Gln Asp Trp Leu Asn Gly Lys Asp Tyr Lys Cys Lys Val Ser
            340                 345                 350
Asn Lys Ala Leu Pro Ala Pro Ile Glu Lys Thr Ile Ser Lys Ala Lys
        355                 360                 365
Gly Gln Pro Arg Glu Pro Gln Val Tyr Thr Leu Pro Pro Ser Arg Asp
    370                 375                 380
Glu Leu Thr Arg Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
                405                 410                 415
Asn Asn Tyr Lys Thr Thr Pro Pro Val Leu Asp Ser Asp Gly Ser Phe
            420                 425                 430
Phe Leu Tyr Ser Lys Leu Thr Val Asp Lys Ser Arg Trp Gln Gln Gly
        435                 440                 445
Asn Val Phe Ser Cys Ser Val Met His Glu Ala Leu His Asn His Tyr
    450                 455                 460
Thr Gln Lys Ser Leu Ser Leu Ser Pro Gly Gly Gly Ala Cys Pro
465                 470                 475                 480
Gly His Ala

<210> SEQ ID NO 14
<211> LENGTH: 483
<212> TYPE: PRT
<213> ORGANISM: Artificial Sequence
<220> FEATURE:
<223> OTHER INFORMATION: Synthetic

<400> SEQUENCE: 14

Gln Val Gln Leu Val Gln Pro Gly Ala Glu Val Val Lys Pro Gly Ala
1               5                   10                  15
Ser Val Lys Leu Ser Cys Lys Thr Ser Gly Tyr Thr Phe Thr Ser Asn
                20                  25                  30
Trp Met His Trp Val Lys Gln Ala Pro Gly Gln Gly Leu Glu Trp Ile
```

```
                    35                  40                  45
Gly Glu Ile Asp Pro Ser Asp Ser Tyr Thr Asn Tyr Asn Gln Asn Phe
 50                  55                  60

Gln Gly Lys Ala Lys Leu Thr Val Asp Lys Ser Thr Ser Thr Ala Tyr
 65                  70                  75                  80

Met Glu Val Ser Ser Leu Arg Ser Asp Thr Ala Val Tyr Tyr Cys
                 85                  90                  95

Ala Arg Gly Ser Asn Pro Tyr Tyr Tyr Ala Met Asp Tyr Trp Gly Gln
                100                 105                 110

Gly Thr Ser Val Thr Val Ser Ser Gly Ser Thr Ser Gly Ser Gly Lys
                115                 120                 125

Pro Gly Ser Gly Glu Gly Ser Thr Lys Gly Glu Ile Val Leu Thr Gln
                130                 135                 140

Ser Pro Ala Ile Met Ser Ala Ser Pro Gly Glu Arg Val Thr Met Thr
145                 150                 155                 160

Cys Ser Ala Ser Ser Gly Val Asn Tyr Met His Trp Tyr Gln Gln Lys
                165                 170                 175

Pro Gly Thr Ser Pro Arg Arg Trp Ile Tyr Asp Thr Ser Lys Leu Ala
                180                 185                 190

Ser Gly Val Pro Ala Arg Phe Ser Gly Ser Gly Ser Gly Thr Asp Tyr
                195                 200                 205

Ser Leu Thr Ile Ser Ser Met Glu Pro Glu Asp Ala Ala Thr Tyr Tyr
210                 215                 220

Cys His Gln Arg Gly Ser Tyr Thr Phe Gly Gly Gly Thr Lys Leu Glu
225                 230                 235                 240

Ile Lys Arg Gly Gly Gly Ala Ser Asp Lys Thr His Thr Cys Pro Pro
                245                 250                 255

Cys Pro Ala Pro Glu Leu Leu Gly Gly Pro Ser Val Phe Leu Phe Pro
                260                 265                 270

Pro Lys Pro Lys Asp Thr Leu Met Ile Ser Arg Thr Pro Glu Val Thr
                275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Asp Tyr Lys Cys Lys Val Ser
                340                 345                 350

Asn Lys Ala Leu Pro Ala Pro Ile Glu Lys Thr Ile Ser Lys Ala Lys
                355                 360                 365

Gly Gln Pro Arg Glu Pro Gln Val Tyr Thr Leu Pro Pro Ser Arg Asp
                370                 375                 380

Glu Leu Thr Arg Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
                420                 425                 430

Phe Leu Tyr Ser Lys Leu Thr Val Asp Lys Ser Arg Trp Gln Gln Gly
                435                 440                 445

Asn Val Phe Ser Cys Ser Val Met His Glu Ala Leu His Asn His Tyr
                450                 455                 460
```

Thr Gln Lys Ser Leu Ser Leu Ser Pro Gly Gly Gly Ala Cys Pro
465                 470                 475                 480

Gly His Ala

<210> SEQ ID NO 15
<211> LENGTH: 483
<212> TYPE: PRT
<213> ORGANISM: Artificial Sequence
<220> FEATURE:
<223> OTHER INFORMATION: Synthetic

<400> SEQUENCE: 15

Glu Ile Val Leu Thr Gln Ser Pro Ala Ile Met Ser Ala Ser Pro Gly
1               5                   10                  15

Glu Arg Val Thr Met Thr Cys Ser Ala Ser Ser Gly Val Asn Tyr Met
            20                  25                  30

His Trp Tyr Gln Gln Lys Pro Gly Thr Ser Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Ser Leu Thr Ile Ser Ser Met Glu Pro Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys Arg Gly Ser Thr Ser Gly Ser Gly
            100                 105                 110

Lys Pro Gly Ser Gly Glu Gly Ser Thr Lys Gly Gln Val Gln Leu Val
        115                 120                 125

Gln Pro Gly Ala Glu Val Val Lys Pro Gly Ala Ser Val Lys Leu Ser
    130                 135                 140

Cys Lys Thr Ser Gly Tyr Thr Phe Thr Ser Asn Trp Met His Trp Val
145                 150                 155                 160

Lys Gln Ala Pro Gly Gln Gly Leu Glu Trp Ile Gly Glu Ile Asp Pro
                165                 170                 175

Ser Asp Ser Tyr Thr Asn Tyr Asn Gln Asn Phe Gln Gly Lys Ala Lys
            180                 185                 190

Leu Thr Val Asp Lys Ser Thr Ser Thr Ala Tyr Met Glu Val Ser Ser
        195                 200                 205

Leu Arg Ser Asp Asp Thr Ala Val Tyr Tyr Cys Ala Arg Gly Ser Asn
    210                 215                 220

Pro Tyr Tyr Tyr Ala Met Asp Tyr Trp Gly Gln Gly Thr Ser Val Thr
225                 230                 235                 240

Val Ser Ser Gly Gly Gly Ala Ser Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

```
Leu His Gln Asp Trp Leu Asn Gly Lys Asp Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Arg Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Gly Gly Gly Cys Pro
465                 470                 475                 480

Gly His Ala

<210> SEQ ID NO 16
<211> LENGTH: 483
<212> TYPE: PRT
<213> ORGANISM: Artificial Sequence
<220> FEATURE:
<223> OTHER INFORMATION: Synthetic

<400> SEQUENCE: 16

Glu Ile Val Leu Thr Gln Ser Pro Ala Ile Met Ser Ala Ser Pro Gly
1               5                   10                  15

Glu Arg Val Thr Met Thr Cys Ser Ala Ser Ser Gly Val Asn Tyr Met
            20                  25                  30

His Trp Tyr Gln Gln Lys Pro Gly Thr Ser Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Ser Leu Thr Ile Ser Ser Met Glu Pro Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys Arg Gly Ser Thr Ser Gly Ser Gly
            100                 105                 110

Lys Pro Gly Ser Gly Glu Gly Ser Thr Lys Gly Gln Val Gln Leu Val
        115                 120                 125

Gln Pro Gly Ala Glu Val Val Lys Pro Gly Ala Ser Val Lys Leu Ser
    130                 135                 140

Cys Lys Thr Ser Gly Tyr Thr Phe Thr Ser Asn Trp Met His Trp Val
145                 150                 155                 160

Lys Gln Ala Pro Gly Gln Gly Leu Glu Trp Ile Gly Glu Ile Asp Pro
                165                 170                 175

Ser Asp Ser Tyr Thr Asn Tyr Asn Gln Asn Phe Gln Gly Lys Ala Lys
            180                 185                 190

Leu Thr Val Asp Lys Ser Thr Ser Thr Ala Tyr Met Glu Val Ser Ser
        195                 200                 205

Leu Arg Ser Asp Asp Thr Ala Val Tyr Tyr Cys Ala Arg Gly Ser Asn
```

```
            210                 215                 220
Pro Tyr Tyr Tyr Ala Met Asp Tyr Trp Gly Gln Gly Thr Ser Val Thr
225                 230                 235                 240

Val Ser Ser Gly Gly Gly Ala Ser Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Asp Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
370                 375                 380

Glu Leu Thr Arg Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
450                 455                 460

Thr Gln Lys Ser Leu Ser Leu Ser Pro Gly Gly Gly Gly Cys Gly
465                 470                 475                 480

Gly His Ala

<210> SEQ ID NO 17
<211> LENGTH: 458
<212> TYPE: PRT
<213> ORGANISM: Artificial Sequence
<220> FEATURE:
<223> OTHER INFORMATION: Synthetic

<400> SEQUENCE: 17

Gln Val Gln Leu Val Gln Pro Gly Ala Glu Val Val Lys Pro Gly Ala
1               5                   10                  15

Ser Val Lys Leu Ser Cys Lys Thr Ser Gly Tyr Thr Phe Thr Ser Asn
                20                  25                  30

Trp Met His Trp Val Lys Gln Ala Pro Gly Gln Gly Leu Glu Trp Ile
            35                  40                  45

Gly Glu Ile Asp Pro Ser Asp Ser Tyr Thr Asn Tyr Asn Gln Asn Phe
        50                  55                  60

Gln Gly Lys Ala Lys Leu Thr Val Asp Lys Ser Thr Ser Thr Ala Tyr
65                  70                  75                  80

Met Glu Val Ser Ser Leu Arg Ser Asp Asp Thr Ala Val Tyr Tyr Cys
                85                  90                  95
```

Ala Arg Gly Ser Asn Pro Tyr Tyr Ala Met Asp Tyr Trp Gly Gln
             100                 105                 110

Gly Thr Ser Val Thr Val Ser Ala Ser Thr Lys Gly Pro Ser Val
         115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
         195                 200                 205

Pro Ser Asn Thr Lys Val Asp Lys Lys Ala Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
         275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Asp Tyr Lys Cys Lys Val Ser Asn Lys Ala Leu Pro Ala Pro Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Arg Asp Glu Leu Thr Arg Asn Gln Val Ser Leu
         355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Gln Gly Asn Val Phe Ser Cys Ser Val Met His
             420                 425                 430

Glu Ala Leu His Asn His Tyr Thr Gln Lys Ser Leu Ser Leu Ser Pro
         435                 440                 445

Gly Gly Gly Gly Ala Cys Pro Gly His Ala
450                 455

<210> SEQ ID NO 18
<211> LENGTH: 458
<212> TYPE: PRT
<213> ORGANISM: Artificial Sequence
<220> FEATURE:
<223> OTHER INFORMATION: Synthetic

<400> SEQUENCE: 18

```
Gln Val Gln Leu Val Gln Pro Gly Ala Glu Val Lys Pro Gly Ala
1               5                   10                  15

Ser Val Lys Leu Ser Cys Lys Thr Ser Gly Tyr Thr Phe Thr Ser Asn
            20                  25                  30

Trp Met His Trp Val Lys Gln Ala Pro Gly Gln Gly Leu Glu Trp Ile
            35                  40                  45

Gly Glu Ile Asp Pro Ser Asp Ser Tyr Thr Asn Tyr Asn Gln Asn Phe
    50                  55                  60

Gln Gly Lys Ala Lys Leu Thr Val Asp Lys Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Arg Gly Ser Asn Pro Tyr Tyr Tyr Ala Met Asp Tyr Trp Gly Gln
            100                 105                 110

Gly Thr Ser Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Ala Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Asp Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Arg Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Gly Gly Gly Gly Cys Pro Gly His Ala
    450                 455

<210> SEQ ID NO 19
<211> LENGTH: 211
<212> TYPE: PRT
<213> ORGANISM: Artificial Sequence
<220> FEATURE:
<223> OTHER INFORMATION: Synthetic

<400> SEQUENCE: 19

Glu Ile Val Leu Thr Gln Ser Pro Ala Ile Met Ser Ala Ser Pro Gly
1               5                   10                  15

Glu Arg Val Thr Met Thr Cys Ser Ala Ser Ser Gly Val Asn Tyr Met
            20                  25                  30

His Trp Tyr Gln Gln Lys Pro Gly Thr Ser Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Ser Leu Thr Ile Ser Ser Met Glu Pro Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 20
<211> LENGTH: 489
<212> TYPE: PRT
<213> ORGANISM: Artificial Sequence
<220> FEATURE:
<223> OTHER INFORMATION: Synthetic

<400> SEQUENCE: 20

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45
```

```
Ser Pro Arg Leu Leu Thr Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65              70                  75                  80

Ile Ser Ser Val Gln Pro Glu Asp Leu Ala Ile Tyr Tyr Cys His Gln
                 85                  90                  95

Tyr Leu Ser Ser Arg Thr Phe Gly Gln Gly Thr Lys Leu Glu Ile Lys
             100                 105                 110

Arg Gly Ser Thr Ser Gly Ser Gly Lys Pro Gly Ser Gly Glu Gly Ser
             115                 120                 125

Thr Lys Gly Gln Val Gln Leu Gln Gln Pro Gly Ala Glu Val Val Lys
        130                 135                 140

Pro Gly Ala Ser Val Lys Met Ser Cys Lys Ala Ser Gly Tyr Thr Phe
145                 150                 155                 160

Thr Ser Tyr Tyr Ile His Trp Ile Lys Gln Thr Pro Gly Gln Gly Leu
                 165                 170                 175

Glu Trp Val Gly Val Ile Tyr Pro Gly Asn Asp Asp Ile Ser Tyr Asn
             180                 185                 190

Gln Lys Phe Gln Gly Lys Ala Thr Leu Thr Ala Asp Lys Ser Ser Thr
         195                 200                 205

Thr Ala Tyr Met Gln Leu Ser Ser Leu Thr Ser Glu Asp Ser Ala Val
    210                 215                 220

Tyr Tyr Cys Ala Arg Glu Val Arg Leu Arg Tyr Phe Asp Val Trp Gly
225                 230                 235                 240

Gln Gly Thr Thr Val Thr Val Ser Ser Gly Gly Gly Ala Ser Asp Lys
             245                 250                 255

Thr His Thr Cys Pro Pro Cys Pro Ala Pro Glu Leu Leu Gly Gly Pro
         260                 265                 270

Ser Val Phe Leu Phe Pro Pro Lys Pro Lys Asp Thr Leu Met Ile Ser
     275                 280                 285

Arg Thr Pro Glu Val Thr Cys Val Val Val Asp Val Ser His Glu Asp
         290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
             325                 330                 335

Val Ser Val Leu Thr Val Leu His Gln Asp Trp Leu Asn Gly Lys Asp
         340                 345                 350

Tyr Lys Cys Lys Val Ser Asn Lys Ala Leu Pro Ala Pro Ile Glu Lys
     355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Arg Asn Gln Val Ser Leu Thr
385                 390                 395                 400

Cys Leu Val Lys Gly Phe Tyr Pro Ser Asp Ile Ala Val Glu Trp Glu
             405                 410                 415

Ser Asn Gly Gln Pro Glu Asn Asn Tyr Lys Thr Thr Pro Pro Val Leu
         420                 425                 430

Asp Ser Asp Gly Ser Phe Phe Leu Tyr Ser Lys Leu Thr Val Asp Lys
     435                 440                 445

Ser Arg Trp Gln Gln Gly Asn Val Phe Ser Cys Ser Val Met His Glu
    450                 455                 460
```

```
Ala Leu His Asn His Tyr Thr Gln Lys Ser Leu Ser Leu Ser Pro Gly
465                 470                 475                 480

Gly Gly Gly Ala Cys Pro Gly His Ala
            485
```

<210> SEQ ID NO 21
<211> LENGTH: 489
<212> TYPE: PRT
<213> ORGANISM: Artificial Sequence
<220> FEATURE:
<223> OTHER INFORMATION: Synthetic

<400> SEQUENCE: 21

```
Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
    50                  55                  60

Gln Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Gln Gly Thr
            100                 105                 110

Thr Val Thr Val Ser Ser Gly Ser Thr Ser Gly Ser Gly Lys Pro Gly
        115                 120                 125

Ser Gly Glu Gly Ser Thr Lys Gly Glu Ile Val Leu Thr Gln Ser Pro
    130                 135                 140

Gly Ser Leu Ala Val Ser Pro Gly Glu Arg Val Thr Met Ser Cys Lys
145                 150                 155                 160

Ser Ser Gln Ser Val Phe Phe Ser Ser Ser Gln Lys Asn Tyr Leu Ala
                165                 170                 175

Trp Tyr Gln Gln Ile Pro Gly Gln Ser Pro Arg Leu Leu Thr Tyr Trp
            180                 185                 190

Ala Ser Thr Arg Glu Ser Gly Val Pro Asp Arg Phe Thr Gly Ser Gly
        195                 200                 205

Ser Gly Thr Asp Phe Thr Leu Thr Ile Ser Ser Val Gln Pro Glu Asp
    210                 215                 220

Leu Ala Ile Tyr Tyr Cys His Gln Tyr Leu Ser Ser Arg Thr Phe Gly
225                 230                 235                 240

Gln Gly Thr Lys Leu Glu Ile Lys Arg Gly Gly Ala Ser Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335
```

Val Ser Val Leu Thr Val Leu His Gln Asp Trp Leu Asn Gly Lys Asp
                340                 345                 350

Tyr Lys Cys Lys Val Ser Asn Lys Ala Leu Pro Ala Pro Ile Glu Lys
            355                 360                 365

Thr Ile Ser Lys Ala Lys Gly Gln Pro Arg Glu Pro Gln Val Tyr Thr
        370                 375                 380

Leu Pro Pro Ser Arg Asp Glu Leu Thr Arg Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Gly Gly Gly Ala Cys Pro Gly His Ala
                485

<210> SEQ ID NO 22
<211> LENGTH: 489
<212> TYPE: PRT
<213> ORGANISM: Artificial Sequence
<220> FEATURE:
<223> OTHER INFORMATION: Synthetic

<400> SEQUENCE: 22

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Arg Leu Leu Thr Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
            100                 105                 110

Arg Gly Ser Thr Ser Gly Ser Gly Lys Pro Gly Ser Gly Glu Gly Ser
        115                 120                 125

Thr Lys Gly Gln Val Gln Leu Gln Gln Pro Gly Ala Glu Val Val Lys
    130                 135                 140

Pro Gly Ala Ser Val Lys Met Ser Cys Lys Ala Ser Gly Tyr Thr Phe
145                 150                 155                 160

Thr Ser Tyr Tyr Ile His Trp Ile Lys Gln Thr Pro Gly Gln Gly Leu
                165                 170                 175

Glu Trp Val Gly Val Ile Tyr Pro Gly Asn Asp Asp Ile Ser Tyr Asn
            180                 185                 190

Gln Lys Phe Gln Gly Lys Ala Thr Leu Thr Ala Asp Lys Ser Ser Thr
        195                 200                 205

```
Thr Ala Tyr Met Gln Leu Ser Ser Leu Thr Ser Glu Asp Ser Ala Val
            210                 215                 220

Tyr Tyr Cys Ala Arg Glu Val Arg Leu Arg Tyr Phe Asp Val Trp Gly
225                 230                 235                 240

Gln Gly Thr Thr Val Thr Val Ser Ser Gly Gly Ala Ser Asp Lys
                245                 250                 255

Thr His Thr Cys Pro Pro Cys Pro Ala Pro Glu Leu Leu Gly Gly Pro
                260                 265                 270

Ser Val Phe Leu Phe Pro Pro Lys Pro Lys Asp Thr Leu Met Ile Ser
            275                 280                 285

Arg Thr Pro Glu Val Thr Cys Val Val Val Asp Val Ser His Glu Asp
290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Asp
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
370                 375                 380

Leu Pro Pro Ser Arg Asp Glu Leu Thr Arg Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Gly Gly Gly Gly Cys Pro Gly His Ala
                485

<210> SEQ ID NO 23
<211> LENGTH: 489
<212> TYPE: PRT
<213> ORGANISM: Artificial Sequence
<220> FEATURE:
<223> OTHER INFORMATION: Synthetic

<400> SEQUENCE: 23

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
    50                  55                  60

Gln Gly Lys Ala Thr Leu Thr Ala Asp Lys Ser Ser Thr Thr Ala Tyr
65                  70                  75                  80
```

```
Met Gln Leu Ser Ser Leu Thr Ser Glu Asp Ser Ala Val Tyr Tyr Cys
                 85                  90                  95

Ala Arg Glu Val Arg Leu Arg Tyr Phe Asp Val Trp Gly Gln Gly Thr
            100                 105                 110

Thr Val Thr Val Ser Ser Gly Ser Thr Ser Gly Ser Gly Lys Pro Gly
            115                 120                 125

Ser Gly Glu Gly Ser Thr Lys Gly Glu Ile Val Leu Thr Gln Ser Pro
            130                 135                 140

Gly Ser Leu Ala Val Ser Pro Gly Glu Arg Val Thr Met Ser Cys Lys
145                 150                 155                 160

Ser Ser Gln Ser Val Phe Phe Ser Ser Gln Lys Asn Tyr Leu Ala
                165                 170                 175

Trp Tyr Gln Gln Ile Pro Gly Gln Ser Pro Arg Leu Leu Thr Tyr Trp
                180                 185                 190

Ala Ser Thr Arg Glu Ser Gly Val Pro Asp Arg Phe Thr Gly Ser Gly
            195                 200                 205

Ser Gly Thr Asp Phe Thr Leu Thr Ile Ser Ser Val Gln Pro Glu Asp
            210                 215                 220

Leu Ala Ile Tyr Tyr Cys His Gln Tyr Leu Ser Ser Arg Thr Phe Gly
225                 230                 235                 240

Gln Gly Thr Lys Leu Glu Ile Lys Arg Gly Gly Ala Ser Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
                275                 280                 285

Arg Thr Pro Glu Val Thr Cys Val Val Val Asp Val Ser His Glu Asp
290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
            325                 330                 335

Val Ser Val Leu Thr Val Leu His Gln Asp Trp Leu Asn Gly Lys Asp
            340                 345                 350

Tyr Lys Cys Lys Val Ser Asn Lys Ala Leu Pro Ala Pro Ile Glu Lys
            355                 360                 365

Thr Ile Ser Lys Ala Lys Gly Gln Pro Arg Glu Pro Gln Val Tyr Thr
            370                 375                 380

Leu Pro Pro Ser Arg Asp Glu Leu Thr Arg Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
            435                 440                 445

Ser Arg Trp Gln Gln Gly Asn Val Phe Ser Cys Ser Val Met His Glu
            450                 455                 460

Ala Leu His Asn His Tyr Thr Gln Lys Ser Leu Ser Leu Ser Pro Gly
465                 470                 475                 480

Gly Gly Gly Gly Cys Pro Gly His Ala
                485
```

-continued

<210> SEQ ID NO 24
<211> LENGTH: 487
<212> TYPE: PRT
<213> ORGANISM: Artificial Sequence
<220> FEATURE:
<223> OTHER INFORMATION: Synthetic

<400> SEQUENCE: 24

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Val Glu Ile Lys Arg Gly Ser Thr Ser Gly
            100                 105                 110

Ser Gly Lys Pro Gly Ser Gly Glu Gly Ser Thr Lys Gly Glu Val Gln
        115                 120                 125

Leu Val Glu Ser Gly Gly Gly Leu Val Gln Pro Gly Gly Ser Leu Arg
130                 135                 140

Leu Ser Cys Ala Ala Ser Gly Tyr Thr Phe Thr Ser Tyr Asn Met His
145                 150                 155                 160

Trp Val Arg Gln Ala Pro Gly Lys Gly Leu Glu Trp Val Gly Ala Ile
                165                 170                 175

Tyr Pro Gly Asn Gly Asp Thr Ser Tyr Asn Gln Lys Phe Lys Gly Arg
            180                 185                 190

Phe Thr Ile Ser Val Asp Lys Ser Lys Asn Thr Leu Tyr Leu Gln Met
        195                 200                 205

Asn Ser Leu Arg Ala Glu Asp Thr Ala Val Tyr Tyr Cys Ala Arg Val
210                 215                 220

Val Tyr Tyr Ser Asn Ser Tyr Trp Tyr Phe Asp Val Trp Gly Gln Gly
225                 230                 235                 240

Thr Leu Val Thr Val Ser Ser Gly Gly Gly Ala Ser Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Asp Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
```

```
                370             375             380
Pro Ser Arg Asp Glu Leu Thr Arg Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
            435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Gly Gly
465                 470                 475                 480

Gly Ala Cys Pro Gly His Ala
                485

<210> SEQ ID NO 25
<211> LENGTH: 487
<212> TYPE: PRT
<213> ORGANISM: Artificial Sequence
<220> FEATURE:
<223> OTHER INFORMATION: Synthetic

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
                20                  25                  30

Asn Met His Trp Val Arg Gln Ala Pro Gly Lys Gly Leu Glu Trp Val
            35                  40                  45

Gly Ala Ile Tyr Pro Gly Asn Gly Asp Thr Ser Tyr Asn Gln Lys Phe
        50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
                100                 105                 110

Gly Gln Gly Thr Leu Val Thr Val Ser Ser Gly Ser Thr Ser Gly Ser
            115                 120                 125

Gly Lys Pro Gly Ser Gly Glu Gly Ser Thr Lys Gly Asp Ile Gln Met
        130                 135                 140

Thr Gln Ser Pro Ser Ser Leu Ser Ala Ser Val Gly Asp Arg Val Thr
145                 150                 155                 160

Ile Thr Cys Arg Ala Ser Ser Val Ser Tyr Met His Trp Tyr Gln
                165                 170                 175

Gln Lys Pro Gly Lys Ala Pro Lys Pro Leu Ile Tyr Ala Pro Ser Asn
            180                 185                 190

Leu Ala Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Trp Ser Phe Asn Pro Pro Thr Phe Gly Gln Gly
225                 230                 235                 240

Thr Lys Val Glu Ile Lys Arg Gly Gly Gly Ala Ser Asp Lys Thr His
```

```
            245                 250                 255
Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
            275                 280                 285

Pro Glu Val Thr Cys Val Val Val Asp Val Ser His Glu Asp Pro Glu
            290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
            325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
            355                 360                 365

Ser Lys Ala Lys Gly Gln Pro Arg Glu Pro Gln Val Tyr Thr Leu Pro
            370                 375                 380

Pro Ser Arg Asp Glu Leu Thr Arg Asn Gln Val Ser Leu Thr Cys Leu
385                 390                 395                 400

Val Lys Gly Phe Tyr Pro Ser Asp Ile Ala Val Glu Trp Glu Ser Asn
                        405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
            435                 440                 445

Trp Gln Gln Gly Asn Val Phe Ser Cys Ser Val Met His Glu Ala Leu
            450                 455                 460

His Asn His Tyr Thr Gln Lys Ser Leu Ser Leu Ser Pro Gly Gly Gly
465                 470                 475                 480

Gly Ala Cys Pro Gly His Ala
            485

<210> SEQ ID NO 26
<211> LENGTH: 487
<212> TYPE: PRT
<213> ORGANISM: Artificial Sequence
<220> FEATURE:
<223> OTHER INFORMATION: Synthetic

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
            35                  40                  45

Gly Ala Ile Tyr Pro Gly Asn Gly Asp Thr Ser Tyr Asn Gln Lys Phe
            50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser Gly Ser Thr Ser Gly Ser
```

```
            115                 120                 125
Gly Lys Pro Gly Ser Gly Glu Gly Ser Thr Lys Gly Asp Ile Gln Met
        130                 135                 140

Thr Gln Ser Pro Ser Ser Leu Ser Ala Ser Val Gly Asp Arg Val Thr
145                 150                 155                 160

Ile Thr Cys Arg Ala Ser Ser Val Ser Tyr Met His Trp Tyr Gln
                165                 170                 175

Gln Lys Pro Gly Lys Ala Pro Lys Pro Leu Ile Tyr Ala Pro Ser Asn
            180                 185                 190

Leu Ala Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
        210                 215                 220

Tyr Tyr Cys Gln Gln Trp Ser Phe Asn Pro Pro Thr Phe Gly Gln Gly
225                 230                 235                 240

Thr Lys Val Glu Ile Lys Arg Gly Gly Gly Ala Ser Asp Lys Thr His
                245                 250                 255

Thr Cys Pro Pro Cys Pro Ala Pro Glu Leu Leu Gly Gly Pro Ser Val
                260                 265                 270

Phe Leu Phe Pro Pro Lys Pro Lys Asp Thr Leu Met Ile Ser Arg Thr
            275                 280                 285

Pro Glu Val Thr Cys Val Val Val Asp Val Ser His Glu Asp Pro Glu
        290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Asp Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Arg Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Gly Gly
465                 470                 475                 480

Gly Gly Cys Pro Gly His Ala
                485
```

<210> SEQ ID NO 27
<211> LENGTH: 487
<212> TYPE: PRT
<213> ORGANISM: Artificial Sequence
<220> FEATURE:
<223> OTHER INFORMATION: Synthetic

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Leu Ile Tyr
            35                  40                  45

Ala Pro Ser Asn Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Val Glu Ile Lys Arg Gly Thr Ser Gly
                100                 105                 110

Ser Gly Lys Pro Gly Ser Gly Glu Gly Ser Thr Lys Gly Glu Val Gln
            115                 120                 125

Leu Val Glu Ser Gly Gly Gly Leu Val Gln Pro Gly Gly Ser Leu Arg
    130                 135                 140

Leu Ser Cys Ala Ala Ser Gly Tyr Thr Phe Thr Ser Tyr Asn Met His
145                 150                 155                 160

Trp Val Arg Gln Ala Pro Gly Lys Gly Leu Glu Trp Val Gly Ala Ile
                165                 170                 175

Tyr Pro Gly Asn Gly Asp Thr Ser Tyr Asn Gln Lys Phe Lys Gly Arg
                180                 185                 190

Phe Thr Ile Ser Val Asp Lys Ser Lys Asn Thr Leu Tyr Leu Gln Met
            195                 200                 205

Asn Ser Leu Arg Ala Glu Asp Thr Ala Val Tyr Tyr Cys Ala Arg Val
        210                 215                 220

Val Tyr Tyr Ser Asn Ser Tyr Trp Tyr Phe Asp Val Trp Gly Gln Gly
225                 230                 235                 240

Thr Leu Val Thr Val Ser Ser Gly Gly Gly Ala Ser Asp Lys Thr His
                245                 250                 255

Thr Cys Pro Pro Cys Pro Ala Pro Glu Leu Leu Gly Gly Pro Ser Val
                260                 265                 270

Phe Leu Phe Pro Pro Lys Pro Lys Asp Thr Leu Met Ile Ser Arg Thr
            275                 280                 285

Pro Glu Val Thr Cys Val Val Val Asp Val Ser His Glu Asp Pro Glu
        290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Asp Tyr Lys
                340                 345                 350

Cys Lys Val Ser Asn Lys Ala Leu Pro Ala Pro Ile Glu Lys Thr Ile
            355                 360                 365

Ser Lys Ala Lys Gly Gln Pro Arg Glu Pro Gln Val Tyr Thr Leu Pro
        370                 375                 380

Pro Ser Arg Asp Glu Leu Thr Arg Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415
```

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
            435                 440                 445

Trp Gln Gln Gly Asn Val Phe Ser Cys Ser Val Met His Glu Ala Leu
450                 455                 460

His Asn His Tyr Thr Gln Lys Ser Leu Ser Leu Ser Pro Gly Gly Gly
465                 470                 475                 480

Gly Gly Cys Gly Gly His Ala
                485

<210> SEQ ID NO 28
<211> LENGTH: 487
<212> TYPE: PRT
<213> ORGANISM: Artificial Sequence
<220> FEATURE:
<223> OTHER INFORMATION: Synthetic

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
            35                  40                  45

Gly Ala Ile Tyr Pro Gly Asn Gly Asp Thr Ser Tyr Asn Gln Lys Phe
        50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser Gly Ser Thr Ser Gly Ser
            115                 120                 125

Gly Lys Pro Gly Ser Gly Glu Gly Ser Thr Lys Gly Asp Ile Gln Met
        130                 135                 140

Thr Gln Ser Pro Ser Ser Leu Ser Ala Ser Val Gly Asp Arg Val Thr
145                 150                 155                 160

Ile Thr Cys Arg Ala Ser Ser Val Ser Tyr Met His Trp Tyr Gln
                165                 170                 175

Gln Lys Pro Gly Lys Ala Pro Lys Pro Leu Ile Tyr Ala Pro Ser Asn
            180                 185                 190

Leu Ala Ser Gly Val Pro Ser Arg Phe Ser Gly Ser Gly Ser Gly Thr
            195                 200                 205

Asp Phe Thr Leu Thr Ile Ser Ser Leu Gln Pro Glu Asp Phe Ala Thr
        210                 215                 220

Tyr Tyr Cys Gln Gln Trp Ser Phe Asn Pro Pro Thr Phe Gly Gln Gly
225                 230                 235                 240

Thr Lys Val Glu Ile Lys Arg Gly Gly Gly Ala Ser Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
            275                 280                 285

```
Pro Glu Val Thr Cys Val Val Asp Val Ser His Glu Asp Pro Glu
    290             295                 300
Val Lys Phe Asn Trp Tyr Val Asp Gly Val Glu Val His Asn Ala Lys
305                 310                 315                 320
Thr Lys Pro Arg Glu Glu Gln Tyr Asn Ser Thr Tyr Arg Val Val Ser
                325                 330                 335
Val Leu Thr Val Leu His Gln Asp Trp Leu Asn Gly Lys Asp Tyr Lys
            340                 345                 350
Cys Lys Val Ser Asn Lys Ala Leu Pro Ala Pro Ile Glu Lys Thr Ile
        355                 360                 365
Ser Lys Ala Lys Gly Gln Pro Arg Glu Pro Gln Val Tyr Thr Leu Pro
    370                 375                 380
Pro Ser Arg Asp Glu Leu Thr Arg Asn Gln Val Ser Leu Thr Cys Leu
385                 390                 395                 400
Val Lys Gly Phe Tyr Pro Ser Asp Ile Ala Val Glu Trp Glu Ser Asn
                405                 410                 415
Gly Gln Pro Glu Asn Asn Tyr Lys Thr Thr Pro Pro Val Leu Asp Ser
            420                 425                 430
Asp Gly Ser Phe Phe Leu Tyr Ser Lys Leu Thr Val Asp Lys Ser Arg
        435                 440                 445
Trp Gln Gln Gly Asn Val Phe Ser Cys Ser Val Met His Glu Ala Leu
    450                 455                 460
His Asn His Tyr Thr Gln Lys Ser Leu Ser Leu Ser Pro Gly Gly Gly
465                 470                 475                 480
Gly Gly Cys Gly Gly His Ala
                485
```

<210> SEQ ID NO 29
<211> LENGTH: 108
<212> TYPE: PRT
<213> ORGANISM: Artificial Sequence
<220> FEATURE:
<223> OTHER INFORMATION: Synthetic

<400> SEQUENCE: 29

```
Asp Ile Gln Met Thr Gln Ser Pro Ser Ser Met Tyr Ala Ser Leu Gly
1               5                   10                  15
Glu Arg Val Thr Ile Thr Cys Lys Ala Ser Gln Asp Ile Asn Ser Tyr
            20                  25                  30
Leu Ser Trp Phe Gln Gln Lys Pro Gly Lys Ser Pro Lys Thr Leu Ile
        35                  40                  45
Tyr Arg Ala Asn Arg Leu Val Asp Gly Val Pro Ser Arg Phe Ser Gly
    50                  55                  60
Ser Gly Ser Gly Gln Asp Tyr Ser Leu Thr Ile Ser Ser Leu Glu Tyr
65                  70                  75                  80
Glu Asp Met Gly Ile Tyr Tyr Cys Leu Gln Tyr Asp Glu Phe Pro Arg
                85                  90                  95
Thr Phe Gly Gly Gly Thr Lys Leu Glu Ile Lys Arg
            100                 105
```

<210> SEQ ID NO 30
<211> LENGTH: 115
<212> TYPE: PRT
<213> ORGANISM: Artificial Sequence
<220> FEATURE:
<223> OTHER INFORMATION: Synthetic

```
<400> SEQUENCE: 30

Glu Val Lys Leu Gln Gln Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Gly Asn Lys Gly Asn Asn His Ala Thr Tyr Tyr Ala Glu
    50                  55                  60

Ser Val Lys Gly Arg Phe Thr Val Ser Arg Asp Asp Ser Lys Ser Arg
65                  70                  75                  80

Val Tyr Leu Gln Met Asn Ser Leu Arg Val Glu Asp Thr Gly Thr Tyr
                85                  90                  95

Tyr Cys Thr Thr Arg Phe Ala Tyr Trp Gly Gln Gly Thr Thr Val Thr
            100                 105                 110

Val Ser Ser
        115

<210> SEQ ID NO 31
<211> LENGTH: 481
<212> TYPE: PRT
<213> ORGANISM: Artificial Sequence
<220> FEATURE:
<223> OTHER INFORMATION: Synthetic

<400> SEQUENCE: 31

Asp Ile Gln Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Arg
                85                  90                  95

Thr Phe Gly Gly Gly Thr Lys Leu Glu Ile Lys Arg Gly Ser Thr Ser
            100                 105                 110

Gly Ser Gly Lys Pro Gly Ser Gly Glu Gly Ser Thr Lys Gly Glu Val
        115                 120                 125

Lys Leu Gln Gln Ser Gly Gly Gly Leu Val Gln Pro Gly Gly Ser Met
    130                 135                 140

Lys Leu Ser Cys Ala Ala Ser Gly Phe Thr Phe Ser Asp Ala Trp Met
145                 150                 155                 160

Asp Trp Val Arg Gln Ser Pro Glu Lys Gly Leu Glu Trp Val Ala Glu
                165                 170                 175

Ile Gly Asn Lys Gly Asn Asn His Ala Thr Tyr Tyr Ala Glu Ser Val
            180                 185                 190

Lys Gly Arg Phe Thr Val Ser Arg Asp Asp Ser Lys Ser Arg Val Tyr
        195                 200                 205

Leu Gln Met Asn Ser Leu Arg Val Glu Asp Thr Gly Thr Tyr Tyr Cys
    210                 215                 220

Thr Thr Arg Phe Ala Tyr Trp Gly Gln Gly Thr Thr Val Thr Val Ser
```

```
                    225                 230                 235                 240

Ser Gly Gly Gly Ala Ser Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Arg Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Gly Gly Ala Cys Pro Gly His
465                 470                 475                 480

Ala

<210> SEQ ID NO 32
<211> LENGTH: 481
<212> TYPE: PRT
<213> ORGANISM: Artificial Sequence
<220> FEATURE:
<223> OTHER INFORMATION: Synthetic

<400> SEQUENCE: 32

Asp Ile Gln Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Arg
                85                  90                  95

Thr Phe Gly Gly Gly Thr Lys Leu Glu Ile Lys Arg Gly Ser Thr Ser
            100                 105                 110
```

```
Gly Ser Gly Lys Pro Gly Ser Gly Glu Gly Ser Thr Lys Gly Glu Val
        115                 120                 125
Lys Leu Gln Gln Ser Gly Gly Gly Leu Val Gln Pro Gly Gly Ser Met
130                 135                 140
Lys Leu Ser Cys Ala Ala Ser Gly Phe Thr Phe Ser Asp Ala Trp Met
145                 150                 155                 160
Asp Trp Val Arg Gln Ser Pro Glu Lys Gly Leu Glu Trp Val Ala Glu
                165                 170                 175
Ile Gly Asn Lys Gly Asn Asn His Ala Thr Tyr Tyr Ala Glu Ser Val
            180                 185                 190
Lys Gly Arg Phe Thr Val Ser Arg Asp Asp Ser Lys Ser Arg Val Tyr
        195                 200                 205
Leu Gln Met Asn Ser Leu Arg Val Glu Asp Thr Gly Thr Tyr Tyr Cys
    210                 215                 220
Thr Thr Arg Phe Ala Tyr Trp Gly Gln Gly Thr Thr Val Thr Val Ser
225                 230                 235                 240
Ser Gly Gly Gly Ala Ser Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Asp Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
    370                 375                 380
Thr Arg Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Ala Leu His Asn His Tyr Thr Gln
    450                 455                 460
Lys Ser Leu Ser Leu Ser Pro Gly Gly Gly Gly Cys Gly Gly His
465                 470                 475                 480
Ala

<210> SEQ ID NO 33
<211> LENGTH: 487
<212> TYPE: PRT
<213> ORGANISM: Artificial Sequence
<220> FEATURE:
<223> OTHER INFORMATION: Synthetic
```

<400> SEQUENCE: 33

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Gly Ser Thr Ser Gly
            100                 105                 110

Ser Gly Lys Pro Gly Ser Gly Glu Gly Ser Thr Lys Gly Glu Val Gln
        115                 120                 125

Leu Leu Glu Ser Gly Gly Gly Leu Val Gln Pro Gly Gly Ser Leu Arg
130                 135                 140

Leu Ser Cys Ala Val Ser Gly Phe Thr Phe Asn Ser Phe Ala Met Ser
145                 150                 155                 160

Trp Val Arg Gln Ala Pro Gly Lys Gly Leu Glu Trp Val Ser Ala Ile
                165                 170                 175

Ser Gly Ser Gly Gly Gly Thr Tyr Tyr Ala Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Phe Cys Ala Lys Asp
210                 215                 220

Lys Ile Leu Trp Phe Gly Glu Pro Val Phe Asp Tyr Trp Gly Gln Gly
225                 230                 235                 240

Thr Leu Val Thr Val Ser Ser Gly Gly Gly Ala Ser Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
370                 375                 380

Pro Ser Arg Asp Glu Leu Thr Arg Asn Gln Val Ser Leu Thr Cys Leu
385                 390                 395                 400

Val Lys Gly Phe Tyr Pro Ser Asp Ile Ala Val Glu Trp Glu Ser Asn
```

```
                         405                 410                 415
Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
            435                 440                 445

Trp Gln Gln Gly Asn Val Phe Ser Cys Ser Val Met His Glu Ala Leu
            450                 455                 460

His Asn His Tyr Thr Gln Lys Ser Leu Ser Leu Ser Pro Gly Gly Gly
465                 470                 475                 480

Gly Ala Cys Pro Gly His Ala
                485

<210> SEQ ID NO 34
<211> LENGTH: 487
<212> TYPE: PRT
<213> ORGANISM: Artificial Sequence
<220> FEATURE:
<223> OTHER INFORMATION: Synthetic

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser Gly Ser Thr Ser Gly Ser
            115                 120                 125

Gly Lys Pro Gly Ser Gly Glu Gly Ser Thr Lys Gly Glu Ile Val Leu
        130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Ser Val Ser Ser Tyr Leu Ala Trp Tyr
                165                 170                 175

Gln Gln Lys Pro Gly Gln Ala Pro Arg Leu Leu Ile Tyr Asp Ala Ser
            180                 185                 190

Asn Arg Ala Thr Gly Ile Pro Ala Arg Phe Ser Gly Ser Gly Ser Gly
        195                 200                 205

Thr Asp Phe Thr Leu Thr Ile Ser Ser Leu Glu Pro Glu Asp Phe Ala
    210                 215                 220

Val Tyr Tyr Cys Gln Gln Arg Ser Asn Trp Pro Pro Thr Phe Gly Gln
225                 230                 235                 240

Gly Thr Lys Val Glu Ile Lys Gly Gly Gly Ala Ser Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
```

```
                275                 280                 285
Pro Glu Val Thr Cys Val Val Asp Val Ser His Glu Asp Pro Glu
            290                 295                 300
Val Lys Phe Asn Trp Tyr Val Asp Gly Val Glu Val His Asn Ala Lys
305                 310                 315                 320
Thr Lys Pro Arg Glu Glu Gln Tyr Asn Ser Thr Tyr Arg Val Val Ser
                325                 330                 335
Val Leu Thr Val Leu His Gln Asp Trp Leu Asn Gly Lys Asp Tyr Lys
            340                 345                 350
Cys Lys Val Ser Asn Lys Ala Leu Pro Ala Pro Ile Glu Lys Thr Ile
                355                 360                 365
Ser Lys Ala Lys Gly Gln Pro Arg Glu Pro Gln Val Tyr Thr Leu Pro
370                 375                 380
Pro Ser Arg Asp Glu Leu Thr Arg Asn Gln Val Ser Leu Thr Cys Leu
385                 390                 395                 400
Val Lys Gly Phe Tyr Pro Ser Asp Ile Ala Val Glu Trp Glu Ser Asn
                405                 410                 415
Gly Gln Pro Glu Asn Asn Tyr Lys Thr Thr Pro Pro Val Leu Asp Ser
            420                 425                 430
Asp Gly Ser Phe Phe Leu Tyr Ser Lys Leu Thr Val Asp Lys Ser Arg
            435                 440                 445
Trp Gln Gln Gly Asn Val Phe Ser Cys Ser Val Met His Glu Ala Leu
            450                 455                 460
His Asn His Tyr Thr Gln Lys Ser Leu Ser Leu Ser Pro Gly Gly Gly
465                 470                 475                 480
Gly Ala Cys Pro Gly His Ala
                485

<210> SEQ ID NO 35
<211> LENGTH: 487
<212> TYPE: PRT
<213> ORGANISM: Artificial Sequence
<220> FEATURE:
<223> OTHER INFORMATION: Synthetic

<400> SEQUENCE: 35

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asn Trp Pro Pro
                85                  90                  95
Thr Phe Gly Gln Gly Thr Lys Val Glu Ile Lys Gly Ser Thr Ser Gly
            100                 105                 110
Ser Gly Lys Pro Gly Ser Gly Glu Gly Ser Thr Lys Gly Glu Val Gln
        115                 120                 125
Leu Leu Glu Ser Gly Gly Gly Leu Val Gln Pro Gly Gly Ser Leu Arg
    130                 135                 140
Leu Ser Cys Ala Val Ser Gly Phe Thr Phe Asn Ser Phe Ala Met Ser
```

```
            145                 150                 155                 160
    Trp Val Arg Gln Ala Pro Gly Lys Gly Leu Glu Trp Val Ser Ala Ile
                    165                 170                 175

Ser Gly Ser Gly Gly Gly Thr Tyr Tyr Ala Asp Ser Val Lys Gly Arg
                    180                 185                 190

Phe Thr Ile Ser Arg Asp Asn Ser Lys Asn Thr Leu Tyr Leu Gln Met
                    195                 200                 205

Asn Ser Leu Arg Ala Glu Asp Thr Ala Val Tyr Phe Cys Ala Lys Asp
    210                 215                 220

Lys Ile Leu Trp Phe Gly Glu Pro Val Phe Asp Tyr Trp Gly Gln Gly
    225                 230                 235                 240

Thr Leu Val Thr Val Ser Ser Gly Gly Ala Ser Asp Lys Thr His
                    245                 250                 255

Thr Cys Pro Pro Cys Pro Ala Pro Glu Leu Leu Gly Gly Pro Ser Val
                    260                 265                 270

Phe Leu Phe Pro Pro Lys Pro Lys Asp Thr Leu Met Ile Ser Arg Thr
                    275                 280                 285

Pro Glu Val Thr Cys Val Val Val Asp Val Ser His Glu Asp Pro Glu
                    290                 295                 300

Val Lys Phe Asn Trp Tyr Val Asp Gly Val Glu Val His Asn Ala Lys
    305                 310                 315                 320

Thr Lys Pro Arg Glu Glu Gln Tyr Asn Ser Thr Tyr Arg Val Val Ser
                    325                 330                 335

Val Leu Thr Val Leu His Gln Asp Trp Leu Asn Gly Lys Glu Tyr Lys
                    340                 345                 350

Cys Lys Val Ser Asn Lys Ala Leu Pro Ala Pro Ile Glu Lys Thr Ile
                    355                 360                 365

Ser Lys Ala Lys Gly Gln Pro Arg Glu Pro Gln Val Tyr Thr Leu Pro
                    370                 375                 380

Pro Ser Arg Asp Glu Leu Thr Arg Asn Gln Val Ser Leu Thr Cys Leu
    385                 390                 395                 400

Val Lys Gly Phe Tyr Pro Ser Asp Ile Ala Val Glu Trp Glu Ser Asn
                    405                 410                 415

Gly Gln Pro Glu Asn Asn Tyr Lys Thr Thr Pro Pro Val Leu Asp Ser
                    420                 425                 430

Asp Gly Ser Phe Phe Leu Tyr Ser Lys Leu Thr Val Asp Lys Ser Arg
                    435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Gly Gly
    465                 470                 475                 480

Gly Gly Cys Pro Gly His Ala
                    485

<210> SEQ ID NO 36
<211> LENGTH: 487
<212> TYPE: PRT
<213> ORGANISM: Artificial Sequence
<220> FEATURE:
<223> OTHER INFORMATION: Synthetic

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
```

```
                20                  25                  30
Ala Met Ser Trp Val Arg Gln Ala Pro Gly Lys Gly Leu Glu Trp Val
            35                  40                  45
Ser Ala Ile Ser Gly Ser Gly Gly Thr Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Phe Cys
                85                  90                  95
Ala Lys Asp Lys Ile Leu Trp Phe Gly Glu Pro Val Phe Asp Tyr Trp
            100                 105                 110
Gly Gln Gly Thr Leu Val Thr Val Ser Ser Gly Ser Thr Ser Gly Ser
            115                 120                 125
Gly Lys Pro Gly Ser Gly Glu Gly Ser Thr Lys Gly Glu Ile Val Leu
            130                 135                 140
Thr Gln Ser Pro Ala Thr Leu Ser Leu Ser Pro Gly Glu Arg Ala Thr
145                 150                 155                 160
Leu Ser Cys Arg Ala Ser Gln Ser Val Ser Ser Tyr Leu Ala Trp Tyr
                165                 170                 175
Gln Gln Lys Pro Gly Gln Ala Pro Arg Leu Leu Ile Tyr Asp Ala Ser
            180                 185                 190
Asn Arg Ala Thr Gly Ile Pro Ala Arg Phe Ser Gly Ser Gly Ser Gly
            195                 200                 205
Thr Asp Phe Thr Leu Thr Ile Ser Ser Leu Glu Pro Glu Asp Phe Ala
            210                 215                 220
Val Tyr Tyr Cys Gln Gln Arg Ser Asn Trp Pro Pro Thr Phe Gly Gln
225                 230                 235                 240
Gly Thr Lys Val Glu Ile Lys Gly Gly Gly Ala Ser Asp Lys Thr His
                245                 250                 255
Thr Cys Pro Pro Cys Pro Ala Pro Glu Leu Leu Gly Gly Pro Ser Val
            260                 265                 270
Phe Leu Phe Pro Pro Lys Pro Lys Asp Thr Leu Met Ile Ser Arg Thr
            275                 280                 285
Pro Glu Val Thr Cys Val Val Val Asp Val Ser His Glu Asp Pro Glu
            290                 295                 300
Val Lys Phe Asn Trp Tyr Val Asp Gly Val Glu Val His Asn Ala Lys
305                 310                 315                 320
Thr Lys Pro Arg Glu Glu Gln Tyr Asn Ser Thr Tyr Arg Val Val Ser
                325                 330                 335
Val Leu Thr Val Leu His Gln Asp Trp Leu Asn Gly Lys Glu Tyr Lys
            340                 345                 350
Cys Lys Val Ser Asn Lys Ala Leu Pro Ala Pro Ile Glu Lys Thr Ile
            355                 360                 365
Ser Lys Ala Lys Gly Gln Pro Arg Glu Pro Gln Val Tyr Thr Leu Pro
            370                 375                 380
Pro Ser Arg Asp Glu Leu Thr Arg Asn Gln Val Ser Leu Thr Cys Leu
385                 390                 395                 400
Val Lys Gly Phe Tyr Pro Ser Asp Ile Ala Val Glu Trp Glu Ser Asn
                405                 410                 415
Gly Gln Pro Glu Asn Asn Tyr Lys Thr Thr Pro Pro Val Leu Asp Ser
            420                 425                 430
Asp Gly Ser Phe Phe Leu Tyr Ser Lys Leu Thr Val Asp Lys Ser Arg
            435                 440                 445
```

```
Trp Gln Gln Gly Asn Val Phe Ser Cys Ser Val Met His Glu Ala Leu
        450                 455                 460

His Asn His Tyr Thr Gln Lys Ser Leu Ser Leu Ser Pro Gly Gly Gly
465                 470                 475                 480

Gly Gly Cys Pro Gly His Ala
                485

<210> SEQ ID NO 37
<211> LENGTH: 47
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 2
<223> OTHER INFORMATION: 2-aminoisobutyric acid

<400> SEQUENCE: 37

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gly Gly Ser Gly Gly Gly Gly Ser Gly Gly Gly Gly Ser Gly Cys
        35                  40                  45

<210> SEQ ID NO 38
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 7
<223> OTHER INFORMATION: D-form
<220> FEATURE:
<221> NAME/KEY: VARIANT
<222> LOCATION: 10
<223> OTHER INFORMATION: D-form

<400> SEQUENCE: 38

Cys Ser Gly Gly Gly Gly Phe Cys Phe Trp Lys Thr Cys Thr
1               5                   10

<210> SEQ ID NO 39
<211> LENGTH: 46
<212> TYPE: PRT
<213> ORGANISM: Artificial Sequence
<220> FEATURE:
<223> OTHER INFORMATION: Synthetic

<400> SEQUENCE: 39

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

Gly Gly Gly Ser Gly Gly Gly Ser Ala Cys Pro Gly His Ala
        35                  40                  45

<210> SEQ ID NO 40
<211> LENGTH: 55
<212> TYPE: PRT
<213> ORGANISM: Artificial Sequence
<220> FEATURE:
```

<223> OTHER INFORMATION: Synthetic

<400> SEQUENCE: 40

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Gly Gly Gly Gly Ser Gly Gly Gly Gly Ser Gly Gly Gly Gly
        35                  40                  45

Ser Ala Cys Pro Gly His Ala
    50                  55

<210> SEQ ID NO 41
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Pyroglutamate
<220> FEATURE:
<221> NAME/KEY: VARIANT
<222> LOCATION: 6
<223> OTHER INFORMATION: D-form

<400> SEQUENCE: 41

Xaa His Trp Ser Trp Leu Leu Arg Pro Gly Gly Ser Gly Ser Gly Gly
1               5                   10                  15

Ser Gly Cys Gly Gly His Ala
            20

<210> SEQ ID NO 42
<211> LENGTH: 18
<212> TYPE: PRT
<213> ORGANISM: Artificial Sequence
<220> FEATURE:
<223> OTHER INFORMATION: Synthetic

<400> SEQUENCE: 42

Glu Gly Glu Gly Glu Ala Gly Gly Lys Gly Ala Gly Lys Gly Ala Gly
1               5                   10                  15

Lys Gly

<210> SEQ ID NO 43
<211> LENGTH: 18
<212> TYPE: PRT
<213> ORGANISM: Artificial Sequence
<220> FEATURE:
<223> OTHER INFORMATION: Synthetic

<400> SEQUENCE: 43

Glu Asp Glu Asp Glu Ala Gly Gly Lys Gly Ala Gly Lys Gly Ala Gly
1               5                   10                  15

Lys Gly

<210> SEQ ID NO 44
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 6,8
<223> OTHER INFORMATION: Xaa is PEGylated amino acid with four EG units

<400> SEQUENCE: 44

Glu Gly Glu Gly Glu Xaa Lys Xaa Lys
1               5

<210> SEQ ID NO 45
<211> LENGTH: 12
<212> TYPE: PRT
<213> ORGANISM: Artificial Sequence
<220> FEATURE:
<223> OTHER INFORMATION: Synthetic

<400> SEQUENCE: 45

Lys Gly Ala Gly Gly Lys Gly Ala Gly Gly Lys Gly
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic

<400> SEQUENCE: 46

Glu Gly Glu Gly Glu Ala Gly Lys Gly Ala Gly
1               5                   10

<210> SEQ ID NO 47
<211> LENGTH: 144
<212> TYPE: PRT
<213> ORGANISM: Artificial Sequence
<220> FEATURE:
<223> OTHER INFORMATION: Synthetic

<400> SEQUENCE: 47

Ala Cys Pro Gly His Ala Gly Gly Gly Ser Ala Pro Thr Ser Ser
1               5                   10                  15

Ser Thr Lys Lys Thr Gln Leu Gln Leu Glu His Leu Leu Asp Leu
                20                  25                  30

Gln Met Ile Leu Asn Gly Ile Asn Asn Tyr Lys Asn Pro Lys Leu Thr
            35                  40                  45

Arg Met Leu Thr Phe Lys Phe Tyr Met Pro Lys Lys Ala Thr Glu Leu
        50                  55                  60

Lys His Leu Gln Cys Leu Glu Glu Leu Lys Pro Leu Glu Glu Val
65                  70                  75                  80

Leu Asn Leu Ala Gln Ser Lys Asn Phe His Leu Arg Pro Arg Asp Leu
                85                  90                  95

Ile Ser Asn Ile Asn Val Ile Val Leu Glu Leu Lys Gly Ser Glu Thr
            100                 105                 110

Thr Phe Met Cys Glu Tyr Ala Asp Glu Thr Ala Thr Ile Val Glu Phe
        115                 120                 125

Leu Asn Arg Trp Ile Thr Phe Ser Gln Ser Ile Ile Ser Thr Leu Thr
    130                 135                 140

COMPOSITE POLYPEPTIDE HAVING A METAL BINDING MOTIF AND MOLECULAR CONSTRUCT COMPRISING THE SAME

CROSS-REFERENCE TO RELATED APPLICATION

This application relates to and claims the benefit of US Provisional Application No. 62/823,626, filed Mar. 25, 2019, the content of the application is incorporated herein by reference in its entirety.

BACKGROUND OF THE INVENTION

1. Field of the Invention

The present disclosure relates to composite polypeptides having a metal binding motif, which is a short oligopeptide capable of forming a complex with a zinc cation.

2. Description of Related Art

Bioconjugation is a technique used to form a covalent link between a biomolecule and another molecule, which may or may not be a biomolecule. Biomolecules refer generally to molecules present in organisms and essential to the biological process. Biomolecules include natural and synthetic polypeptides or proteins, carbohydrates, lipids, nucleic acids, and metabolites.

The concept of arming antibodies or antibody fragments with toxins (i.e., antibody-toxin conjugates or "ATCs"), cytotoxic drugs (i.e., antibody-drug conjugates or "ADCs"), and radionuclides (i.e., antibody-radionuclide conjugates or "ARCs") germinated in the 1970s. Synthesis of such bioconjugates often involves conjugation reactions, such as coupling of surface-accessible lysine, cysteine or tyrosine residues, and modification of surface-accessible lysine or tryptophan residues or the N- and C-terminus. Nonetheless, the above-mentioned amino acid residues are abundant in the parent antibody, and the conjugation reaction is typically a random process. As a consequence, the conjugation reaction lacks chemoselectivity and efficiency, and often results in heterogenous products. For example, a prior research on huN901-DM1, a maytansinoid-monoclonal antibody immunoconjugate, reveals that the lysine-conjugated ADC sample has ADCs with different drug-to-antibody rations (DARs) ranging from 0 to 6 and potentially contains more than 4.5 million unique molecules.

In view of the foregoing, there is an increasing need for conjugation strategies that can effectively conjugate a functional element to a specific site of a biomolecule, particularly, a peptide-based molecule. The present invention is believed to be an answer to that need.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a metal binding motif, which is capable of forming a complex with a zinc ion under suitable conditions.

According to one embodiment of the present disclosure, the metal binding motif comprising the amino acid sequence of $CX_1X_2HA$ (SEQ ID NO: 1) in the order from N-terminus to C-terminus, or in the order from C-terminus to N-terminus, where $X_1$ is glycine or proline, and $X_2$ is glycine or alanine, and the metal binding motif is located at the N- or C-terminus of the parent polypeptide. Illustrative examples of the metal binding motif include, but are not limited to, CGGHA (SEQ ID NO: 2), CPGHA (SEQ ID NO: 3), CGAHA (SEQ ID NO: 4), CPAHA (SEQ ID NO: 5), GCGGHA (SEQ ID NO: 6), ACPGHA (SEQ ID NO: 7), and GCPGHA (SEQ ID NO: 8).

In another aspect, the present disclosure is directed to a composite polypeptide that comprises the metal binding motif according to the above-mentioned aspect/embodiments. The composite polypeptide is thus capable of forming a complex with a metal ion (e.g., zinc ion) via the metal binding motif under suitable conditions. In this way, the sulfhydryl group of the cysteine residue in complex with the metal ion is more reactive than the sulfhydryl group of a cysteine residue without being complexed with the metal ion. As could be appreciated, said complex can be subject to chemical conjugation with another chemical entity or biomolecule in a site-specific manner, thereby forming a bioconjugate.

According to one embodiment of the present disclosure, the composite polypeptide comprises a parent polypeptide and a metal binding motif located at the N- or C-terminus of the parent polypeptide. In some optional examples, there is an intervening sequence of 1 to 10 glycine residues between the parent polypeptide and the metal binding motif, whereas in other examples, the present metal binding motif precedes or follows the parent polypeptide directly.

In yet another aspect, one or more functional elements can be covalently conjugated with the composite polypeptide according to the above aspect/embodiments of the present disclosure by reacting with the sulfhydryl (SH) group of the cysteine residue in the metal binding motif of the composite polypeptide, thereby forming a molecular construct (or bioconjugate).

According to optional embodiments of the present disclosure, the SH-reactive group is maleimide, iodoacetyl, bromoacetyl, vinyl sulfone, mono-sulfone, methylsulfonyl benzothiazole, or 2-pyridyldithiol group.

In some optional embodiments, the composite polypeptide is in a dimer form; for example, the composite polypeptide may comprise part of Fc region, F(ab')$_2$, or antibody. In these cases, each composite polypeptide chain has one functional element conjugated thereto.

According to various embodiments of the present disclosure, the functional element is a small molecule entity capable of eliciting a therapeutic effect. For example, the small molecule entity may be a cytotoxic drug, a toll-like receptor agonist, or a chelator complexed with a radioactive nuclide. Alternatively, the functional element is a fatty acid chain capable of modifying the pharmacokinetic profile of parent polypeptide or the molecular construct as a whole.

Alternatively, the functional element is in a form of a linker unit (also referred to as a "bundle"). According to certain embodiments of the present invention, the linker unit comprises a center core and a plurality of targeting, effector or pharmacokinetic elements.

Specifically, the center core comprises, 2 to 10 lysine (K) residues. Any two of the K residues are adjacent to each other or are separated by a filler. In some cases, the SH-reactive group is linked to the first or last K residue of the center core by forming an amide bond therewith. In other cases, the center core further comprises a terminal spacer, and the SH-reactive group is linked to the terminal amino acid residue of the terminal spacer by forming an amide bond therewith. The terminal spacers mat be an N-terminal spacer linked to the N-terminus of the first K residue or a C-terminal spacer linked to the C-terminus of the last K residue. Each of the filler and the terminal spacer comprises, independently, (1) 1 to 12 non-K amino acid residues, or (2) a PEGylated amino acid having 1 to 12 repeats of ethylene glycol (EG) unit.

According to some embodiments of the present disclosure, the center core carries a local negative charge at or near the amino acid residue linked with the SH-reactive group. For example, the local negative charge is present within the first 5 to 15 amino acid residues within the amino acid residue starting from the amino acid residue linked with the SH-reactive group. Specifically, the local negative charge is present within the first 5, 6, 7, 8, 9, 10, 11, 12, 13, 14, or amino acid residues starting from the amino acid residue linked with the SH-reactive group. The local negative charge can be imparted by including one or more negatively-charged amino acid residues at pH=7, such as aspartate (D) and glutamate (E) residue. Alternatively, the core may be conjugated with a plurality of effector elements that are negatively charged.

In some examples, each targeting, effector or pharmacokinetic element is linked to the K residue of the core via forming an amide bond with the ε-amino group of the K residue. In some other cases, the molecular construct further comprises 2 to 10 linking arms, wherein one terminus of each linking arm is linked to the K residue of the core via forming an amide bond with the ε-amino group of the K residue, and the other terminus of each linking arm is linked to each targeting, effector or pharmacokinetic element. For example, the linking arm can be a peptide comprising 2-12 non-K amino acid residues, or a polyethylene glycol (PEG) chain having 2-24 repeats of EG units.

According to some embodiments of the present invention, the composite polypeptide described above serves as a targeting element capable of directing the molecular construct to the site of interest or to increase the relative level of the molecular construct at the site of interest. In these cases, the linker unit (or bundle) may carry a plurality of effector elements, such as the small molecule entity described above.

According to some embodiments of the present invention, the composite polypeptide described above serves as an effector element capable of eliciting the desired therapeutic effect in a subject. In these cases, the linker unit (or bundle) may carry a plurality of pharmacokinetic elements, such as a $C_{2-28}$ fatty acid derivative or $C_{8-28}$ dioic fatty acid derivative, so as to modify or optimize the pharmacokinetic profile of the molecular construct or the composite polypeptide in a subject. According to various embodiments of the present invention, the ε-amino group of the K residue is linked with the $C_{2-28}$ fatty acid derivative or $C_{8-28}$ dioic fatty acid derivative. The fatty acid molecules can associate with serum albumin and hence improve the kinetic properties of the modified parent polypeptide in vivo.

Further also within the scope of the present invention is linker unit described above, which is capable of forming a molecular construct with the present composite polypeptide.

In yet another aspect, the present invention is directed to a linker unit capable of carrying a plurality of composite polypeptides according to above-mentioned aspect/embodiments of the present disclosure. According to embodiments of the present disclosure, the linker unit having a plurality of composite polypeptides covalently linked to the center core thereof are sometime referred to as polypeptide bundles.

According to certain embodiments of the present invention, the present linker unit comprises a center core and a plurality of linking arms.

Specifically, the center core comprises, 2 to 10 lysine (K) residues and a conjugating group. Any two of the K residues are adjacent to each other or are separated by a filler. In some cases, the conjugating group is linked to the first or last K residue of the center core by forming an amide bond therewith. Examples of the conjugating group include, but are not limited to, azide, alkyne, tetrazine, cyclooctene and cyclooctyne groups. In other cases, the center core further comprises a terminal spacer, and the SH-reactive group is linked to the terminal amino acid residue of the terminal spacer by forming an amide bond therewith. The terminal spacers mat be an N-terminal spacer linked to the N-terminus of the first K residue or a C-terminal spacer linked to the C-terminus of the last K residue. Each of the filler and the terminal spacer comprises, independently, (1) 1 to 12 non-K amino acid residues, or (2) a PEGylated amino acid having 1 to 12 repeats of ethylene glycol (EG) unit.

According to some embodiments, one terminus of each linking arm is linked to the K residue of the core via forming an amide bond with the ε-amino group of the K residue, whereas the other terminus of each linking arm has a SH-reactive group. For example, the linking arm can be a peptide comprising 2-12 non-K amino acid residues, or a polyethylene glycol (PEG) chain having 2-24 repeats of EG units.

According to some embodiments of the present invention, the linker unit further comprises 2 to 10 composite polypeptides according to above-mentioned aspect/embodiments and a functional element. Each composite polypeptide is conjugated to the thiol group of the cysteine residue in the metal binding motif via SH-reactive crosslinking chemistry.

According to some optional embodiments of the present invention, each linking arm carries a local negative charge at or near the amino acid residue linked with the SH-reactive group. Specifically, the local negative charge is present within the first 5 to 15 amino acid residues within the amino acid residue starting from the amino acid residue linked with the SH-reactive group. For example, the local negative charge is present within the first 5, 6, 7, 8, 9, 10, 11, 12, 13, 14, or 15 amino acid residues starting from the amino acid residue linked with the SH-reactive group. The local negative charge can be imparted by including one or more negatively-charged amino acid residues at pH=7, such as aspartate (D) and glutamate (E) residue.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIG. 37 is a schematic diagram showing the structure of the Cys-PSMA ligand according to one working example of the present invention;

FIG. 38 shows the ESI-MS result of the Cys-PSMA ligand according to one working example of the present invention;

FIG. 39 is a schematic diagram showing the structure of the calcitonin-MBM-1 according to one working example of the present invention;

DESCRIPTION

Figure 1:
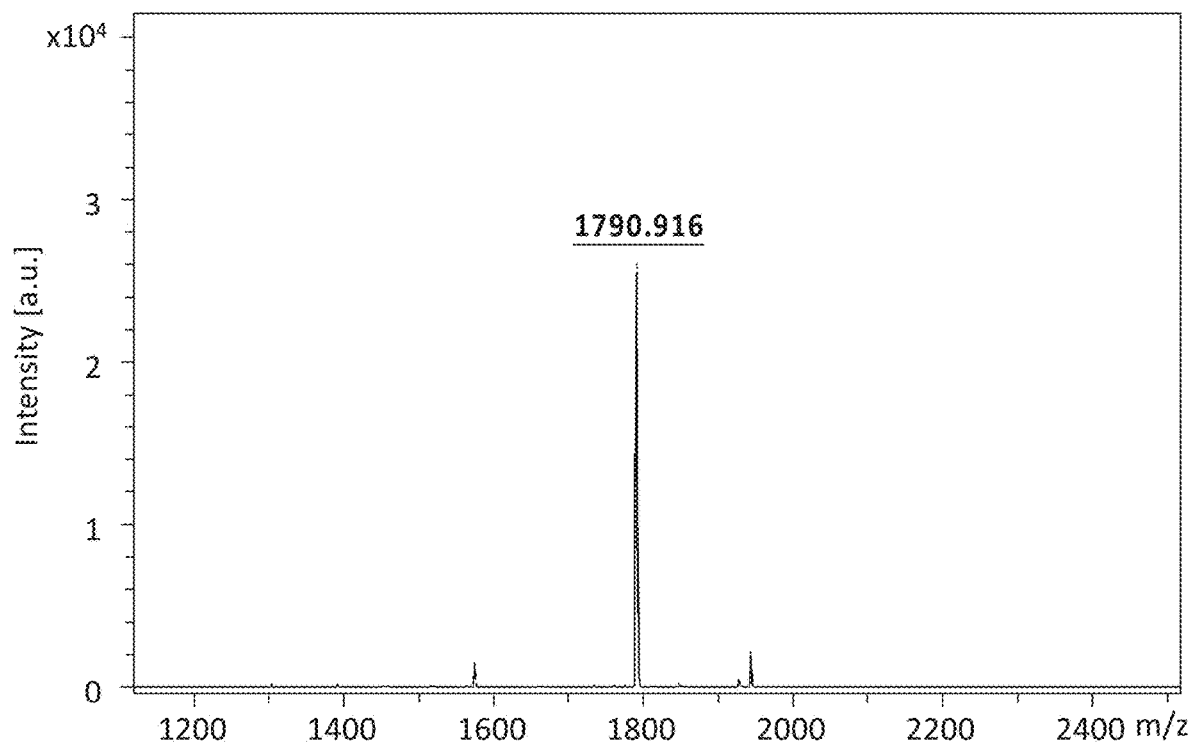
FIG. 1 is the MALDI-TOF result of the Mal-Peptide 1 center core according to one working example of the present invention.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Also, as used herein and in the claims, the terms "at least one" and "one or more" have the same meaning and include one, two, three, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

As used herein, the term "targeting element" refers to the portion of a molecular construct that directly or indirectly binds to a target of interest (e.g., a receptor on a cell surface or a protein in a tissue) thereby facilitates the transportation of the present molecular construct into the interested target. In some example, the targeting element may direct the molecular construct to the proximity of the target cell. In other cases, the targeting element specifically binds to a molecule present on the target cell surface or to a second molecule that specifically binds a molecule present on the cell surface. In some cases, the targeting element may be internalized along with the present molecular construct once it is bound to the interested target, hence is relocated into the cytosol of the target cell. A targeting element may be an antibody or a ligand for a cell surface receptor, or it may be a molecule that binds such antibody or ligand, thereby indirectly targeting the present molecular construct to the target site (e.g., the surface of the cell of choice). The localization of the effector (therapeutic agent) in the diseased site will be enhanced or favored with the present molecular constructs as compared to the therapeutic without a targeting function. The localization is a matter of degree or relative proportion; it is not meant for absolute or total localization of the effector to the diseased site.

According to the present invention, the term "effector element" refers to the portion of a molecular construct that elicits a biological activity (e.g., inducing or suppressing immune activities, exerting cytotoxic effects, inhibiting enzymes, and the like) or other functional activity (e.g., recruiting immunocytes or other therapeutic molecules), once the molecular construct is directed to its target site. The "effect" can be therapeutic or diagnostic. The effector elements encompass those that bind to cells and/or extracellular immunoregulatory factors. The effector element comprises agents such as proteins, nucleic acids, lipids, carbohydrates, glycopeptides, drug moieties (both small molecule drug and biologics), compounds, elements, and isotopes, and fragments thereof.

According to the present invention, "a pharmacokinetic element" intends to mean an element capable of modifying at least one of the following characteristics of the molecular construct: the solubility, clearance, half-life, and bioavailability. For example, the pharmacokinetic element may comprise a long PEG chain having a molecular weight of about 20,000 to 50,000 daltons. Alternatively, the pharmacokinetic element may comprise a $C_{8-28}$ fatty acid chain or a $C_{8-28}$ dioic fatty acid chain.

The term "bioconjugate" according to the present invention refers to a molecular construct comprising the composite polypeptide of the present invention and one or more functional elements.

Although the terms, first, second, third, etc. may be used herein to describe various elements, components, regions, and/or sections, these elements (as well as components, regions, and/or sections) are not to be limited by these terms. Also, the use of such ordinal numbers does not imply a sequence or order unless clearly indicated by the context. Rather, these terms are simply used to distinguish one element from another. Thus, a first element, discussed below, could be termed a second element without departing from the teachings of the exemplary embodiments.

Here, the terms "link," "couple," and "conjugate" are used interchangeably to refer to any means of connecting two components either via direct linkage or via indirect linkage between two components.

The term "polypeptide" as used herein refers to a polymer having at least two amino acid residues. Typically, the polypeptide comprises amino acid residues ranging in length from 2 to about 200 residues; nonetheless, it also encompasses macromolecules that has more than 200 amino acid residues. Where an amino acid sequence is provided herein, L-, D-, or beta amino acid versions of the sequence are also contemplated. Polypeptides also include amino acid polymers in which one or more amino acid residues are an artificial chemical analogue of a corresponding naturally occurring amino acid, as well as to naturally occurring amino acid polymers. In addition, the term applies to amino acids joined by a peptide linkage or by other, "modified linkages," e.g., where the peptide bond is replaced by an α-ester, a β-ester, a thioamide, phosphoramide, carbomate, hydroxylate, and the like.

In certain embodiments, conservative substitutions of the amino acids comprising any of the sequences described herein are contemplated. In various embodiments, one, two, three, four, or five different residues are substituted. The term "conservative substitution" is used to reflect amino acid substitutions that do not substantially alter the activity (e.g., biological or functional activity and/or specificity) of the molecule. Typically, conservative amino acid substitutions involve substitution one amino acid for another amino acid with similar chemical properties (e.g., charge or hydrophobicity). Certain conservative substitutions include "analog substitutions" where a standard amino acid is replaced by a non-standard (e.g., rare, synthetic, etc.) amino acid differing minimally from the parental residue. Amino acid analogs are derived synthetically from the standard amino acids without sufficient change to the structure of the parent, are isomers, or are metabolite precursors. In the present application, the amino acid residues (1) lysine, which contains an amine group in its sidechain, (2) cysteine, which contains a thiol group in its sidechain, (3) serine and threonine, which contain a hydroxyl group in their sidechain, and (4) aspartic acid and glutamic acid, which contain a carboxyl group in their sidechain, are considered four distinctive groups of amino acids. These four groups of amino acids each contain in their sidechains a unique functional group, which may be applied for conjugating to various chemical components. Non-natural amino acids, which contain the same functional groups in the sidechains may be substituted for similar purposes.

In certain embodiments, polypeptides comprising at least 80%, preferably at least 85% or 90%, and more preferably at least 95% or 98% sequence identity with any of the sequences described herein are also contemplated.

"Percentage (%) amino acid sequence identity" with respect to the polypeptide sequences identified herein is defined as the percentage of polypeptide residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two polypeptide sequences was carried out by computer program Blastp (protein-protein BLAST) provided online by Nation Center for Biotechnology Information (NCBI). The percentage amino acid sequence identity of a given polypeptide sequence A to a given polypeptide sequence B (which can alternatively be phrased as a given polypeptide sequence A that has a certain % amino acid sequence identity to a given polypeptide sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

The term "PEGylated amino acid" as used herein refers to a polyethylene glycol (PEG) chain with one amino group and one carboxyl group. Generally, the PEGylated amino acid has the formula of $NH_2-(CH_2CH_2O)_n-CO_2H$. In the present disclosure, the value of n ranges from 1 to 20; preferably, ranging from 2 to 12.

The term "conjugating moiety" as used herein refers to a molecule having one or more functional group (also referred to as a "conjugating group"), which is chemically reactive and is capable of binding covalently to other chemical units. Non-limiting examples of the functional group include, hydroxyl, carbonyl, carboxyl, thiol, amine, tert-Butyldimethylsilyl (TBDMS), N-hydroxysuccinimidyl (NHS), SH-reactive group (e.g., maleimide, haloacetyl, sulfone, or pyridyl disulfide), iodo, iodoacetamide azide, alkyne, tetrazine, cyclooctene, and cyclooctyne groups. According to embodiments of the present disclosure, the conjugating moiety of the present molecular construct has two functional groups, in which one is a carboxyl or amine group for binding with the alpha-amino or carboxyl group of the terminal amino acid residue of the core via forming an amide bond therebetween so that the conjugating moiety is bonded to the N- or C-terminal amino acid residue of the core; and the other is an SH-reactive group for binding with the second element via the SH-reactive crosslinking chemistry.

As used herein, the term "terminus" with respect to a polypeptide refers to an amino acid residue at the N- or C-end of the polypeptide. Regarding a polymer, the term "terminus" refers to a constitutional unit of the polymer (e.g., the polyethylene glycol of the present disclosure) that is positioned at the end of the polymeric backbone. In the present specification and claims, the term "free terminus" is used to mean the terminal amino acid residue or constitutional unit is not chemically bound to any other molecular.

The term "antigen" or "Ag" are interchangeably used and refers to a molecule that elicits an immune response. This immune response may involve a secretory, humoral and/or cellular antigen-specific response. In the present disclosure, the term "antigen" can be any of a protein, a polypeptide (including mutants or biologically active fragments thereof), a polysaccharide, a glycoprotein, a glycolipid, a nucleic acid, or a combination thereof.

In the present specification and claims, the term "antibody" or "antibody fragment" is used in the broadest sense and covers fully assembled antibodies, antibody fragments that bind with antigens, such as antigen-binding fragment (Fab/Fab'), F(ab')2 fragment (having two antigen-binding Fab portions linked together by disulfide bonds), variable fragment (Fv), single chain variable fragment (scFv), bi-specific single-chain variable fragment (bi-scFv), nanobodies (also referred to as single-domain antibodies, sdAb), unibodies and diabodies. "Antibody fragments" comprise a portion of an intact antibody, preferably the antigen-binding region or variable region of the intact antibody. An antibody fragment may comprise a pair of scFv fused to the N- or C-terminal of a pair of CH2-CH3 segments derived from human γ4 or γ1 immunoglobulin. Typically, an "antibody" refers to a protein consisting of one or more polypeptides substantially encoded by immunoglobulin genes or fragments of immunoglobulin genes. The well-known immunoglobulin genes include the kappa, lambda, alpha, gamma, delta, epsilon, and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. A typical immunoglobulin (antibody) structural unit is known to comprise a tetramer. Each tetramer is composed of two identical pairs of polypeptide chains, with each pair having one "light" chain (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain (VH) refer to these light and heavy chains, respectively. According to embodiments of the present disclosure, the antibody fragment can be produced by modifying the nature antibody or by de novo synthesis using recombinant DNA methodologies. In certain embodiments of the present disclosure, the antibody and/or antibody fragment can be bispecific, and can be in various configurations. For example, bispecific antibodies may comprise two different antigen binding sites (variable regions). In various embodiments, bispecific antibodies can be produced by hybridoma technique or recombinant DNA technique. In certain embodiments, bispecific antibodies have binding specificities for at least two different epitopes. In many of the molecular configurations that employ antibody fragments, the antibody fragments may be substituted for antibody mimetics, which bind to the same antigenic components as the antibody fragments. Antibody mimetics include anticalins, DARPins, affibodies, filomers, ankyrins, avimers, and others.

The term "specifically binds" as used herein, refers to the ability of an antibody or an antigen-binding fragment thereof, to bind to an antigen with a dissociation constant (Kd) of no more than about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, and/or to bind to an antigen with an affinity that is at least two-folds greater than its affinity to a nonspecific antigen.

The term "treatment" as used herein includes preventative (e.g., prophylactic), curative or palliative treatment; and "treating" as used herein also includes preventative (e.g., prophylactic), curative or palliative treatment. In particular, the term "treating" as used herein refers to the application or administration of the present molecular construct or a pharmaceutical composition comprising the same to a subject, who has a medical condition a symptom associated with the medical condition, a disease or disorder secondary to the medical condition, or a predisposition toward the medical condition, with the purpose to partially or completely alleviate, ameliorate, relieve, delay onset of, inhibit progression of, reduce severity of, and/or reduce incidence of one or more symptoms or features of said particular disease, disorder, and/or condition. Treatment may be administered to a subject who does not exhibit signs of a disease, disorder, and/or condition, and/or to a subject who exhibits only early signs of a disease, disorder and/or condition, for the purpose of decreasing the risk of developing pathology associated with the disease, disorder and/or condition.

The term "effective amount" as used herein refers to the quantity of the present molecular construct that is enough to yield a desired therapeutic response. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as particular condition being treated, the physical condition of the patient (e.g., the patient's body mass, age, or gender), the type of subject being treated, the duration of the treatment, the nature of concurrent therapy (if any), and the specific formulations employed and the structure of the compounds or its derivatives. Effective amount may be expressed, for example, as the total mass of active component (e.g., in grams, milligrams or micrograms) or a ratio of mass of active component to body mass, e.g., as milligrams per kilogram (mg/kg).

The terms "application" and "administration" are used interchangeably herein to mean the application of a molecular construct or a pharmaceutical composition of the present invention to a subject in need of a treatment thereof.

The terms "subject" and "patient" are used interchangeably herein and are intended to mean an animal including the human species that is treatable by the molecular construct, pharmaceutical composition, and/or method of the present invention. The term "subject" or "patient" intended to refer to both the male and female gender unless one gender is specifically indicated. Accordingly, the term "subject" or "patient" comprises any mammal, which may benefit from the treatment method of the present disclosure. Examples of a "subject" or "patient" include, but are not limited to, a human, rat, mouse, guinea pig, monkey, pig, goat, cow, horse, dog, cat, bird and fowl. In an exemplary embodiment, the patient is a human. The term "mammal" refers to all members of the class Mammalia, including humans, primates, domestic and farm animals, such as rabbit, pig, sheep, and cattle; as well as zoo, sports or pet animals; and rodents, such as mouse and rat. The term "non-human mammal" refers to all members of the class Mammals except human.

According to various embodiments of the present invention, the term "metal binding motif" refers to a short oligopeptide capable of binding a metal ion, such as $Zn^{2+}$, $Ni^{2+}$, $Co^{2+}$, $Fe^{2+}$, $Mn^{2+}$, or $Cu^{2+}$. In some embodiments, the metal binding motifs capable of binding a zinc ion is also referred to as "zinc binding motifs;" nonetheless, as could be appreciated by persons having ordinary skill in the art, such tags may also bind with other metal ions with physical and/or chemical properties similar to the zinc ion.

The present disclosure is based, at least on the design of several novel metal binding motifs that can be fused to the N- or C-terminus of a parent polypeptide. The present metal binding motifs are advantageous for the construction of bioconjugates in several aspects. First, the present metal binding motifs are sequences of human origin, and thus, they are less immunogenic compared with conventional metal binding motifs that are not part of the human genome. Second, the expression yield of the composite polypeptides having the present metal binding motifs are desirable, and the thus-expressed composite polypeptides are quite stable during the storage, conjugation, and purification processes. Third, the present metal binding motifs allows for a facile site-specific conjugation reaction between the SH group of the cysteine residue of the metal binding motif and the SH-reactive group of a functional element under a condition in which the cysteine residues of the parent polypeptide are mostly inactive. Accordingly, the present invention delivers a versatile means for constructing multifunctional bioconjugates. Aspects and embodiments of the present invention are provided below.

(I) Metal Binding Motif

The first aspect of the present disclosure is directed to a metal binding motif, which, under a suitable condition, can form a complex with a metal ion, such as $Zn^{2+}$, $Ni^{2+}$, $Co^{2+}$, $Fe^{2+}$, $Mn^{2+}$, or $Cu^{2+}$.

According to one embodiment of the present disclosure, the metal binding motif comprising the amino acid sequence of $CX_1X_2HA$ (SEQ ID NO: 1) in the order from N-terminus to C-terminus, or in the order from C-terminus to N-terminus, where $X_1$ is glycine or proline, and $X_2$ is glycine or alanine. Illustrative examples of the metal binding motif include, but are not limited to, CGGHA (SEQ ID NO: 2), CPGHA (SEQ ID NO: 3), CGAHA (SEQ ID NO: 4), CPAHA (SEQ ID NO: 5), GCGGHA (SEQ ID NO: 6), ACPGHA (SEQ ID NO: 7), and GCPGHA (SEQ ID NO: 8).

(II) Composite Polypeptide Containing Metal Binding Motif

In another aspect, the present disclosure is directed to a composite polypeptide that comprises the metal binding motif according to the above-mentioned aspect/embodiments. The composite polypeptide is thus capable of forming a complex with a metal ion via the metal binding motif under suitable condition.

According to one embodiment of the present disclosure, the composite polypeptide comprises a parent polypeptide and a metal binding motif according to above aspect/embodiments of the present invention. In various embodiments, metal the binding motif is fused to the N- or C-terminus of the parent polypeptide, directly or with one or more intervening amino acid residues. In optional embodiments, the intervening sequence may have two to ten glycine residues According to various embodiments of the present disclosure, when the metal binding motif located at the N-terminus of the parent polypeptide, the metal binding motif may have the sequence $CX_1X_2HA$ (SEQ ID NO: 1) in the order from N-terminus to C-terminus, or in the order from C-terminus to N-terminus, where $X_1$ is glycine or proline, and $X_2$ is glycine or alanine. Similarly, when the metal binding motif located at the C-terminus of the parent polypeptide, the metal binding motif may have the sequence of $CX_1X_2HA$ (SEQ ID NO: 1) in the order from N-terminus to C-terminus, or in the order from C-terminus to N-terminus, where $X_1$ is glycine or proline, and $X_2$ is glycine or alanine.

According to various embodiments of the present disclosure, the parent polypeptide may be a peptide hormone or equivalents thereof. Equivalents of peptide hormones include functional fragments, precursors, analogues or derivatives that are known to persons having ordinary skill in the art. Non-limiting examples of peptide hormones suitable for use herein include, adrenocorticotropic hormone (ACTH), amylin, angiotensin, atrial natriuretic peptide (ANP), C-type natriuretic peptide (CNP), calcitonin, cholecystokinin (CCK), gastrin, ghrelin, glucagon, growth hormone, follicle-stimulating hormone (FSH), insulin, leptin, melanocyte-stimulating hormone (MSH), oxytocin, parathyroid hormone (PTH), prolactin, renin, somatostatin, thyroid-stimulating hormone (TSH), thyrotropin-releasing hormone (TRH), vasopressin, and vasoactive intestinal peptide. For example, equivalents of insulin include, but are not limited to, lispro, aspart, glulisine, detemir, degludec, and glargine. Equivalents of calcitonin include, but are not limited to, procalcitonin and adrenomedullin. Equivalents of somatostatin include, but are not limited to, octreotide and lanreotide.

In certain embodiments, the parent polypeptide may be a peptidomimetic ligand that binds to cell-surface receptors. Peptidomimetics are small protein-like chains designed to mimic a peptide. For example, a series of glutamate-urea-lysine based peptidomimetics with PSMA-binding affinity have been designed.

In optional embodiments, the parent polypeptide may be an antibody, such as a monoclonal antibody, immunoglobulin A (IgA), IgD, IgE, IgG, or IgM. Functional fragments or derivatives of a whole antibody is also covered by the scope of the present disclosure, and examples of which include, but are not limited to, bispecific antibodies, chimeric antibodies, human antibodies humanized antibodies, single-chain antibodies (scAbs), single chain variable fragments (scFvs), tandem di-scFvs, tandem tri-scFvs, diabodies, triabodies, tetrabodies, Fab fragments, F(ab')2 fragments, Fds, domain antibodies, and minibodies.

Alternatively, the parent polypeptide may be a cytokine or equivalents thereof. Equivalents of cytokines include functional fragments, precursors, analogues or derivatives that are known to persons having ordinary skill in the art. Illustrative examples of cytokines include, but are not limited to, interleukin-2 (IL-2), IL-10, IL-12, interferon alpha (IFN-α), IFN-γ, transforming growth factor beta (TGF-β), and tumor necrosis factor alpha (TNF-α).

In some embodiments, the parent polypeptide may be a single-chain antibody fragment, such as a single domain antibody (sdAb), single-chain antibody (scAb), single-chain variable fragment (scFv), bi-specific T-cell engager (BiTE), tandem di-scFv, and tandem tri-scFv. In some other embodiments, the parent polypeptide may be an antibody fragment derived from the heavy chain or light chain of immunoglobulins, and the present composite polypeptide comprises part of a full-length antibody, fragment crystallizable region (Fc region), fragment antigen binding fragment (Fab), Fab', F(ab')$_2$, Fab', Fv, (scFv)$_2$, sc(Fv)$_2$, diabody, Fd, Fd', or minibodies. The immunoglobulins may be derived from immunoglobulin D (IgD), IgE, or IgG. The antibody may be a bispecific antibody, chimeric antibody, human antibody, humanized antibody.

In certain embodiments, the antibody (as well as the functional fragment thereof) is specific for a cell surface antigen, which is associated with and/or overexpressed on a diffused tumor. Illustrative examples of such cell surface antigens include, CD5, CD19, CD20, CD22, CD23, CD27, CD30, CD33, CD34, CD37, CD38, CD43, CD72a, CD78, CD79a, CD79b, CD86, CD134, CD137, CD138, CD319. Antibodies (or fragments or derivatives thereof) against these cell surface antigens can be used as the targeting elements capable of directing the molecular construct comprising the same to the disease site. In other optional embodiments, the antibody (as well as the functional fragment or derivative thereof) is specific for other cell surface antigens, and such antibody can elicit a therapeutic effect within the human body; examples of such cell surface antigens include CD3, CD16a, CD28, CD134, cytotoxic T-lymphocyte-associated protein 4 (CTLA-4), programmed cell death 1 (PD-1), and programmed cell death 1 ligand 1 (PD-L1)). Still alternatively, the antibody (or the fragment thereof) may be specific for a tumor-associated antigen (TAA), such as, human epidermal growth factor receptor (HER1), HER2, HER3, HER4, carbohydrate antigen 19-9 (CA 19-9), CA 125, carcinoembryonic antigen (CEA), mucin 1 (MUC 1), ganglioside GD2, melanoma-associated antigen (MAGE), prostate-specific membrane antigen (PSMA), prostate stem cell antigen (PSCA), mesothelin, mucine-related Tn, Sialyl Tn, Globo H, stage-specific embryonic antigen-4 (SSEA-4), and epithelial cell adhesion molecule (EpCAM). Each TAA is often overexpressed on the cell surface of one or more types of solid tumors, an antibody against such TAA can be used as a targeting element as part of a molecular construct proposed herein. In some other optional embodiments, the antibody (or a fragment thereof) is specific for a growth factor selected from the group consisting of epidermal growth factor (EGF), mutant EGF, epiregulin, heparin-binding epidermal growth factor (HB-EGF), vascular endothelial growth factor A (VEGF-A), basic fibroblast growth factor (bFGF), and hepatocyte growth factor (HGF). In some embodiments, the antibody (or a fragment thereof) is specific for the cytokine described above.

(III) Molecular Construct of Functional Element and Composite Polypeptide Containing Metal Binding Motif In yet another aspect, one or more functional elements can be covalently conjugated with the composite polypeptide according to the above aspect/embodiments of the present disclosure by reacting with the sulfhydryl (SH) group of the cysteine residue in the metal binding motif of the composite polypeptide, thereby forming a molecular construct (or bioconjugate) according to this invention. In particular, the metal binding activity of the composite polypeptide allows for site-specific conjugation, thereby resulting in homogeneous molecular constructs.

According to optional embodiments of the present disclosure, the SH-reactive group is maleimide, iodoacetyl, bromoacetyl, vinyl sulfone, mono-sulfone, methylsulfonyl benzothiazole, or 2-pyridyldithiol group.

As could be appreciated, the functional element may be an effector molecule capable of eliciting desired therapeutic effect within a subject's body. Alternatively, the functional element may be a targeting element capable of directing the molecular construct to a target site within a subject's body. Still alternatively, the functional element is a pharmacokinetic element capable of modifying the pharmacokinetic profile of the molecular construct in a subject's body. Still alternatively, the functional element is in a form of a linker unit, or a bundle. According to certain embodiments of the present invention, the linker unit comprises a center core and a plurality of targeting, effector or pharmacokinetic elements; structure of said linker unit is discussed in section (IV) below.

Examples of effector molecules that can be used in the present invention include, but are not limited to, cytotoxic drugs, toll-like receptor (TLR) agonists, or chelators (alone or being complexed with a radioactive nuclide).

As would be appreciated, the cytotoxic drug exhibiting a cytotoxic effect on certain cells can be anti-estrogens (e.g., tamoxifen, raloxifene, and megestrol), LHRH agonists (e.g., goscrclin and leuprolide), anti-androgens (e.g., flutamide and bicalutamide), photodynamic therapies (e.g., vertoporfin, phthalocyanine, photosensitizer Pc4, and demethoxy-hypocrellin A), nitrogen mustards (e.g., cyclophosphamide, ifosfamide, trofosfamide, chlorambucil, estramustine, and melphalan), nitrosoureas (e.g., carmustine and lomustine), alkylsulphonates (e.g., busulfan and treosulfan), triazenes (e.g., dacarbazine, temozolomide), platinum containing compounds (e.g., cisplatin, carboplatin, oxaliplatin), vinca alkaloids (e.g., vincristine, vinblastine, vindesine, and vinorelbine), taxoids (e.g., paclitaxel, docetaxeal, and taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g., hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, idarubicin, epirubicin, pirarubicin, zorubicin, mitoxantrone), MDR inhibitors (e.g., verapamil), Ca2+ ATPase inhibitors (e.g., thapsigargin), imatinib, thalidomide, lenalidomide, tyrosine kinase inhibitors (e.g., axitinib, bosutinib, cediranib, dasatinib, erlotinib, gefitinib, imatinib, lapatinib, lestaurtinib, neratinib, nilotinib, semaxanib, sunitinib, toceranib, vandetanib, vatalanib, rituximab, nilotinib, sorafenib, everolimus, temsirolimus, proteasome inhibitors (e.g., bortezomib), mTOR inhibitors (e.g., rapamycin, temsirolimus, everolimus, and ridaforolimus), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, or hexamethyl melamine. According to one specific embodiment of the present disclosure, the cytotoxic drug is mertansine, auristatin, maytansine, doxorubicin, calicheamicin, or camptothecin.

Illustrative examples of the toll-like receptor agonist include lipoteichoic acid, glucan, motolimod, imiquimod, resiquimod, gardiquimod, CpG oligodeoxynucleotide (CpG DON), lipopolysaccharide (LPS), monophosphoryl lipid A, and zymosan.

In various embodiments, the chelator is selected from the group consisting of 1,4,7,10-tetraazacyclododecane-N,N', N'',N'''-tetraacetic acid (DOTA), N,N''-bis[2-hydroxy-5-(carboxyethyl)benzyl]ethylenediamine-N,N''-diacetic acid (HBED-CC), 1,4,7-triazacyclononane-1,4,7-triacetic acid (NOTA), 2-(4,7-bis(carboxymethyl)-1,4,7-triazonan-1-yl) pentanedioic acid (NODAGA), 2-(4,7,10-tris(carboxymethyl)-1,4,7,10-tetraazacyclododecan-1-yl)pentanedioic acid (DOTAGA), 1,4,7-triazacyclo-nonane phosphinic acid (TRAP), 1,4,7-triazacyclononane-1-[methyl(2-carboxyethyl)phosphinic acid]-4,7-bis[methyl(2-hydroxymethyl) phosphinic acid](NOPO), 3,6,9,15-tetraazabicyclo[9.3.1.] pentadeca-1(15),11,13-triene-3,6,9-triacetic acid (=PCTA), N'{5-[Acetyl(hydroxy)amino]pentyl}-N-[5-({4-[(5-aminopentyl)(hydroxy)amino]-4-oxobutanoyl}amino) pentyl]-N-hydroxysuccinamide (DFO), diethylenetriaminepentaacetic acid (DTPA), trans-cyclohexyl-diethylenetriaminepentaaceticacid (CHX-DTPA), 1-oxa-4,7,10-triazacyclododecane-4,7,10-triacetic acid (oxo-Do3A), p-isothiocyanatobenzyl-DTPA (SCN-Bz-DTPA), 1-(p-isothiocyanatobenzyl)-3-methyl-DTPA (1B3M), 2-(p-isothiocyanatobenzyl)-4-methyl-DTPA (1M3B), and 1-(2)-methyl-4-isocyanatobenzyl-DTPA (MX-DTPA). In some embodiments, the radioactive nuclide is $^{111}$In, $^{131}$I, or $^{177}$Lu, in other embodiments, the radioactive nuclide can be $^{90}$Y, $^{68}$Ga, $^{99m}$Tc, $^{64}$Cu, $^{153}$Gd, $^{155}$Gd, $^{157}$Gd, $^{213}$Bi, $^{225}$Ac or Fe.

In other embodiments, the selections of effector elements for the molecular constructs of this invention also covers a broad range of peptide-based molecules, including (1) antibody fragments specific for inflammatory cytokines (such as TNF-α, IL-12/IL-23, IL-17, IL-1, IL-6, BAFF), (2) antibody fragments specific for RANKL, (3) antibody fragments for CD3, and CD16a, expressed on T cells and NK cells, (4) antibody fragments specific for PD-1, PD-L1, CTLA-4 and other immune checkpoints, and (5) immunoenhancing cytokines (IFN-α, IFN-γ, IL-2, TNF-α).

The targeting elements according for use in the embodiments of the present invention can be selected depending on the disease to be treated. For example, targeting elements for treating various diseases include (1) antibody fragments specific for components of extracellular matrix in joints, skin or bone, such as, collagen I, collagen II, collagen III, collagen V, collagen VII, collagen IX, collagen XI, α-aggrecan, and osteonectin; (2) antibody fragments specific for cluster of differentiation markers, such as, CD19, CD20, CD22, CD30, CD52, CD79a, CD79b, CD38, CD56, CD74, CD78, CD138; or, CD319, CD5, CD4, CD7, CD8, CD30; or CD13, CD14, CD15, CD33, CD34, CD36, CD37, CD41, CD61, CD64, CD65, and CD11c, and other surface antigens of cells of lymphoid and myeloid lineages and of plasma cells, or (3) antibody fragments specific for receptors or antigens that are over expressed on cell surfaces of solid tumors, such as human epidermal growth factor receptor (HER1), HER2/Neu, HER3, Tn, Globo H, gangliosideGD-2, CA125, CA19-9, and carcinoembryonic antigen (CEA).

The targeting elements may also be antibodies of hormones, growth factors, or cytokines, in which receptors of hormones, growth factors, or cytokines are expressed on tumor cells or other diseased cells. In some other optional embodiments, the targeting element of the present molecular construct is a growth factor.

According to some embodiments of the present disclosure, at least one of the parent polypeptide and the functional element of the present disclosure is an antibody fragment specific for a growth factor. In some embodiments, the growth factor is selected from the group consisting of epidermal growth factor (EGF), mutant EGF, epiregulin, heparin-binding epidermal growth factor (HB-EGF), vascular endothelial growth factor A (VEGF-A), basic fibroblast growth factor (bFGF), and hepatocyte growth factor (HGF). With similar concept as described above, when the targeting element is the growth factor (e.g., EGF), the present molecular construct is capable of specifically targeting to the receptor-expressing cell/tissue/organ (e.g., tumor cell with the EGF receptor expressed thereon). In the case of the effector element being an antibody fragment specific for the growth factor (e.g., VEGF-A), it may capture and neutralize the growth factor-associated signaling transduction pathway (e.g., VEGF-A-induced angiogenesis). According to one working example, the present molecular construct is useful in treating solid tumors, in which the effector element is an antibody fragment specific for VEGF-A.

Examples of pharmacokinetic elements are $C_{8-28}$ fatty acid derivatives or $C_{8-28}$ dioic fatty acid derivatives. Each pharmacokinetic element is linked with one of the K residues via the ε-amino acid group of the K residue. According to various embodiments of the present disclosure, the functional element is a fatty acid derivative, which is derived from octanoic acid, pelargonic acid, decanoic acid, undecanoic acid, lauric acid, tridecanoic acid, myristic acid, pentadecanoic acid, palmitic acid, margaric acid, stearic acid, nonadecanoic acid, arachidic acid, heneicosanoic acid, behenic acid, tricosanoic acid, lignoceric acid, palmitoleic acid, oleic acid, lionleic acid, ricinoleic acid, or vaccenic acid, eicosapentaenoic acid (EPA), docosahexaenoic acid (DHA). According to certain embodiments of the present disclosure, the functional element is a dioic fatty acid derivative, which is derived from suberic acid, azelaic acid, sebacic acid, undecanedioic acid, dodecanedioic acid, brassylic acid, tetradecanedioic acid, pentadecanedioic acid, thapsic acid, heptadecanedioic acid, or octadecanedioic acid. In some embodiments, the present functional element is derived from myristic acid or palmitic acid. In other embodiments, the present functional element is derived from tetradecanedioic acid or thapsic acid.

(IV) Linker Unit for Conjugating with Composite Polypeptide Containing Metal Binding Motif In some optional embodiments, the functional element conjugated with the above-mentioned composite polypeptide is in a form of a bundle, or a linker unit. According to certain embodiments of the present invention, the linker unit comprises a center core and a plurality of targeting, effector or pharmacokinetic elements. As could be appreciated, such linker units also fall within the protection scope of the present disclosure.

According to certain embodiments of the present invention, the linker unit comprises a center core and a plurality of targeting, effector, or pharmacokinetic elements according to above-mentioned aspect/embodiments.

Specifically, the center core is a polypeptide that has 3-120 amino acid residues in length, and comprises 2 to 10 lysine (K) residues; for example, the present core may comprise 2, 3, 4, 5, 6, 7, 8, 9, or 10 K residues. Any two of the K residues are adjacent to each other or are separated by a filler. In some cases, the SH-reactive group is linked to the first or last K residue of the center core by forming an amide bond therewith. In other cases, the center core further comprises a terminal spacer, and the SH-reactive group is linked to the terminal amino acid residue of the terminal spacer by forming an amide bond therewith. In this way, it is feasible to conjugate the terminal SH-reactive group of the present linker unit with the SH group of the cysteine residue of the metal binding motif of the composite polypeptides, under a condition in which the cysteine residues of the parent polypeptide are mostly inactive, thereby achieving a site-specific conjugation that would result in homogeneous molecular constructs.

The terminal spacers may be an N-terminal spacer linked to the N-terminus of the first K residue or a C-terminal spacer linked to the C-terminus of the last K residue. Each of the filler and the terminal spacer comprises, independently, (1) 1 to 12 non-K amino acid residues, or (2) a PEGylated amino acid having 1 to 12 repeats of ethylene glycol (EG) unit.

In the cases where the linker unit does not have linking arms, each targeting, effector or pharmacokinetic element is linked to the K residue of the core via forming an amide bond with the ε-amino group of the K residue. On the other hand, when the linker unit of the molecular construct further comprises 2 to 10 linking arms, one terminus of each linking arm is linked to the K residue of the core via forming an amide bond with the ε-amino group of the K residue, and the other terminus of each linking arm is linked to each targeting, effector or pharmacokinetic element. For example, the linking arm can be a peptide comprising 2-12 non-K amino acid residues, or a polyethylene glycol (PEG) chain having 2-24 repeats of EG units.

According to optional embodiments of the present disclosure, before being conjugated with the targeting, effector, or pharmacokinetic element, the free terminus of the linking arm (i.e., the end that is not linked to the lysine residue of the center core) may carry a linking group selected from the group consisting of, amine, carboxyl, N-hydroxysuccinimidyl (NHS), azide, alkyne, cyclooctyne, tetrazine, and cyclooctene groups. Depending on the linking group (i.e., an amine, carboxyl, NHS, azide, alkyne, cyclooctyne, tetrazine, or cyclooctene group) modifying the sidechain amino group of the lysine residue (in the cases where there is no linking arm) or the linking group present at the free terminus of the linking arm, it is feasible to design a functional element (such as, a targeting element, a therapeutic effector element, or a pharmacokinetic element) with a corresponding functional group, so that the functional element may be linked to the free terminus of the linking arm via any of the following chemical reactions, (1) forming an amide bond therebetween: in this case, the linking group is an amine, carboxyl or NHS group, and the functional element has an amine or carboxyl group;

(2) the Copper(I)-catalyzed alkyne-azide cycloaddition reaction (CuAAC reaction): one of the linking group and the functional element has an azide or a picolyl azide group, whereas the other has an alkyne group;

(3) the inverse electron demand Diels-Alder (iEDDA) reaction: one of the linking group and the functional element has a tetrazine group, whereas the other has a cyclooctene group (e.g., a TCO or a norbornene group); or (4) the strained-promoted azide-alkyne click chemistry (SPAAC) reaction: one of the inking group and the functional element has an azide group, whereas the other has a cyclooctyne group.

According to various embodiments of the present disclosure, the tetrazine group is 1,2,3,4-tetrazine, 1,2,3,5-tetrazine, 1,2,4,5-tetrazine, or derivatives thereof; the cyclooctene group is a norbornene or a trans-cyclooctene (TCO) group; and the cyclooctyne group is selected from the group consisting of, dibenzocyclooctyne (DIBO), difluorinated cyclooctyne (DIFO), bicyclononyne (BCN), and dibenzoazacyclooctyne (DIBAC or DBCO). According to one embodiment of the present disclosure, the tetrazine group is 6-methyl-tetrazine.

According to some optional embodiments of the present invention, the center core carries a local negative charge at or near the amino acid residue linked with the SH-reactive group. Specifically, the local negative charge is present within the first 5 to 15 amino acid residues within the amino acid residue starting from the amino acid residue linked with the SH-reactive group. For example, the local negative charge is present within the first 5, 6, 7, 8, 9, 10, 11, 12, 13, 14, or 15 amino acid residues starting from the amino acid residue linked with the SH-reactive group. The local negative charge can be imparted by including one or more negatively-charged amino acid residues at pH=7, such as aspartate (D) and glutamate (E) residue.

Alternatively, the core may be conjugated with a plurality of effector elements that are negatively charged so that the center core carries a local negative charge at or near the SH-reactive group. For example, the effector element may comprise a chelator (e.g., DOTA, DOTAGA, and the like) that can increase the net negative charge of the linker unit as a whole.

The targeting, effector, and pharmacokinetic elements described in section (III) above are applicable in the embodiments of section (IV), and a detailed description thereof is omitted here for the sake of brevity. In various embodiments, linker units carrying a plurality of effector elements are referred to as "effector bundles" or "drug bundles," linker unit carrying a plurality of chelators are referred to as "chelator bundles," linker unit carrying a plurality of targeting elements are referred to as "targeting bundles," linker unit carrying a plurality of scFvs are referred to as "scFv bundles," linker unit carrying a plurality of pharmacokinetic elements are referred to as "pharmacokinetic (PK) bundles," and linker unit carrying a plurality of fatty acid and/or dioic fatty acid chains are referred to as "fatty acid (FA) bundles."

In certain embodiments, the fatty acid (or dioic fatty acid) derivative is a chemically modified fatty acid molecule (or dioic fatty acid). For example, the carboxyl group of the fatty acid molecule (or one of the carboxyl group of the dioic fatty acid molecule) is reacted with a chemical moiety with two functional groups, in which one functional group is carboxyl-reactive (thereby, forming a covalent bond with the (dioic) fatty acid molecule), whereas the other is a functional group reactive with the sidechain amino group of the lysine residue. According to optional embodiments of the present disclosure, the chemical entity modifying the (dioic) fatty acid molecule is a glutamate residue, aspartate residue, amino-EG2-acid, gamma-aminobutyric acid, or the like; however, the present disclosure is not limited thereto.

As could be appreciated, in cases where there is no cysteine residue or other amino acid residues containing a sulfhydryl group in a parent polypeptide, a terminal cysteine residue, instead of a terminal metal binding motif, may be introduced to form a composite polypeptide, and the present linker unit can form a conjugate with such composite polypeptide via the terminal cysteine residue.

(V) Linker Unit Carrying Multiple Composite Polypeptides Containing Metal Binding Motif In yet another aspect, the present invention is directed to a linker unit capable of carrying a plurality of composite polypeptides according to above-mentioned aspect/embodiments of the present disclosure. In some embodiments, such linker units are referred to as "peptide bundles."

According to certain embodiments of the present invention, the linker unit comprises a center core, 2 to 10 linking arms, and 2 to 10 composite polypeptides according to above-mentioned aspect/embodiments. The linking arms of the such linker unit have a SH-reactive group at the free terminus thereof, and since each composite polypeptide has the present metal binding motif, it is possible to conjugate the composite polypeptides to the linking arm in a site-specific way under a condition in which the cysteine residues of the parent polypeptide are mostly inactive.

Specifically, the center core is a polypeptide that has 3-120 amino acid residues in length, wherein the core comprises 2 to 10 lysine (K) residues; for example, the present core may comprise 2, 3, 4, 5, 6, 7, 8, 9, or 10 K residues and a conjugating group. Any two of the K residues are adjacent to each other or are separated by a filler.

In some cases, the center core further comprises a conjugating group linked to the first or last K residue of the center core by forming an amide bond therewith. Examples of the conjugating group include, but are not limited to, azide, alkyne, tetrazine, cyclooctene and cyclooctyne groups.

In other cases, the center core further comprises a terminal spacer, and the SH-reactive group is linked to the terminal amino acid residue of the terminal spacer by forming an amide bond therewith. The terminal spacers mat be an N-terminal spacer linked to the N-terminus of the first K residue or a C-terminal spacer linked to the C-terminus of the last K residue.

Each of the filler and the terminal spacer comprises, independently, (1) 1 to 12 non-K amino acid residues, or (2) a PEGylated amino acid having 1 to 12 repeats of ethylene glycol (EG) unit. In general, the terminal spacer or filler mentioned above may be, (1) a oligopeptide of 1-12 (i.e., 1, 2, 3, 4, 5, 6, 7, 8, 9, 10, 11, or 12) amino acid residues other than the K amino acid residue, or (2) a PEGylated amino acid, with EG units of 1 to 12 (i.e., having 1, 2, 3, 4, 5, 6, 7, 8, 9, 10, 11 or 12 EG units). Specifically, in the case when the present core comprises a plurality of K residues, the terminal spacer or filler may either comprise a PEGylated amino acid having 2-12 EG unit, or comprise 1-12 non-K amino acid residues, wherein each of the non-K amino acid residues are respectively selected from the group consisting of, glycine (G), aspartic acid (D), glutamic acid (E), serine (S), arginine (R), histidine (H), threonine (T), asparagine (N), glutamine (Q), proline (P), alanine (A), valine (V), isoleucine (I), leucine (L), methionine (M), phenylalanine (F), tyrosine (Y), and tryptophan (W) residues; preferably, each of the non-K amino acid residues are respectively selected from the group consisting of, G, S, R, H, T, N, Q, P, A, V, I, L, M, F, Y, and W residues; more preferably, each of the non-K amino acid residues are respectively G and/or S residues.

According to some embodiments, one terminus of each linking arm is linked to the K residue of the core via forming an amide bond with the ε-amino group of the K residue, whereas the other terminus of each linking arm has a sulfhydryl (SH)-reactive group. For example, the linking arm can be a peptide comprising 2-12 non-K amino acid residues, or a polyethylene glycol (PEG) chain having 2-24 repeats of EG units.

Illustrative SH-reactive groups include maleimide, haloacetyl (e.g., iodoacetyl or bromoacetyl), sulfone (e.g., vinyl sulfone, mono-sulfone, methylsulfonyl benzothiazole), and pyridyl disulfide (e.g., 2-pyridyldithiol) group.

According to some embodiments of the present disclosure, the linking arm is a peptide comprising 2-12 (i.e., 2, 3, 4, 5, 6, 7, 8, 9, 10, 11 or 12) amino acid residues (each of which may be a natural or non-natural amino acid residue) other than the K amino acid residue. For example, the linking arm is a peptide comprises 2-12 amino acid residues independently selected from the group consisting of, G, E, D, S, R, H, T, N, Q, P, A, V, I, L, M, F, Y, and W residues. According to one working example, the linking arm is a peptide comprising 5-10 amino acid residues that are independently selected from the group consisting of, G, S, E and R residues. Alternatively, the linking arm may be a PEG chain having 2-24 (i.e., 2, 3, 4, 5, 6, 7, 8, 9, 10, 11, 12, 13, 14, 15, 16, 17, 18, 19, 20, 21, 22, 23 or 24) repeats of EG unit; preferably, 5-15 repeats of EG units; more preferably, 6-12 repeats of EG units. As would be appreciated, the peptide or PEG chain of the linking arm may be substituted with a polymer of approximately the same length. A polymer comprising carbohydrate or other hydrophilic building blocks is suitable for use as the linking arms.

According to some embodiments of the present invention, each linking arm carries a local negative charge at or near the amino acid residue linked with the SH-reactive group. Specifically, the local negative charge is present within the first 5 to 15 amino acid residues within the amino acid residue starting from the amino acid residue linked with the SH-reactive group. For example, the local negative charge is present within the first 5, 6, 7, 8, 9, 10, 11, 12, 13, 14, or 15 amino acid residues starting from the amino acid residue linked with the SH-reactive group. The local negative charge can be imparted by including one or more negatively-charged amino acid residues at pH=7, such as aspartate (D) and glutamate (E) residue.

As could be appreciated, when the present core comprises at least two terminal spacers or fillers, each of the terminal spacers or fillers may be the same or different; that is, each terminal spacer or filler may comprise the same or different amino acid sequences and/or EG units. According to one embodiment of the present disclosure, the present core comprises three fillers, in which one of the spacers is a PEGylated amino acid having 8 repeats of EG unit, and the other two spacers are respectively one S residue and one G residue. According to another embodiment of the present disclosure, the present core comprises one terminal spacer and four fillers, in which one of the spacers consists of four G and two S residues, while the other four spacers respectively consists of one G and one S residue. According to still another embodiment of the present disclosure, the present core comprises two terminal spacers and three fillers, each being a PEGylated amino acid having 4 repeats of EG unit.

According to optional embodiments of the present invention, the above-mentioned linker unit comprising a plurality of composite polypeptides (or, the peptide bundle) can be conjugated with an additional linker unit by reacting with the conjugating group of the center core to form a molecular construct. For example, said additional linker unit may be an effector bundle, targeting bundle, or a PK bundle. For example, the additional linker unit may adopt the structure similar to those described in Applicant's previously filed patent applications. Briefly, the additional linker unit may have a structure similar to those described in section (III) above, with the exception that the terminal SH-reactive group is replaced with a conjugating group that is corresponding to the conjugating group of the peptide bundle.

In the embodiments where the targeting or effector elements carried by said additional linker unit is a peptide-based element, said peptide-based element may have a zinc-binding motif described above, and the additional linker unit may adopt the structure of the present peptide bundle, thereby forming a molecular construct composed of two peptide bundles carrying different kinds of functional elements.

In some optional embodiment, the conjugation group is part of a conjugating moiety, which has a functional group that is capable of forming a covalent bond with the α-amino group (—NH$_2$) of the terminal amino acid residue (i.e., the first linking amino acid residue or the N-terminal amino acid residue of the N-terminal spacer) or the carboxyl group (—COOH) of the terminal amino acid residue (i.e., the last linking amino acid residue or the C-terminal amino acid residue of the C-terminal spacer), so that the conjugating moiety is linked thereto. In certain embodiment, the core may have only one of the N- and C-terminal spacers, and has both the first and second conjugating moieties that are respectively linked to the two terminal amino acid residues (which may be the terminal linking amino acid residue or the terminal amino acid residue of the terminal spacer). There also embodiments in which the core comprises both of the N- and C-terminal spacers, and the two conjugating moieties are respectively linked to the terminal amino acid residues of the two terminal spacers. In preferred embodiments, the covalent bond formed between the conjugating moiety and the terminal amino acid residue is an amide bond. As could be appreciated, to ensure the homogeneity of the resultant bundle, it is important one conjugating moiety only has one functional group that is reactable with either the α-amino group or the carboxyl group.

Optionally, the conjugating moiety further comprises a PEG chain having 2-10 (i.e., 2, 3, 4, 5, 6, 7, 8, 9 or 10) repeats of EG units connecting the carboxyl or amino group and the conjugating group; for example, the PEG chain may have 4, 6, 7 or 8 repeats of EG unit.

According to various embodiments of the present disclosure, the two conjugating moieties may have the same reactivity or different reactivity. Preferably, when the second conjugating group of the conjugating moiety is an azide, alkyne, or cyclooctyne group, then the linking group of the linking arm cannot be any of the azide, alkyne or cyclooctyne group to avoid the reaction between the second conjugating group and the linking group; rather, the linking group can be a tetrazine, cyclooctene, amine, carboxyl, or N-hydroxysuccinimidyl (NHS) group. Alternatively, when the second conjugating group is a tetrazine or cyclooctene group, the linking group cannot be either the tetrazine or cyclooctene group; instead, the linking group can be an azide, alkyne, cyclooctyne, amine, carboxyl, or N-hydroxysuccinimidyl (NHS) group.

As could be appreciated, the number of the optional linking arms linked to the core is mainly determined by the number of linking amino acid resides (i.e., the K residues) comprised in the core. Since there are at least two linking amino acid residues comprised in the present core, the present targeting or effector bundle may comprise a plurality of linking arms.

As could be appreciated, the description regarding the effector, targeting or pharmacokinetic elements are applicable to all aspects/embodiments involving such elements, unless the context explicitly indicates otherwise.

As could be appreciated, during the solid-phase synthesis of the peptide center core, instead of attaching the functional elements to the core after the core has been synthesized, it is also feasible to incorporate a K amino acid residue modified with a specific functional element into the peptide chain. Therefore, according to various embodiments, K residues modified with different functional elements may be added sequentially during the solid-phase synthesis, so as to give a batch of homogeneous pharmacokinetic bundles, wherein each pharmacokinetic bundle may have two or more different functional elements linked thereto.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent.

Example 1

Synthesis of Mal-Peptide 1 Center Core

In this example, a peptide having five lysine residues was designed by the present inventor and the manufacture was outsourced to KareBay Co., Ltd. (Monmouth Junction, USA). This peptide can be used as a center core for constructing a linker unit or a functional bundle. Mal-Peptide 1 (maleimido-ethyl-GGSGGSKGSKGSKG-SKGSK; SEQ ID NO: 11) was synthesized using the standard Fmoc-based solid phase method. Mal-Peptide 1 had a purity of 95.67%.

The identification of the thus-synthesized peptide was carried out using mass spectrometry MALDI-TOF. Mass spectrometry analyses were performed by Mass Core Facility of Institute of Molecular Biology (IMB), Academia Sinica, Taipei, Taiwan. Measurements were performed on a Bruker Autoflex III MALDI-TOF/TOF mass spectrometer (Bruker Daltonics, Bremen, Germany).

FIG. 1 shows the result of mass spectrometry MALDI-TOF, which indicates that Mal-Peptide 1 has a molecular weight of 1,790.916 daltons.

Example 2

Synthesis of Mal-Peptide 2-DOTA Bundle

Figure 2:
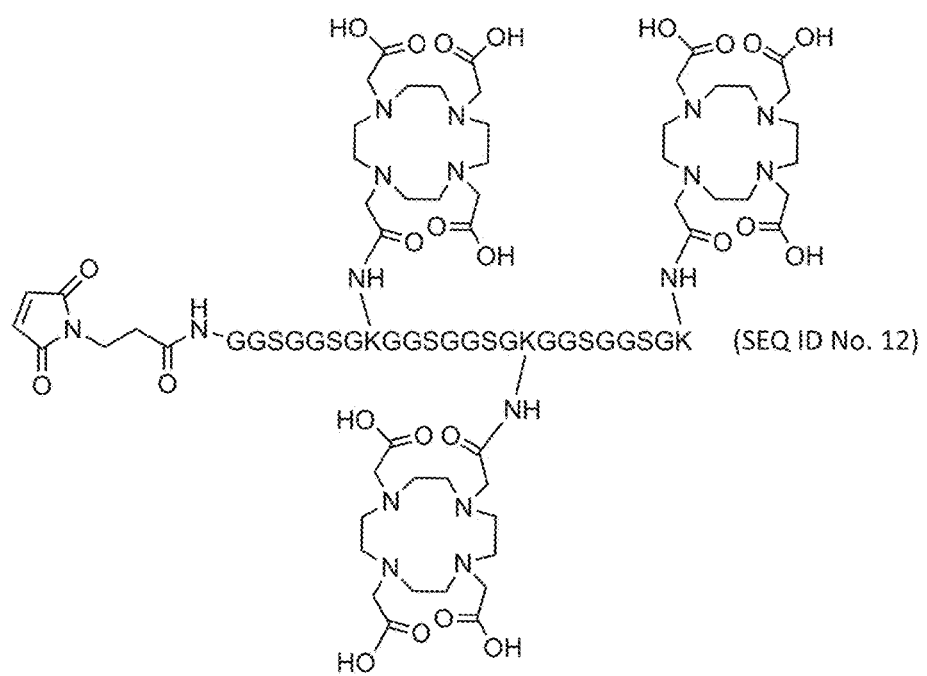
FIG. 2 shows the structure of the Mal-Peptide 2-DOTA bundle according to one working example of the present invention.

In this example, a chelator bundle (see, FIG. 2) having a maleimide-containing peptide with three lysine residues as the center core and three DOTA molecules conjugated with the center core (Mal-Peptide 2-DOTA bundle) was designed by the present investors and the manufacture was outsourced to KareBay Co., Ltd. (Monmouth Junction, USA).

Mal-Peptide 2 (maleimido-ethyl-GGSGGSGKGGSGGSGKGGSGGSGK, SEQ ID NO: 12) for use as the center core was synthesized using the standard Fmoc-based solid-phase synthesis, and then the DOTA molecules are conjugated to the center core using the liquid-phase synthesis.

Figure 3A:
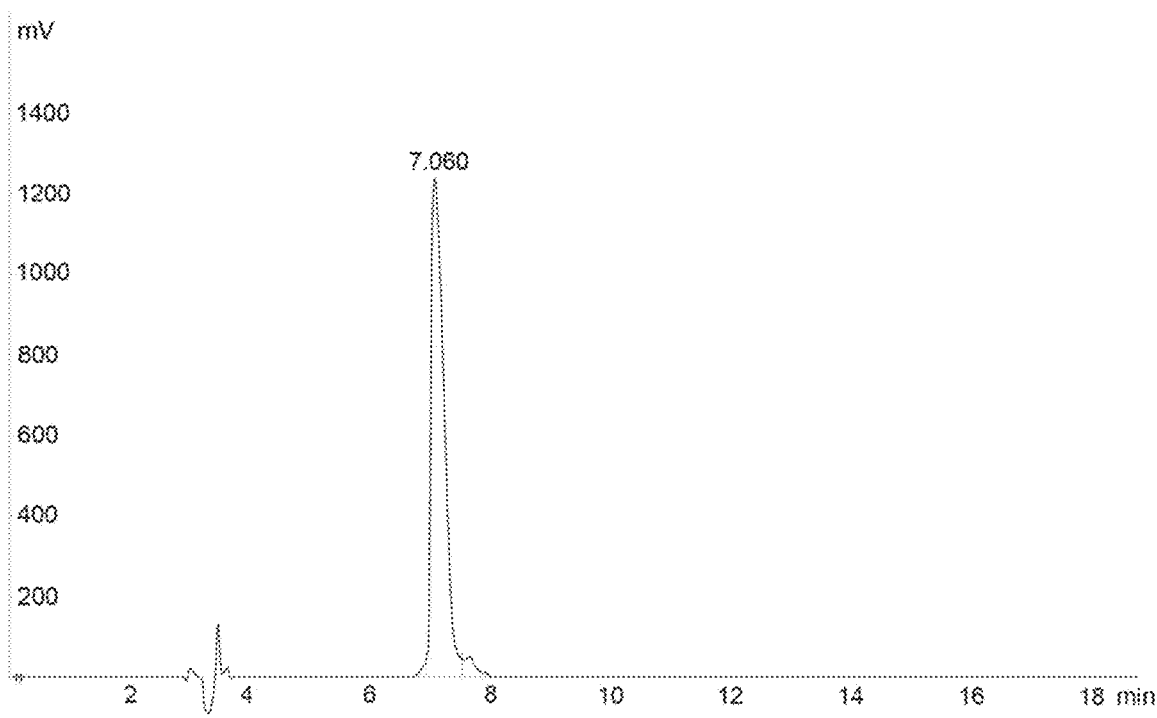
FIG. 3A shows the reversed-phase analytical HPLC elution profile of the Mal-Peptide 2-DOTA bundle.

The purified sample of the chelator bundle thus-synthesized was analyzed using reversed-phase analytical high-performance liquid chromatography (HPLC) on a Supelco C18 column (250 mm×4.6 mm; 5 µm), using a mobile phase of acetonitrile and 0.1% trifluoroacetic acid, a linear gradient of 0% to 100% acetonitrile over 30 minutes, at a flow rate of 1.0 ml/min and a column temperature of 35° C. FIG. 3A shows the reversed-phase HPLC profile of the chelator bundle of Example 2, which indicates that the peak of the chelator bundle has a retention time of 7.06 minutes.

Figure 3B:
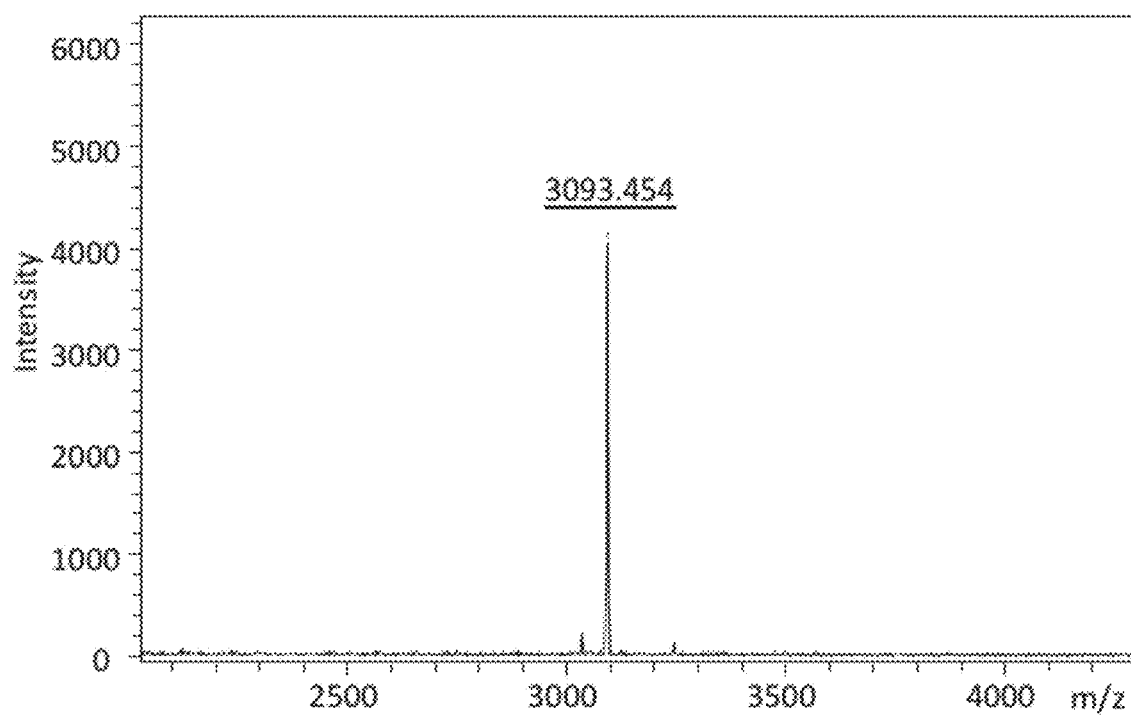
FIG. 3B is the MALDI-TOF result of the Mal-Peptide 2-DOTA bundle according to one working example of the present invention.

The identification of the Mal-Peptide 2-DOTA bundle was carried out by mass spectrometry MALDI-TOF. FIG. 3B shows the result of mass spectrometry MALDI-TOF indicated that the present chelator bundle has a molecular weight of 3,093.454 daltons.

Example 3

Construction, Expression and Purification of Recombinant 2-Chain (scFv α CD19)-Fc-MBM-1

The $V_L$ and $V_H$ of the scFv specific for human CD19 were from monoclonal antibody RB4v1.2. The gene sequence encoding the scFv-CH2-CH3 (human γ1) recombinant chain was configured by fusing a gene sequence encoding the scFv specific for human CD19 to the upstream of the gene sequence encoding the flexible hinge region and the CH2 domain of IgG1 Fc, and the gene sequence encoding the metal binding motif (MBM)-1, ACPGHA (SEQ ID NO: 7) was fused to the downstream of the gene sequence encoding the CH3 domain of IgG1.Fc and a short flexible linker, GGGG (SEQ ID NO: 9).

Figure 4A:
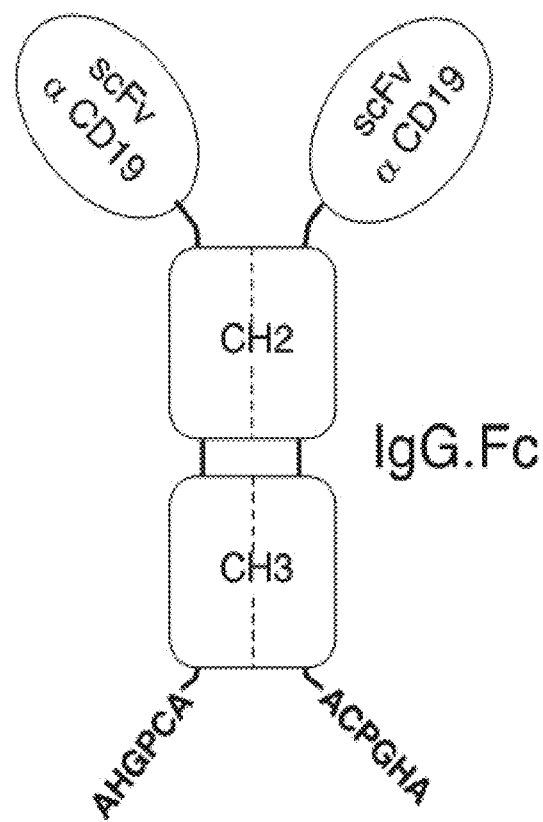
FIG. 4A shows the structure of the recombinant 2-chain (scFv α CD19)-Fc-MBM-1 according to one working example of the present invention.

The scFvs were configured in two orientations, i.e., $V_L$-linker-$V_H$ and VH-linker-$V_L$, wherein the $V_L$ and $V_H$ were connected by a hydrophilic linker, GSTSGSGKPGSGEG-STKG (SEQ ID NO: 10). The amino acid sequences of the recombinant chain of the present (scFv α CD19)-Fc-MBM-1 in the $V_L$-linker-$V_H$ and VH-linker-$V_L$ configurations are shown in SEQ ID NOs: 13 and 14, respectively, and a general structure for these 2-chain (scFv α CD19)-Fc-MBM-1 molecular constructs is provided in FIG. 4A.

To prepare the above-mentioned recombinant proteins, a mammalian overexpression system based on Expi293F™ cell line was used. This system employed ExpiFectamine™ 293 transfection kit (Life Technologies, Carlsbad, USA) consisting of the Expi293F™ cell line, the cationic lipid-based ExpiFectamine™ 293 Reagent and ExpiFectamine™ 293 transfection Enhancers 1 and 2, and the medium, which was part of the expression system (Gibco, N.Y., USA).

The gene sequence constructed as described above was placed in the pcDNA3 expression cassette. Expi293F cells were seeded at a density of $2.0\times10^6$ viable cells/ml in Expi293F expression medium and maintained for 18 to 24 hours prior to transfection to ensure that the cells were actively dividing at the time of transfection. For transfection, in a 2-liter Erlenmeyer shaker flask, $7.5\times10^8$ cells in 255 ml medium were transfected using ExpiFectamine™ 293 transfection reagent per the manufacture's instruction. The transfected cells were incubated at 37° C. for 16 to 18 hours post-transfection in an orbital shaker (125 rpm) and then the incubated cells were added with ExpiFectamine™ 293 transfection enhancer 1 and enhancer 2 to a shaker flask, and incubated for another 5 to 6 days. Culture supernatants were harvested and the expressed hIgG1.Fc-fused recombinant proteins in the media were purified using Protein A affinity chromatography.

Figure 4B:
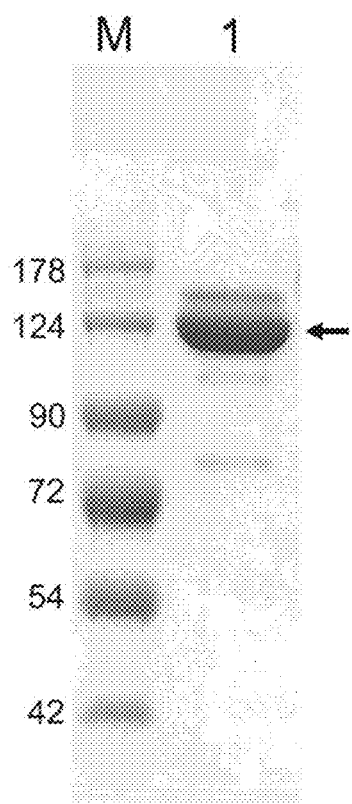
FIG. 4B shows the non-reducing SDS-PAGE analysis of the recombinant 2-chain ($V_L$-$V_H$ scFv α CD19)-Fc-MBM-1 according to one working example of the present invention.

After buffer exchange to phosphate buffered saline (PBS), the concentration of the present (scFv α CD19)-Fc-MBM-1 was determined and analyzed using 10% SDS-PAGE. The results indicate that the present (scFv α CD19)-Fc-MBM-1 had a molecular weight of about 120 kDa on the non-reducing SDS-PAGE, which is somewhat larger than the expected size 110 kDa. In FIG. 4B, the non-reducing SDS-PAGE result of the 2-chain ($V_L$-$V_H$ scFv α CD19)-Fc-MBM-1 (see, the major band indicated by an arrow) is shown as an example. As could be appreciated, the SDS-PAGE results here are for a quick confirmation of the approximate molecular weight of the molecular construct thus-synthesized, and a more accurate analysis of the molecular weight were determined using mass spectrometry analysis. For example, the MALDI-TOF result of the present molecular construct is provided in FIG. 23.

Example 4

Construction, Expression and Purification of Recombinant 2-Chain (scFv α CD19)-Fc-MBM-2

In this example, the recombinant 2-chain (scFv α CD19)-Fc-MBM-2 in a $V_L$-linker-$V_H$ configuration was constructed, expressed and purified using the protocols similar to those set forth in the working example above, with the exception that a different metal binding motif, GCPGHA (SEQ ID NO: 8, hereinafter, MBM-2) was used. The amino acid sequences of the recombinant chain of the present ($V_L$-$V_H$ scFv α CD19)-Fc-MBM-2 is shown in SEQ ID NO: 15.

Figure 5:
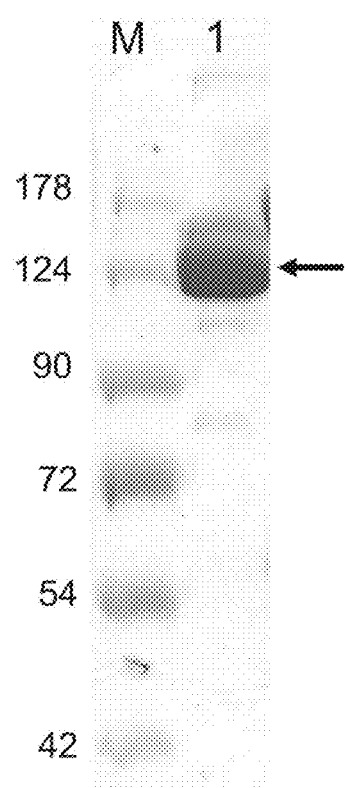
FIG. 5 shows the non-reducing SDS-PAGE analysis of recombinant 2-chain ($V_L$-$V_H$ scFv α CD19)-Fc-MBM-2 according to one working example of the present invention.

The SDA-PAGE results in FIG. 5 indicates that the recombinant chain of the present molecular construct has a size of about 120 kDa (indicated by an arrow), which is somewhat larger than the expected size.

Example 5

Construction, Expression and Purification of Recombinant 2-Chain (scFv α CD19)-Fc-MBM-3

In this example, the recombinant 2-chain (scFv α CD19)-Fc-MBM-3 in a $V_L$-linker-$V_H$ configuration was constructed, expressed and purified using the protocols similar to those set forth in the working example above, with the exception that a different metal binding motif, GCGGHA (SEQ ID NO: 6, hereinafter, MBM-3) was used. The amino acid sequences of the recombinant chain of the present (scFv α CD19)-Fc-MBM-3 in the $V_L$-linker-$V_H$ configuration is shown in SEQ ID NO: 16.

Figure 6:
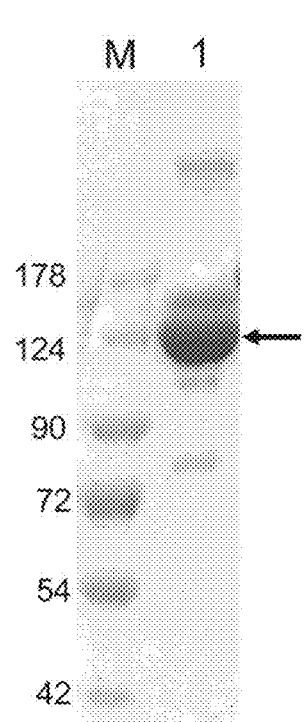
FIG. 6 shows the non-reducing SDS-PAGE analysis of recombinant 2-chain ($V_L$-$V_H$ scFv α CD19)-Fc-MBM-3 according to one working example of the present invention.

Characterization of the ($V_L$-$V_H$ scFv α CD19)-Fc-MBM-3 molecular construct was performed using SDS-PAGE. The SDA-PAGE results in FIG. 6 indicates that the recombinant chain of the new construct has a size of about 110 kDa (indicated by an arrow), which is consistent with the expected size.

Example 6

Construction, Expression and Purification of Recombinant Anti-CD19 Antibody-MBM

The recombinant IgG (human γ1) molecular constructs were constructed by fusing the short flexible linker, GGGG (SEQ ID NO: 9) and the MBM sequence (in this example, MBM-1 or MBM-2) to the C-terminus of the heavy chain of the intact antibody specific for CD19. The two gene sequences were inserted into a pG1K expression cassette with the multiple cloning site. The expression and purification of the present recombinant anti-CD19 antibody-MBM were carried out using protocols similar to those described in the working example above.

The amino acid sequences of the heavy chain of the antibody specific for human CD19 antibody-MBM-1 or MBM-2 are respectively indicated in SEQ ID NOs: 17 and 18, and the amino acid sequence of the light chain of the intact anti-CD19 antibody is indicated in SEQ ID NO: 19.

Figure 7A:
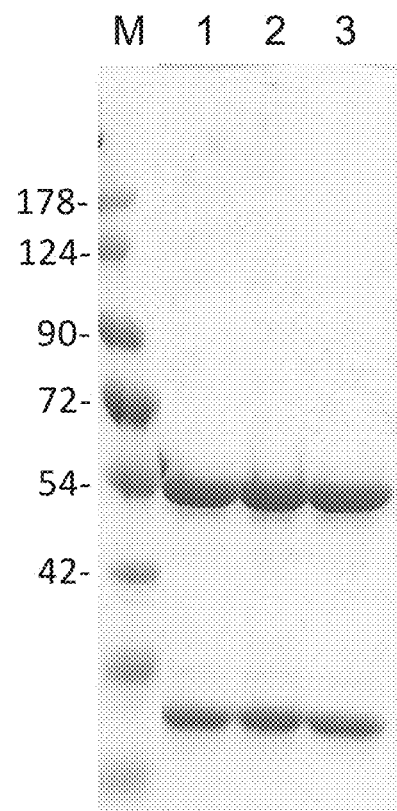
FIG. 7A shows the reducing SDS-PAGE analysis of the anti-CD19 antibody-MBM-1 or anti-CD19 antibody-MBM-2 according to one working example of the present invention.

Characterization of the molecular constructs was performed using SDS-PAGE. The reducing SDA-PAGE results in FIG. 7A shows that a control protein (lane 1), human CD19 antibody-MBM-1 (lane 2), and human CD19 antibody-MBM-2 (lane 3) have a higher MW band of size of about 55 kDa and a lower MW band of size of about 25 kDa, which are consistent with the expected sizes of the heavy chain and light chain of the constructs, respectively.

Figure 7B:
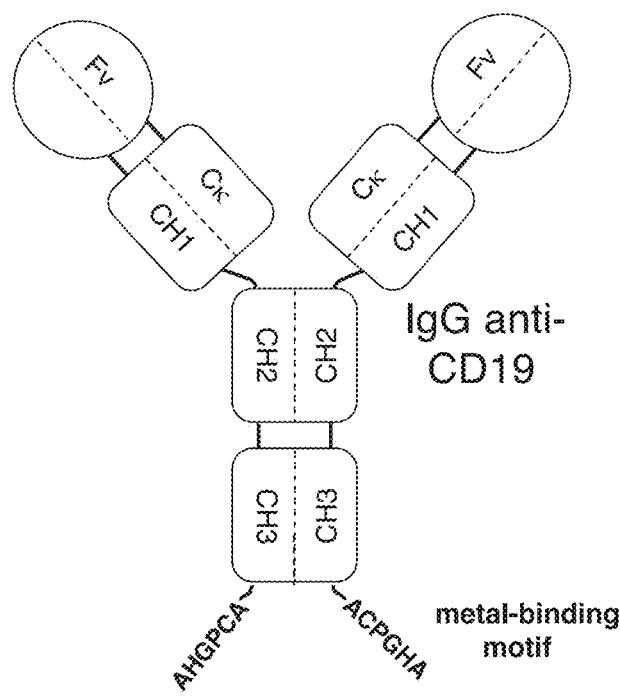
FIG. 7B shows the reducing SDS-PAGE analysis of the anti-CD19 antibody-MBM-1 or anti-CD19 antibody-MBM-2 according to one working example of the present invention.

A general structure for the anti-CD19 antibody-MBM-1 molecular construct is provided in FIG. 7B.

Example 7

Construction, Expression and Purification of Recombinant 2-Chain (scFv α CD33)-Fc-MBM The $V_L$ and $V_H$ of the scFv specific for human CD33 were from monoclonal antibody huMy9-6. The gene sequence encoding the (scFv α CD33)-CH2-CH3 (human γ1) recombinant chain was configured by fusing a gene sequence encoding the scFv specific for human CD33 to the upstream of the gene sequence encoding the flexible hinge region and the CH2 domain of IgG1.Fc, and the gene sequence encoding the MBM-1 or MBM-2 was fused to the downstream of the gene sequence encoding the CH3 domain of IgG1.Fc and a short flexible linker, GGGG (SEQ ID NO: 9).

The scFvs were configured in two orientations, i.e., $V_L$-linker-$V_H$ and $V_H$-linker-$V_L$, wherein the $V_L$ and $V_H$ were connected by a hydrophilic linker, GSTSGSGKPGSGEG-STKG (SEQ ID NO: 10). The amino acid sequences of the recombinant chain of the present (scFv α CD33)-Fc-MBM-1 in the $V_L$-linker-$V_H$ and $V_H$-linker-$V_L$ configurations are shown in SEQ ID NOs: 20 and 21, respectively, whereas the amino acid sequences of the recombinant chain of the present (scFv α CD33)-Fc-MBM-2 in the $V_L$-linker-$V_H$ and $V_H$-linker-$V_L$ configurations are shown in SEQ ID NOs: 22 and 23, respectively.

The expression and purification of the present recombinant 2-chain (scFv α CD33)-Fc-MBM were carried out using protocols similar to those described in the working example above.

Figure 8:
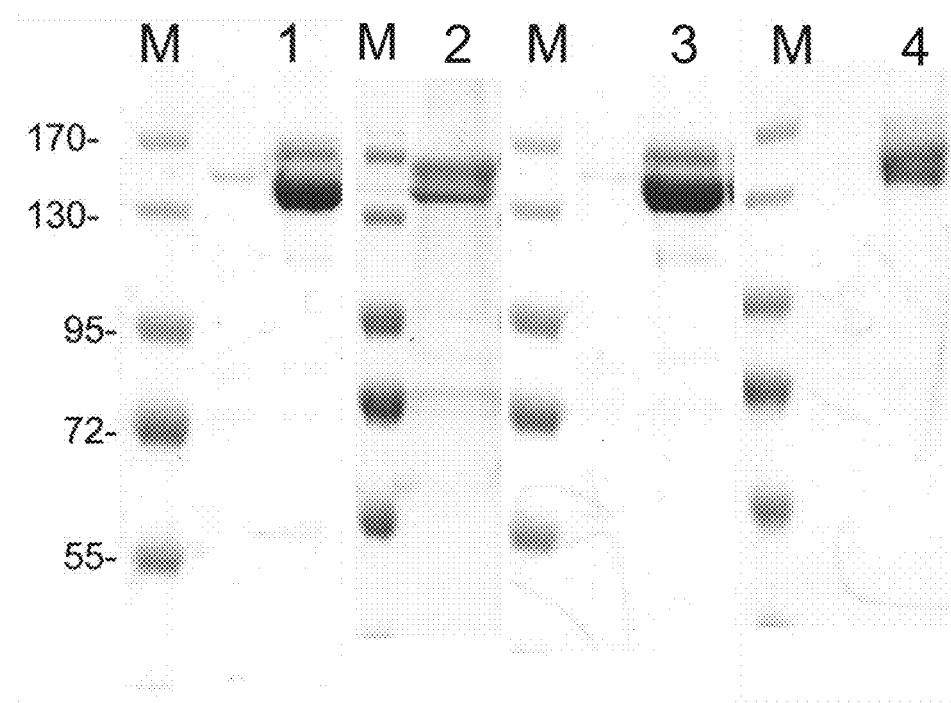
FIG. 8 shows the non-reducing SDS-PAGE analysis of four (scFv α CD33)-Fc-MBM molecular constructs according to one working example of the present invention.

Characterization of the molecular constructs were performed using non-reducing SDS-PAGE. The SDA-PAGE results in FIG. 8 shows that each of the ($V_L$-$V_H$ scFv α CD33)-Fc-MBM-1 (lane 1), ($V_H$-$V_L$ scFv α CD33)-Fc-MBM-1 (lane 2), ($V_L$-$V_H$ scFv α CD33)-Fc-MBM-2 (lane 3), ($V_H$-$V_L$ scFv α CD33)-Fc-MBM-2 (lane 4) have a size of about 120 kDa, which is somewhat larger than the expected size of 110 kDa.

Example 8

Construction, Expression and Purification of Recombinant 2-Chain (scFv α CD20)-Fc-MBM The $V_L$ and $V_H$ of the scFv specific for human CD20 were from monoclonal antibody ocrelizumab. The metal binding motifs MBM-1, MBM-2, and MBM-3 were respectively fused to the C-terminal of CH3 domain of the (scFv α CD20)-CH2-CH3 (human γ1) recombinant chain through a short flexible linker, GGGG (SEQ ID NO: 9). The scFv had the orientations of $V_L$-linker-$V_H$ or $V_H$-linker-$V_L$. The $V_L$ and $V_H$ were connected by a hydrophilic linker, GST-SGSGKPGSGEGSTKG (SEQ ID NO: 10).

The expression and purification of the present recombinant 2-chain (scFv α CD20)-Fc-MBM-1, -MBM-2, or MBM-3 were carried out using protocols similar to those described in the working example above. The sequences of the recombinant chain of the present ($V_L$-$V_H$ scFv α CD20)-Fc-MBM-1, ($V_H$-$V_L$ scFv α CD20)-Fc-MBM-1, ($V_H$-$V_L$ scFv α CD20)-Fc-MBM-2, scFv α CD20)-Fc-MBM-3, and ($V_H$-$V_L$ scFv α CD20)-Fc-MBM-3 are set forth in SEQ ID NOs: 24, 25, 26, 27 and 28, respectively.

The expression and purification of the present recombinant 2-chain (scFv α CD20)-Fc-MBM were carried out using protocols similar to those described in the working example above.

Figure 9:
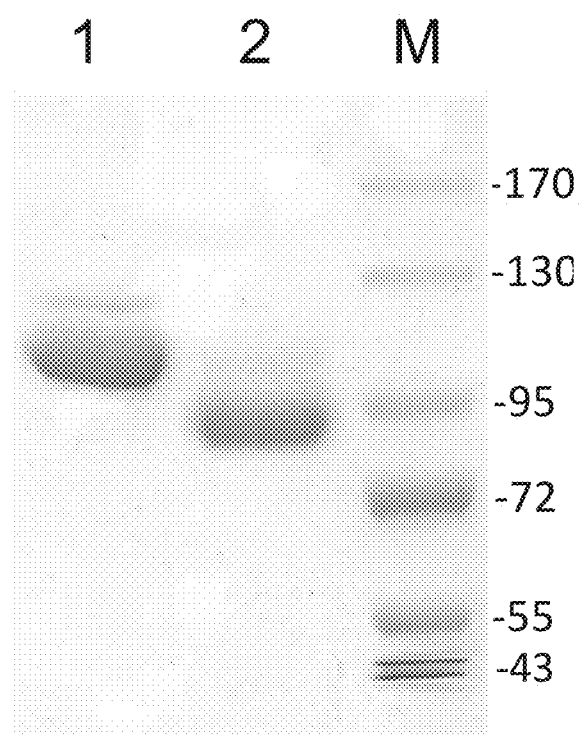
FIG. 9 shows the non-reducing SDS-PAGE analysis of recombinant (scFv α CD20)-Fc-MBM-1 in both $V_L$-$V_H$ and $V_H$-$V_L$ configurations according to one working example of the present invention.
Figure 10A:
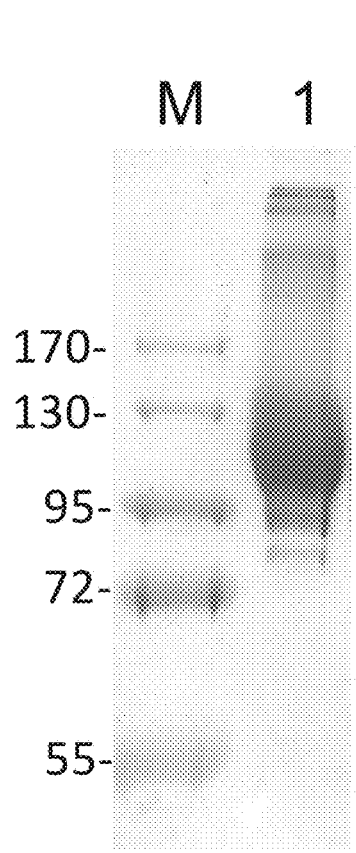
FIG. 10A shows the non-reducing SDS-PAGE analysis of recombinant 2-chain ($V_H$-$V_L$ scFv α CD20)-Fc-MBM-2 according to one working example of the present invention.
Figure 10B:
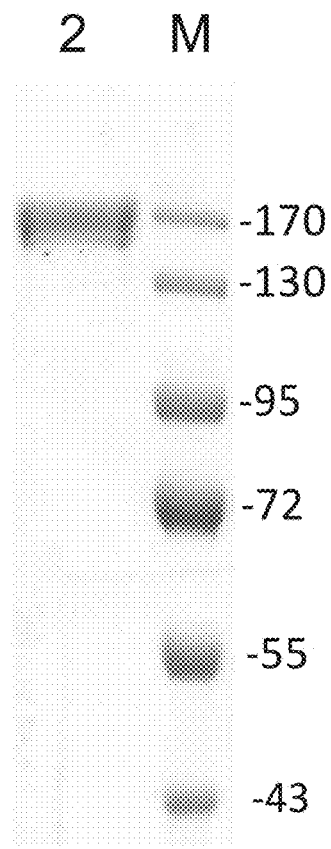
FIG. 10B shows the non-reducing SDS-PAGE analysis of recombinant 2-chain ($V_L$-$V_H$ scFv α CD20)-Fc-MBM-3 according to one working example of the present invention.

Characterization of the molecular constructs were warried out using non-reducing SDS-PAGE. The SDA-PAGE results in FIG. 9 shows that both the ($V_L$-$V_H$ scFv α CD20)-Fc-MBM-1 (lane 1) and ($V_H$-$V_L$ scFv α CD20)-Fc-MBM-1 (lane 2) molecular constructs have a size of about 120 kDa, which is somewhat greater than the expected size of 110 kDa. The SDA-PAGE results in FIG. 10A and FIG. 10B respectively show that both $V_H$-$V_L$ scFv α CD20)-Fc-MBM-2 and ($V_L$—$V_H$ scFv α CD20)-Fc-MBM-3 molecular constructs have a size of about 120 kDa, which is somewhat greater than the expected size of 110 kDa.

Example 9

Construction, Expression and Purification of Recombinant 2-Chain (scFv α CA19-9)-Fc-MBM Mouse B cell hybridoma HB8059 producing anti-CA19-9 antibody was purchased from Developmental Studies Hybridoma Bank at the University of Iowa. Poly(A)+ RNA was reverse-transcribed with a SuperScript III RT-PCR system (Invitrogen, Waltham, USA), and first strand cDNA was synthesized. The $V_H$ and $V_L$ nucleotide and amino acid sequences of HB8059 had not been published. To determine the sequences of variable regions of HB8059, cDNA of $V_H$ and $V_L$ were amplified by PCR using a set of DNA primers provided by Ig-primer Sets (Novagen, Madison, USA) according to the manufacturer's instructions. The amino acid sequence of $V_H$ and $V_L$ of HB8059 monoclonal antibody specific for human CA19-9 are described in SEQ ID NOs: 29 and 30.

The MBM-1 or MBM-3 was fused to the C-terminal of CH3 domain (scFv α CA19-9)-CH2-CH3 (human γ1) recombinant chain through a short flexible linker, GGGG (SEQ ID NO: 9). The scFvs had the orientation of $V_L$-linker-$V_H$. The $V_L$ and $V_H$ were connected by a hydrophilic linker, GSTSGSGKPGSGEGSTKG (SEQ ID NO: 10). The sequences of the recombinant chain of the present (scFv α CA19-9)-Fc-MBM-1 and (scFv α CA19-9)-Fc-MBM-3 are shown as SEQ ID NOs: 31 and 32, respectively.

The expression and purification of the present recombinant 2-chain (scFv α CA19-9)-Fc-MBM was carried out using protocols similar to those described in the working example above.

Figure 11A:
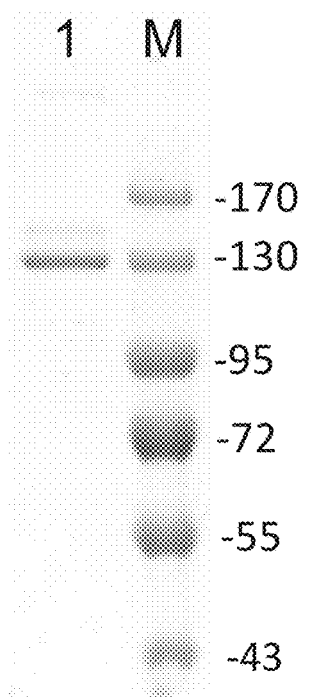
FIG. 11A shows the non-reducing SDS-PAGE analysis of recombinant 2-chain ($V_L$-$V_H$ scFv α CA19-9)-Fc-MBM-1 according to one working example of the present invention.
Figure 11B:
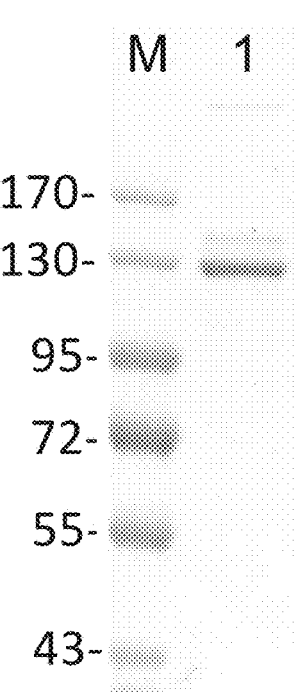
FIG. 11B shows the non-reducing SDS-PAGE analysis of recombinant 2-chain ($V_L$-$V_H$ scFv α CA19-9)-Fc-MBM-2 according to one working example of the present invention.

Characterization of the molecular construct was carried out using SDS-PAGE. The SDA-PAGE results in FIG. 11A and FIG. 11B show that the recombinant chain of both (scFv α CA19-9)-Fc-MBM-1 molecular and (scFv α CA19-9)-Fc-MBM-3 constructs has a size of about 120 kDa (lane 1), which is somewhat larger than the expected size of 110 kDa.

Example 10

Construction, Expression and Purification of Recombinant 2-Chain (scFv α CD38)-Fc-MBM The $V_L$ and $V_H$ of the scFv specific for human CD38 were from monoclonal antibody daratumumab. The metal binding motifs MBM-1 and MBM-2 were respectively fused to the C-terminal of CH3 domain of the (scFv α CD38)-CH2-CH3 (human γ1) recombinant chain through a short flexible linker, GGGG (SEQ ID NO: 9). The scFv had the orientations of $V_L$-linker-$V_H$ or $V_H$-linker-$V_L$. The $V_L$ and $V_H$ were connected by a hydrophilic linker, GSTSGSGKPGSGEGSTKG (SEQ ID NO: 10). The expression and purification of the present recombinant 2-chain (scFv α CD38)-Fc-MBM-1 or -MBM-2 were carried out using protocols similar to those described in the working example above. The sequences of the recombinant chain of the present ($V_L$-$V_H$ scFv α CD38)-Fc-MBM-1, ($V_H$-$V_L$ scFv α CD38)-Fc-MBM-1, ($V_L$-$V_H$ scFv α CD38)-Fc-MBM-2, and ($V_H$-$V_L$ scFv α CD38)-Fc-MBM-2 are set forth in SEQ ID NOs: 33, 34, 35, and 36, respectively.

Figure 12A:
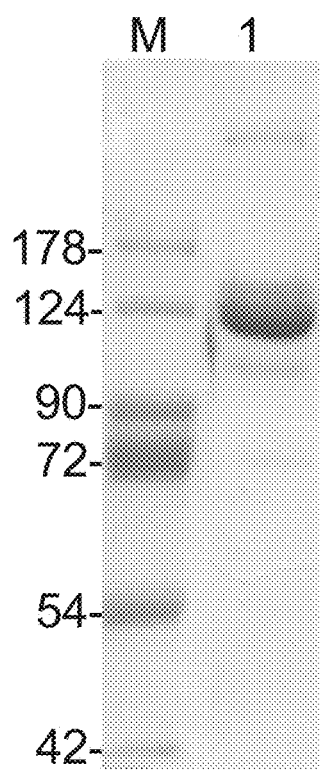
FIG. 12A shows the non-reducing SDS-PAGE analysis of recombinant 2-chain ($V_L$-$V_H$ scFv α CC38)-Fc-MBM-1 according to one working example of the present invention.
Figure 12B:
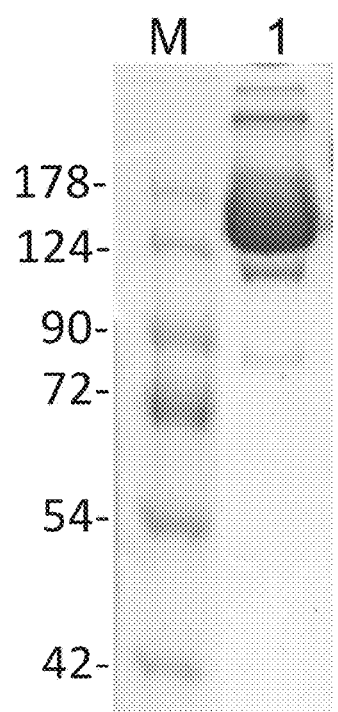
FIG. 12B shows the non-reducing SDS-PAGE analysis of recombinant 2-chain ($V_L$-$V_H$ scFv α CC38)-Fc-MBM-2 according to one working example of the present invention.

Characterization of the molecular construct was carried out using SDS-PAGE. The SDA-PAGE result in FIG. 12A shows that the recombinant chain of ($V_L$-$V_H$ scFv α CD38)-Fc-MBM-1 (lane 1) has a size of about 120 kDa, which is somewhat larger than the expected size of 110 kDa. The SDA-PAGE result in FIG. 12B shows that the recombinant chain of the ($V_L$-$V_H$ scFv α CD38)-Fc-MBM-2 has a size of about 120 kDa, which is somewhat larger than the expected size of 110 kDa.

Example 11

Preparation of Recombinant 2-Chain (scFv α CD19)-Fc-MBM-1×2 DOTA Bundles

Figure 13A:
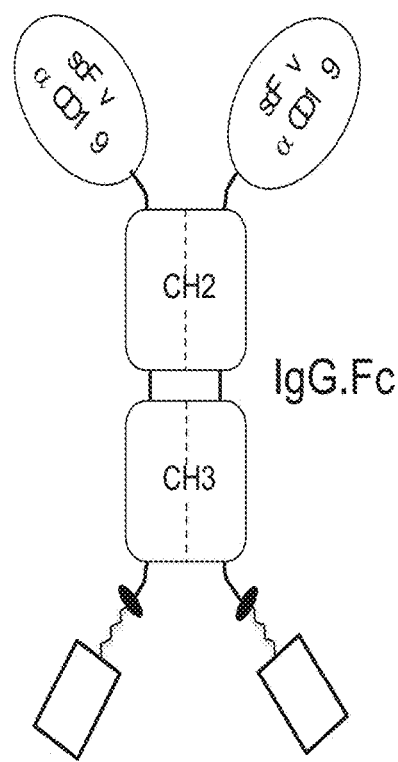
FIG. 13A shows the structure of the recombinant 2-chain (scFv α CD19)-Fc-MBM-1×2 DOTA bundles according to one working example of the present invention.

In this example, a molecular construct having two DOTA bundles respectively conjugated to the two cysteine residues of the metal binding motif of 2-chain (scFv α CD19)-Fc-MBM-1 was prepared; a schematic diagram illustrating the structure of this molecular construct is shown in FIG. 13A. To reduce the cysteine residue at the C-terminal end of the purified recombinant 2-chain ($V_L$-$V_H$ scFv α CD19)-Fc-MBM-1 from Example 3, the recombinant proteins in sodium succinate buffer (10 mM sodium succinate, pH6.0, and 30 mM sucrose) were reduced by incubating with 45 μM tris(2-carboxyethyl)phosphine (TCEP) at room temperature for 30 minutes with gentle shaking. After the reduction reaction, the excess TCEP was removed by dialysis against 10 mM sodium succinate buffer (pH 6.0 with 30 mM sucrose) containing 60 μM Zn (II) ions. Then, the reduced protein samples were treated with 15 μM Mal-Peptide 2-DOTA bundle from Example 2 and then incubated for 1 hour at room temperature. The non-reacted DOTA bundle were removed using a desalting column and the product was analyzed using SDS-PAGE.

Figure 13B:
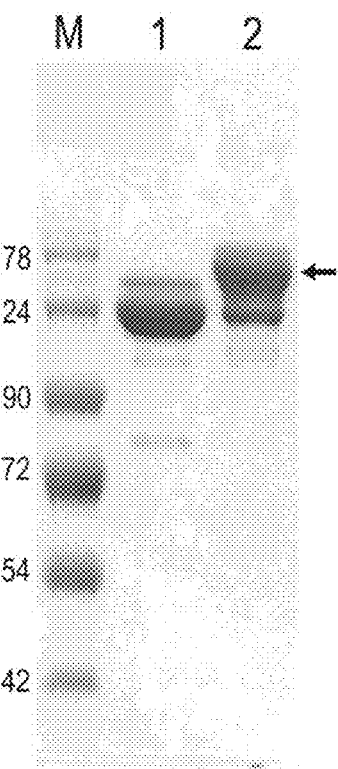
FIG. 13B shows the non-reducing SDS-PAGE analysis of recombinant 2-chain (scFv α CD19)-Fc-MBM-1×2 DOTA bundles according to one working example of the present invention.

FIG. 13B shows the result of the SDS-PAGE analysis of the present molecular construct (illustrated below), which indicates that the present molecular construct has a molecular weight of about 120 kDa (lane 2, indicated by an arrow), which is slightly larger than the expected size. The non-conjugated fusion protein was in lane 1. As could be seen in FIG. 13B, the yield of the conjugation of DOTA bundles to the recombinant 2-chain (scFv α CD19)-Fc-MBM-1 is approximately 90%. These protein bands on SDS-PAGE was quantified by Image J.

Example 12

Preparation of Recombinant 2-Chain (scFv α CD19)-Fc-MBM-2×2 DOTA Bundles

In this example, the conjugation of two DOTA bundles to the recombinant 2-chain ($V_L$-$V_H$ scFv α CD19)-Fc-MBM-2 from Example 4 was performed as described in the preceding Example.

Figure 14:
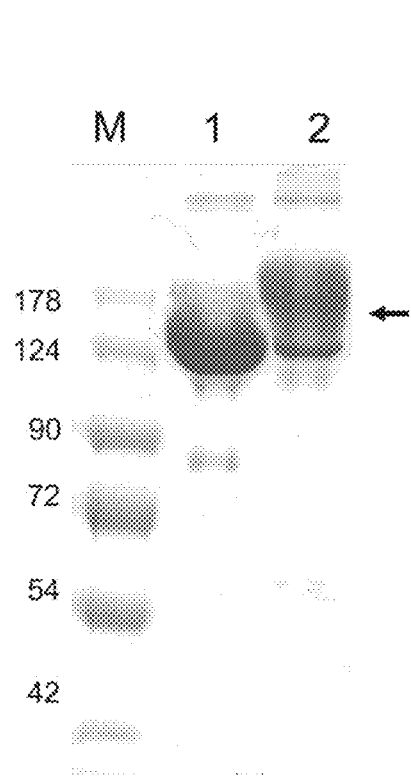
FIG. 14 shows the non-reducing SDS-PAGE analysis of recombinant 2-chain (scFv α CD19)-Fc-MBM-2×2 DOTA bundles according to one working example of the present invention.

FIG. 14 shows the result of the SDS-PAGE analysis of the present molecular construct, which indicates that the present molecular construct has a molecular weight of about 120 kDa (lane 2, indicated by an arrow), which is consistent with or slightly larger than the expected size. The non-conjugated fusion protein was in lane 1. As could be seen in FIG. 14, the yield of the conjugation of DOTA bundles to the recombinant 2-chain (scFv α CD19)-Fc-MBM-2 is approximately 90%.

Example 13

Preparation of Recombinant 2-Chain (scFv α CD19)-Fc-MBM-3×2 DOTA Bundles

In this example, the conjugation of two DOTA bundles to the recombinant 2-chain ($V_L$-$V_H$ scFv α CD19)-Fc-MBM-3 from Example 5 was performed as described in the preceding Example.

Figure 15:
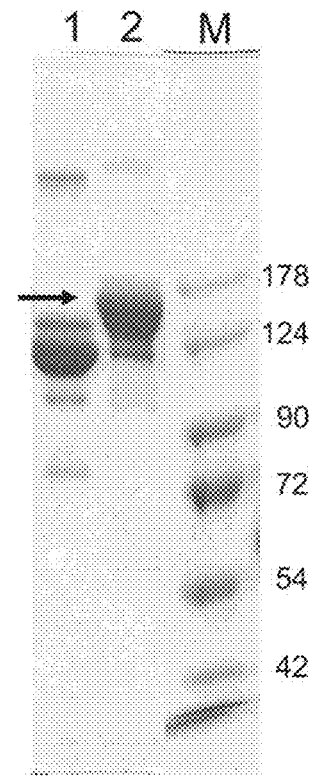
FIG. 15 shows the non-reducing SDS-PAGE analysis of recombinant 2-chain (scFv α CD19)-Fc-MBM-3×2 DOTA bundles

FIG. 15 shows the result of the SDS-PAGE analysis of the present molecular construct, which indicates that the present molecular construct has a molecular weight of about 120 kDa (lane 2, indicated by an arrow), which is consistent with or slightly larger than the expected size. The non-conjugated fusion protein was in lane 1. As could be seen in FIG. 15, the yield of the conjugation of DOTA bundles to the recombinant 2-chain (scFv α CD19)-Fc-MBM-3 is approximately 90%.

Example 14

Preparation of Anti-CD19 Antibody-MBM-1×2 DOTA Bundles

In this example, the conjugation of two DOTA bundles to the intact human anti-CD19 antibody fused with a C-terminal MBM-1 from Example 6 was performed as described in the preceding Example.

Figure 16:
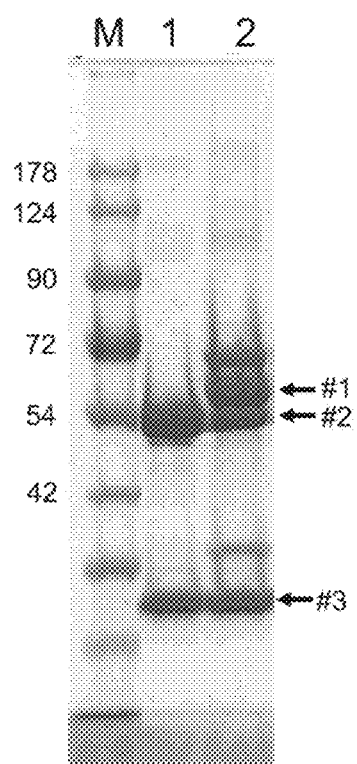
FIG. 16 shows the reducing SDS-PAGE analysis of the intact anti-CD19 antibody-MBM-1×2 DOTA bundles according to one working example of the present invention.

Shown in FIG. 16 is the SDS-PAGE analysis of the present molecular construct of anti-CD19 antibody-MBM-1×2 DOTA bundles. As indicated in FIG. 16, the heavy chain of the molecular weight is about 54 kDa (indicated by an arrow #1 in the lane 2), which is consistent with the expected size. Arrow #2 in the lane 2 is the non-conjugated heavy chain of the anti-CD19 antibody-MBM-1, and the arrow #3 is the light chain of the anti-CD19 antibody-MBM-1.

Example 15

Preparation of Anti-CD19 Antibody-MBM-2×2 DOTA Bundles

In this example, the conjugation of two DOTA bundles to the intact anti-CD19 antibody fused with a C-terminal MBM-2 from Example 6 was performed as described in the preceding Example.

Figure 17:
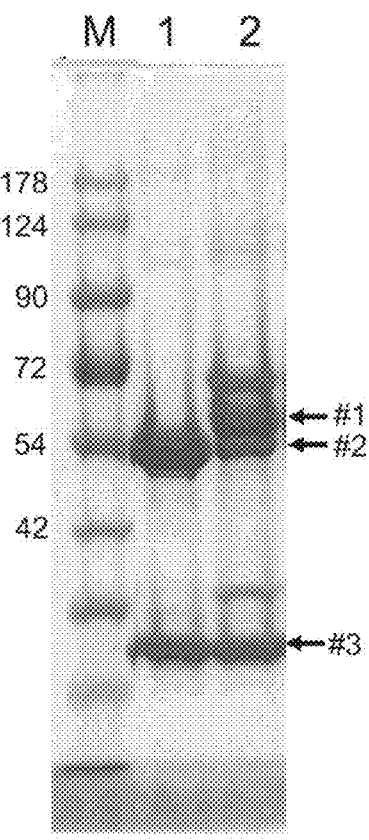
FIG. 17 shows the reducing SDS-PAGE analysis of the intact anti-CD19 antibody-MBM-2×2 DOTA bundles f according to one working example of the present invention.

Shown in FIG. 17 is the SDS-PAGE analysis of the present molecular construct. As indicated in FIG. 17, the molecular weight of the heavy chain is about 54 kDa (indicated by an arrow #1 in the lane 2), which is consistent with the expected size. Arrow #2 in the lane 2 is the non-conjugated heavy chain of the anti-CD19 antibody-MBM-2, and the arrow #3 is the light chain of the anti-CD19 antibody-MBM-2.

Example 16

Preparation of Recombinant 2-Chain (scFv α CD33)-Fc-MBM×2 DOTA Bundles

In this example, the conjugation of two DOTA bundles to the recombinant 2-chain ($V_L$-$V_H$ scFv α CD33)-Fc-MBM-1 or -MBM-2 from Example 7 was performed as described in the preceding Example.

Figure 18:
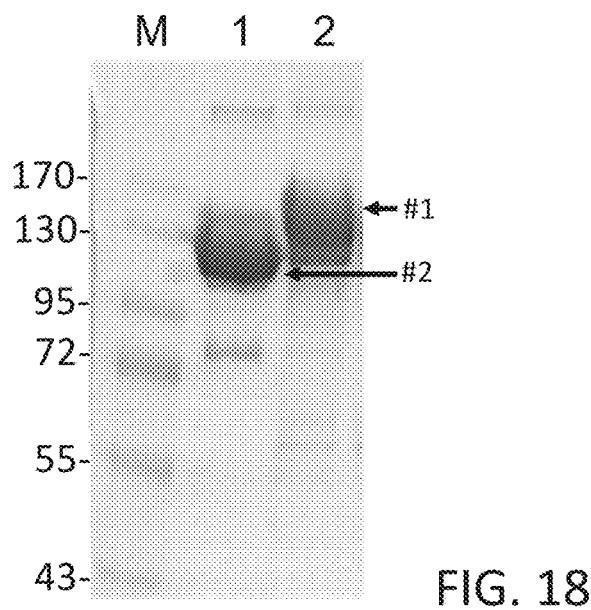
FIG. 18 shows the non-reducing SDS-PAGE analysis of recombinant 2-chain (scFv α CD33)-Fc-MBM-1×2 DOTA bundles according to one working example of the present invention.

FIG. 18 shows the result of the SDS-PAGE analysis of conjugation of DOTA bundles to the recombinant 2-chain (scFv α CD33)-Fc-MBM-1. As indicated in FIG. 18, this molecular construct has a molecular weight of about 120 kDa (indicated by an arrow #1 in the lane 2), which is consistent with or slightly larger than the expected size. Arrow #2 in the lane 1 is the non-conjugated fusion protein. The results of SDS-PAGE show that the yield of the conjugation of DOTA bundles to the recombinant 2-chain (scFv α CD33)-hIgG1.Fc-MBM-1 is approximately 65%.

Example 17

Preparation of Recombinant 2-Chain (scFv α CD20)-Fc-MBM-1×2 DOTA Bundles

In this example, the conjugation of two DOTA bundles to the recombinant 2-chain ($V_L$-$V_H$ scFv α CD20)-Fc-MBM-1 from Example 8 was performed as described in the preceding Example.

Figure 19:
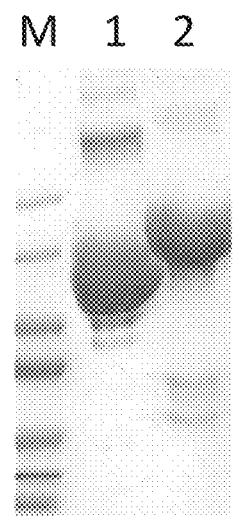
FIG. 19 shows the non-reducing SDS-PAGE analysis of recombinant 2-chain (scFv α CD20)-Fc-MBM-1×2 DOTA bundles according to one working example of the present invention.

FIG. 19 shows the result of the SDS-PAGE analysis of conjugation of DOTA bundles to the recombinant 2-chain (scFv α CD20)-Fc-MBM-1. As indicated in FIG. 19, this molecular construct has a molecular weight of about 120 kDa (indicated by an arrow #1 in the lane 2), which is consistent with or slightly larger than the expected size. Arrow #2 in the lane 2 is the non-conjugated fusion protein. The SDS-PAGE result in FIG. 19 also shows that the yield of the conjugation of DOTA bundles to the recombinant 2-chain (scFv α CD20)-Fc-MBM-1 is approximately 90%.

Example 18

Preparation of Recombinant 2-Chain (scFv α CA19-9)-Fc-MBM×2 DOTA

In this example, the conjugation of two DOTA bundles to the recombinant 2-chain (scFv α CA19-9)-Fc-MBM-1 or -MBM-3 from Example 9 was performed as described in the preceding Example. The results of SDS-PAGE show that the yields of the conjugation of DOTA bundles to the recombinant 2-chain (scFv α CA19-9)-Fc-MBM-1 and -MBM-3 are approximately 65% and 70%, respectively (data not shown).

Example 19

Stabilization of 2-Chain (scFv α CD19)-Fc-MBM-1×2 DOTA Bundles

To stabilize the 2-chain (scFv α CD19)-Fc-MBM-1×2 DOTA bundles, a ring opening reaction was carried out using the protocol as follows.

The reaction product of the molecular construct obtained in Example 14 was buffer exchanges into a Tris buffer (100 mM Tris at pH 9.0, 100 mM L-Arginine, and 100 mM sodium chloride) using a NAP-10 Sephadex G-25 column (GE Healthcare). The resulting solution was then heated to 37° C. for 5 hours. The solution was cooled and buffer-exchanged by centrifugation into 50 mM Bis-Tris buffer at pH 5.5. Final samples were concentrated to 1 to 3 mg/mL protein.

For purification, the stabilized product was adjusted to pH 5.5 and then applied to pre-equilibrated (50 mM Bis-Tris buffer at pH 5.5) Anion exchange column Hi-Trap™ Q HP (GE Healthcare). The stabilized 2-chain (scFv α CD19)-Fc-MBM-1×2 DOTA bundles was eluted using a step elution of 250 mM NaCl for 15 minutes and a linear gradient from 250 mM to 324 mM NaCl with a flow rate of 1.0 ml/min for 50 minutes.

An anion exchange column Q HP was ten used to separate the stabilized 2-chain (scFv α CD19)-Fc-MBM-1×2 DOTA bundles from free 2-chain fusion protein, the 2-chain fusion protein conjugated with three or four DOTA bundles, and aggregated material. The purified product, 2-chain (scFv α CD19)-Fc-MBM-1×2 DOTA bundles, was concentrated and buffer-exchange into Tris buffer (50 mM Tris buffer at pH 7.0 and 290 mM NaCl).

Figure 20:
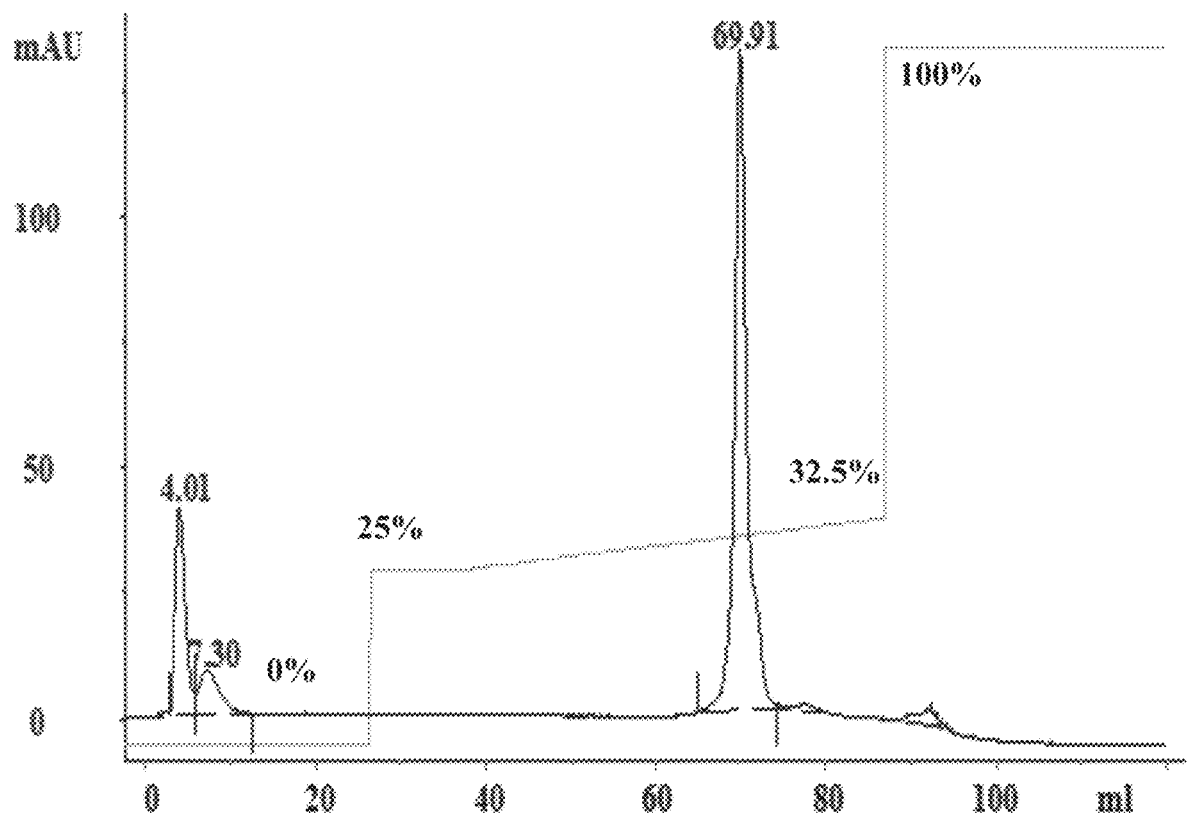
FIG. 20 shows the FPLC elution profile of anion exchange column on the stabilized 2-chain (scFv α CD19)-Fc-MBM-1×2 DOTA bundles according to one working example of the present invention.
Figure 21:
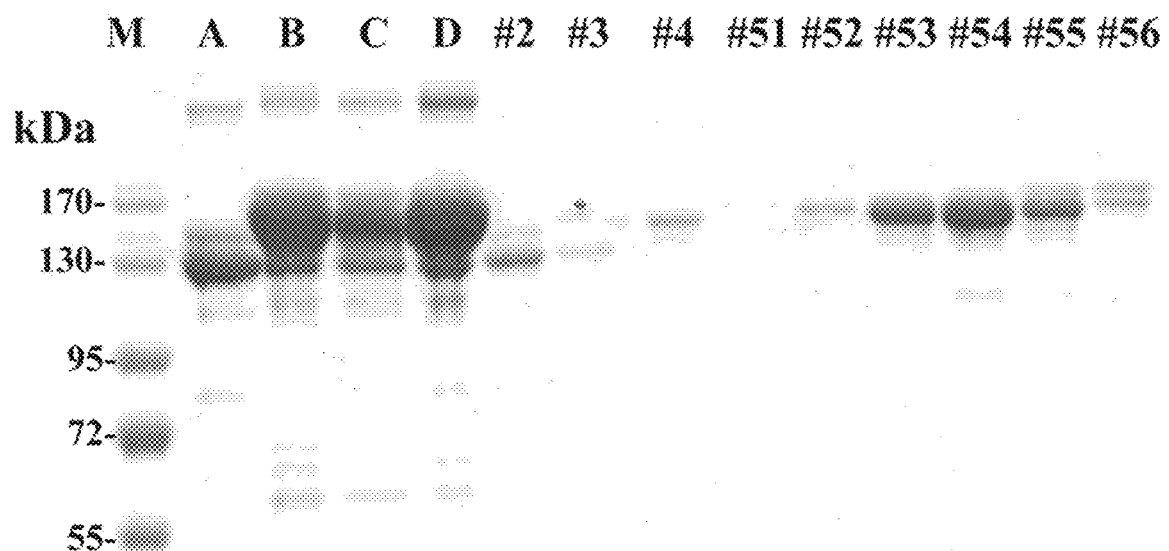
FIG. 21 shows the SDS-PAGE analysis of the fractions collected from anion exchange column on the stabilized 2-chain (scFv α CD19)-Fc-MBM-1×2 DOTA bundles according to one working example of the present invention.

FIG. 20 is the FPLC elution profile of anion exchange column Q HP on the stabilized 2-chain (scFv α CD19)-Fc-MBM-1×2 DOTA bundles. As shown in 20, the stabilized 2-chain (scFv α CD19)-Fc-MBM-1×2 DOTA bundles was eluted at the peak of 69.91 ml. FIG. 21 shows results of the SDS-PAGE analysis to fractions collected from anion exchange column Q HP. Lane A, B, C, and D respectively corresponds to non-conjugated molecular construct, molecular construct conjugated with DOTA bundles, the stabilized molecular construct conjugated with two DOTA bundles in the stock solution, and the stabilized molecular construct conjugated with two DOTA bundles before being loaded into the column.

The pure product, the stabilized 2-chain (scFv α CD19)-Fc-MBM-1×2 DOTA bundles, was collected from fraction #53, #54, and #55 shown in FIG. 21.

Example 20

Stabilization of 2-Chain (scFv α CD20)-Fc-MBM-1×2 DOTA Bundles

Purification of the stabilized 2-chain (scFv α CD20)-Fc-MBM-1×2 DOTA bundles

The procedure for stabilizing the 2-chain (scFv α CD20)-Fc-MBM-1×2 DOTA bundles was similar to the one described in Example 19.

For purification, the stabilized product was adjusted to pH 5.1 and then applied to pre-equilibrated (50 mM acetic acid at pH 5.1) Anion exchange column Hi-Trap™ Q HP (GE Healthcare). The stabilized 2-chain (scFv α CD20)-Fc-MBM-1×2 DOTA bundles was eluted using a step elution of 300 mM NaCl for 18 minutes and a linear gradient from 300 mM to 1000 mM NaCl with a flow rate of 1.0 ml/min for 80 minutes.

An anion exchange column Q HP was ten used to separate the stabilized 2-chain (scFv α CD20)-Fc-MBM-1×2 DOTA bundles from free 2-chain fusion protein, the 2-chain fusion protein conjugated with three or four DOTA bundles, and aggregated material.

Figure 22:
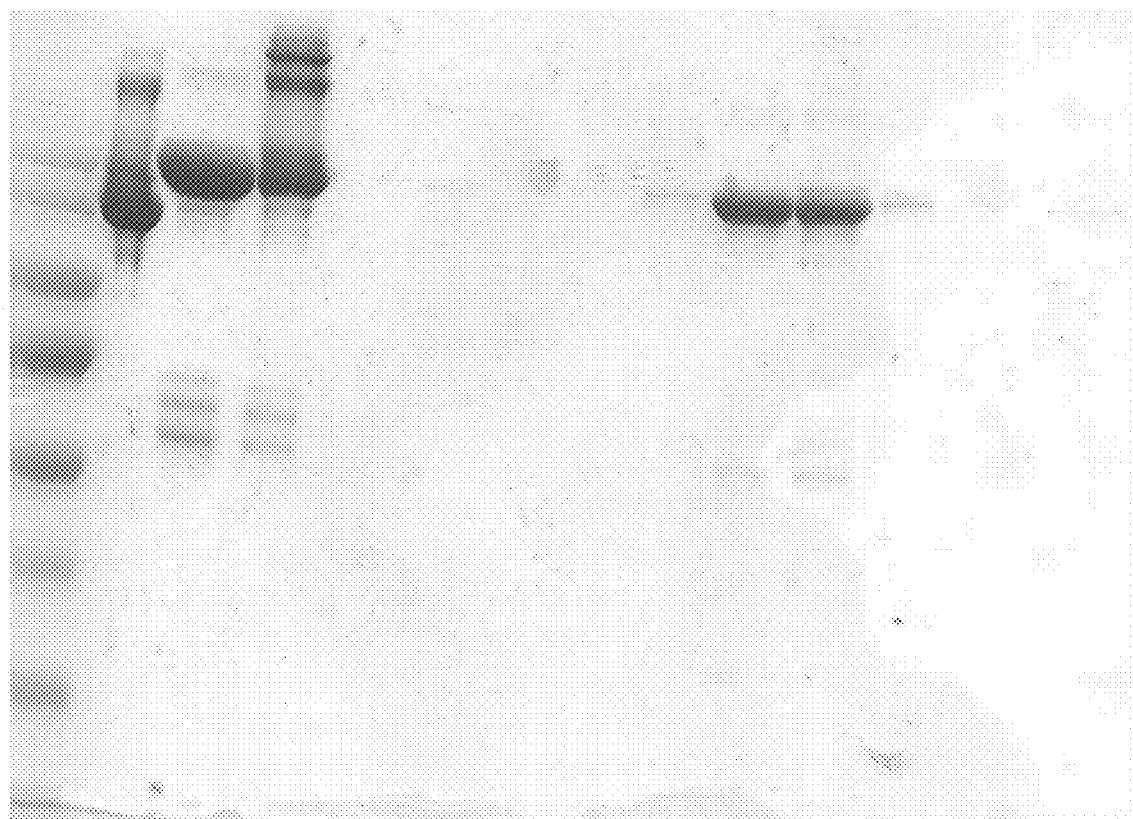
FIG. 22 shows the SDS-PAGE analysis of the fractions collected from anion exchange column on the stabilized 2-chain (scFv α CD20)-Fc-MBM-1×2 DOTA bundles according to one working example of the present invention.

FIG. 22 shows results of the SDS-PAGE analysis to fractions collected from anion exchange column Q HP. Lane A, B, and C respectively corresponds to non-conjugated molecular construct, molecular construct conjugated with DOTA bundles, and the stabilized molecular construct conjugated with two DOTA bundles before being loaded into the column.

The pure product, the stabilized 2-chain (scFv α CD20)-Fc-MBM-1×2 DOTA bundles, was collected from fraction #40 and #41 shown in FIG. 22.

Example 21

MALDI-TOF Analysis of Stabilized 2-Chain (scFv α CD19)-Fc-MBM-1×2 DOTA Bundles

Figure 23:
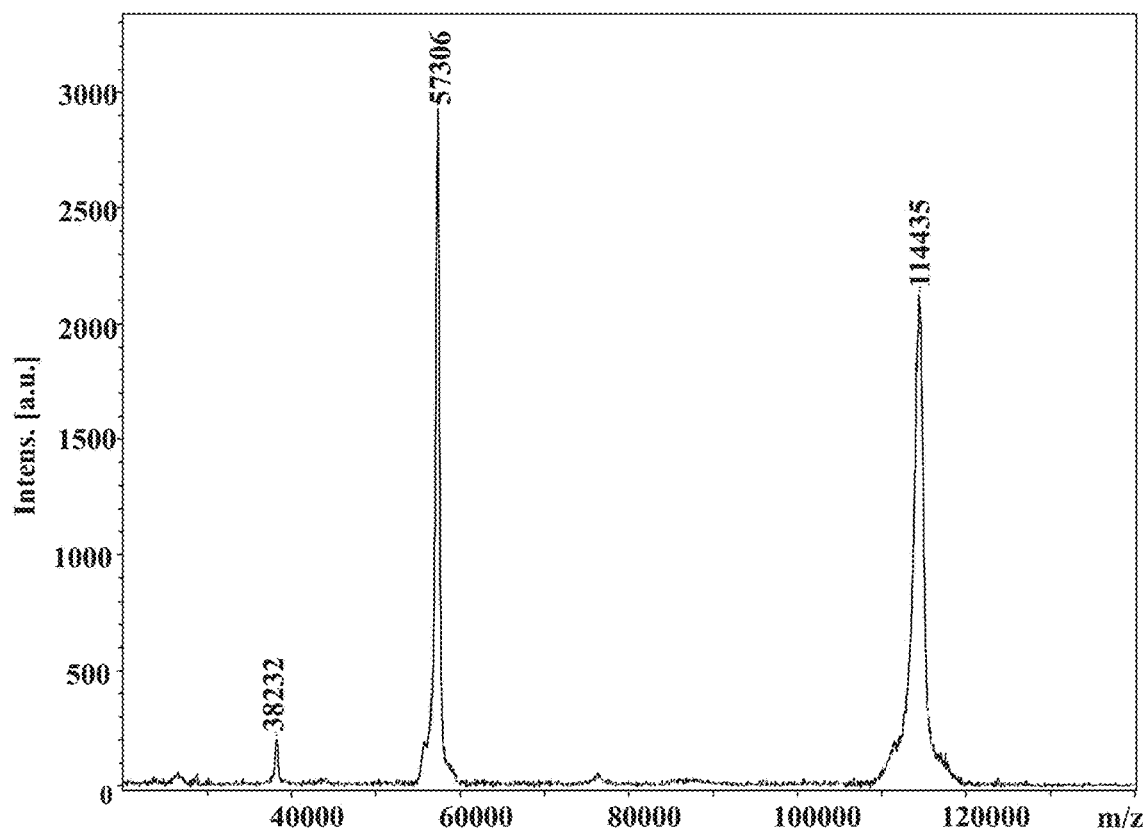
FIG. 23 is the MALDI-TOF result of the stabilized 2-chain (scFv α CD19)-Fc-MBM-1×2 DOTA bundles according to one working example of the present invention.

The stabilized 2-chain (scFv α CD19)-Fc-MBM-1×2 DOTA bundles from Example 19 was analyzed using mass spectroscopy MALDI-TOF. MALDI-TOF result in FIG. 23 shows that the sample of the stabilized 2-chain (scFv α CD19)-Fc-MBM-1×2 DOTA bundles has a molecular weight of 114,435 and 57,306 daltons, respectively corresponding to m/z (z=1): $[M+H]^+$ and m/z (z=2): $[M+2H]^{2+}$.

Example 22

Preparation of $^{89}$Y-Labeled 2-Chain (scFv α CD19)-Fc-MBM-1×2 DOTA Bundles

Figure 24:
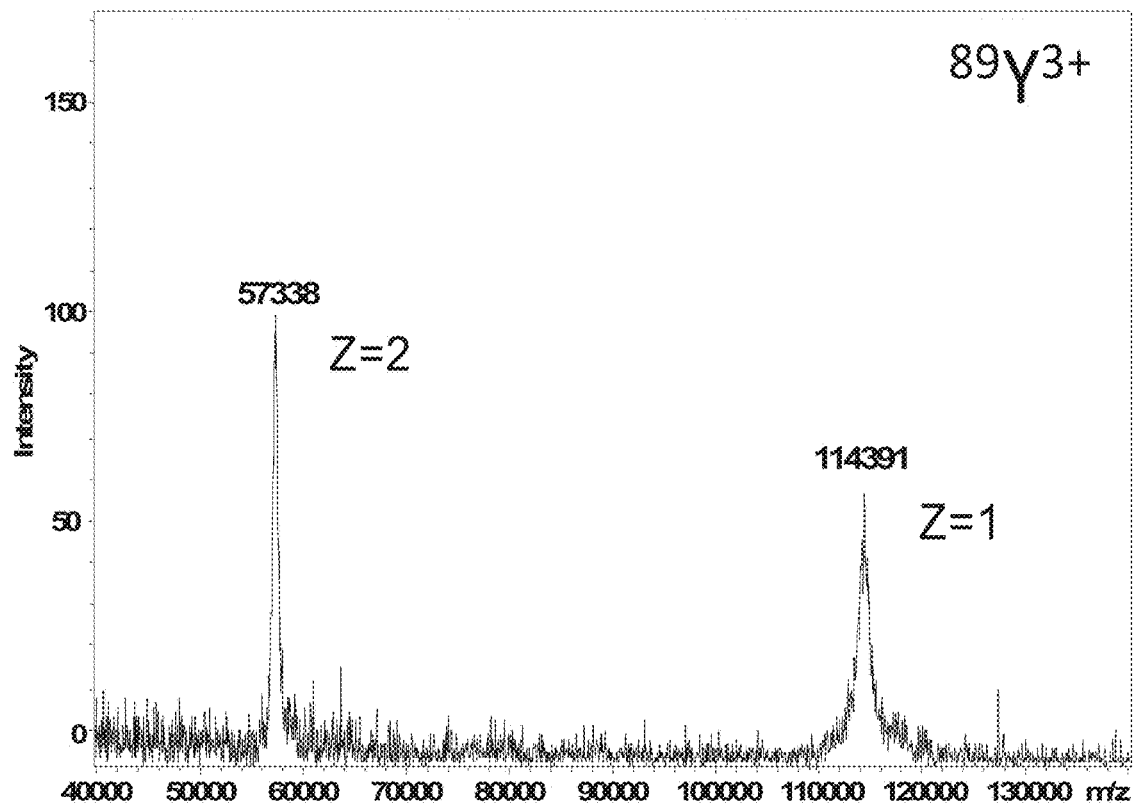
FIG. 24 is the MALDI-TOF result of the stabilized 2-chain (scFv α CD19)-Fc-MBM-1×2 DOTA bundles chelated with $8\gamma^{3+}$ ion according to one working example of the present invention.

In this example, $Y(NO_3)_3$ solution was added to a solution of the purified stabilized 2-chain (scFv α CD19)-Fc-MBM-1×2 DOTA bundles from Example 19 at a 6:1 [$Y^{3+}$ ion: protein] molar ratio; the reaction mixture was incubated for 6 hours at room temperature. Free $Y^3$ ions were removed from the solution using NAP-10 Sephadex G-25 column. The stabilized 2-chain (scFv α CD19)-Fc-MBM-1×2 DOTA bundles chelated with $[^{89}Y]^3$ was analyzed using mass spectroscopy MALDI-TOF. The MALDI-TOF result in FIG. 24 indicates that the present molecular construct has a molecular weight of 114,391 daltons.

Example 23

Preparation of $^{175}$Lu-Labeled 2-Chain (scFv α CD19)-Fc-MBM-1×2 DOTA Bundles

Figure 25:
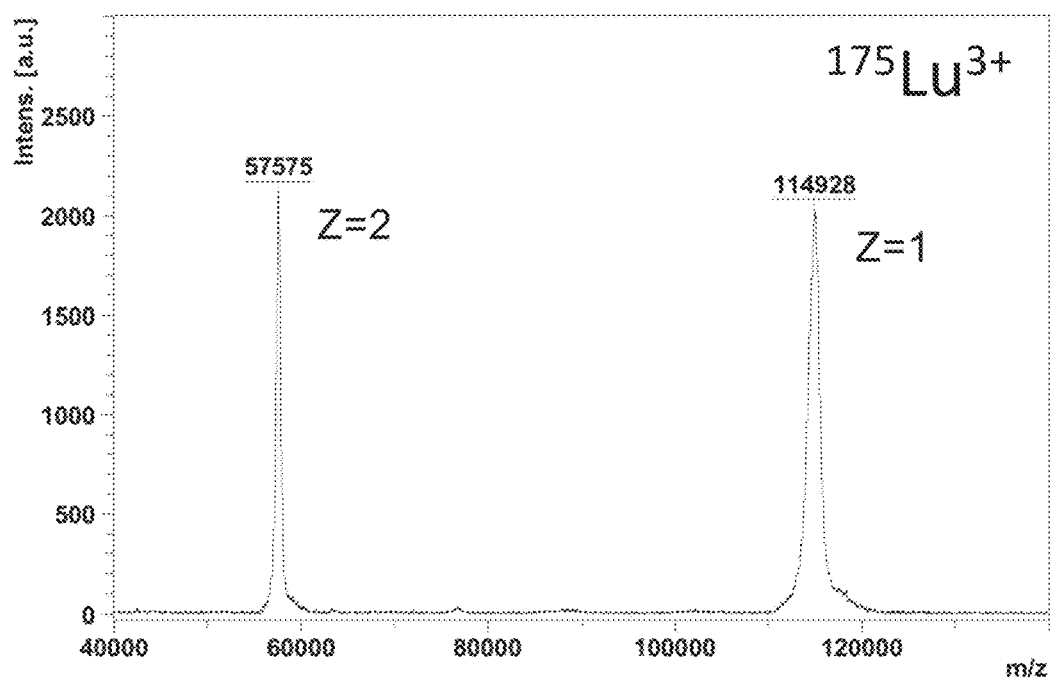
FIG. 25 is the MALDI-TOF result of the stabilized 2-chain (scFv α CD19)-Fc-MBM-1×2 DOTA bundles chelated with $^{175}Lu^{3+}$ ion according to one working example of the present invention.

In this example, $LuCl_3$ solution was added to a solution of the purified stabilized 2-chain (scFv α CD19)-Fc-MBM-1×2 DOTA bundles at a 60:1 [$Lu^{3+}$ ion:protein] molar ratio; the reaction mixture was then incubated at 45° C. for 1.5 hours to afford the 75Lu-DOTA-protein chelate. Free $Lu^{3+}$ ions were removed from the solution by spinning filtration (Amicon centrifugal filter, kDa). The stabilized 2-chain (scFv α CD19)-Fc-MBM-1×2 DOTA bundles chelated with two $^{175}$Lu was analyzed using MALDI-TOF mass spectroscopy. The MALDI-TOF result in FIG. 25 shows that the present molecular construct has a molecular weight of 114,928 daltons.

Example 24

Preparation of $^{111}$In-Labeled 2-Chain (scFv α CD19)-Fc-MBM-1×2 DOTA Bundles

For the preparation of $^{111}$In-labeled fusion protein, an aliquot of carrier-free $^{111}$In 50 mM HCl was transferred to a tube, and twenty-volume of metal-free 0.1M HEPES buffer was added to adjust the pH of the solution to 4.5. Then, a solution of 2-chain (scFv α CD19)-Fc-MBM-1×2 DOTA bundles (30-50 μg) in 0.1M HEPES buffer (pH 4.5) was added to a final concentration of protein at 0.3-0.6 mg/mL. The resultant solution was gently mixed and incubated at 40-45° C. for 60 minutes. Diethylenetriaminepentaacetic acid (DTPA) was added in an amount of 1000 times the amounts of protein to capture the free $^{111}$In$^{3+}$ ions and quench the reaction. After incubation at 37° C. for 30 minutes, the $^{111}$In-DTPA chelates was removed from $^{111}$In-labeled product and the solvent was replaced with 0.9% saline by spinning filtration (Amicon centrifugal filter, 10 kDa).

Specific activities of the collected $^{111}$In-labeled product were determined by measuring the radioactivity of an appropriate aliquot of the sample using a γ-counter.

Example 25

Figure 26:
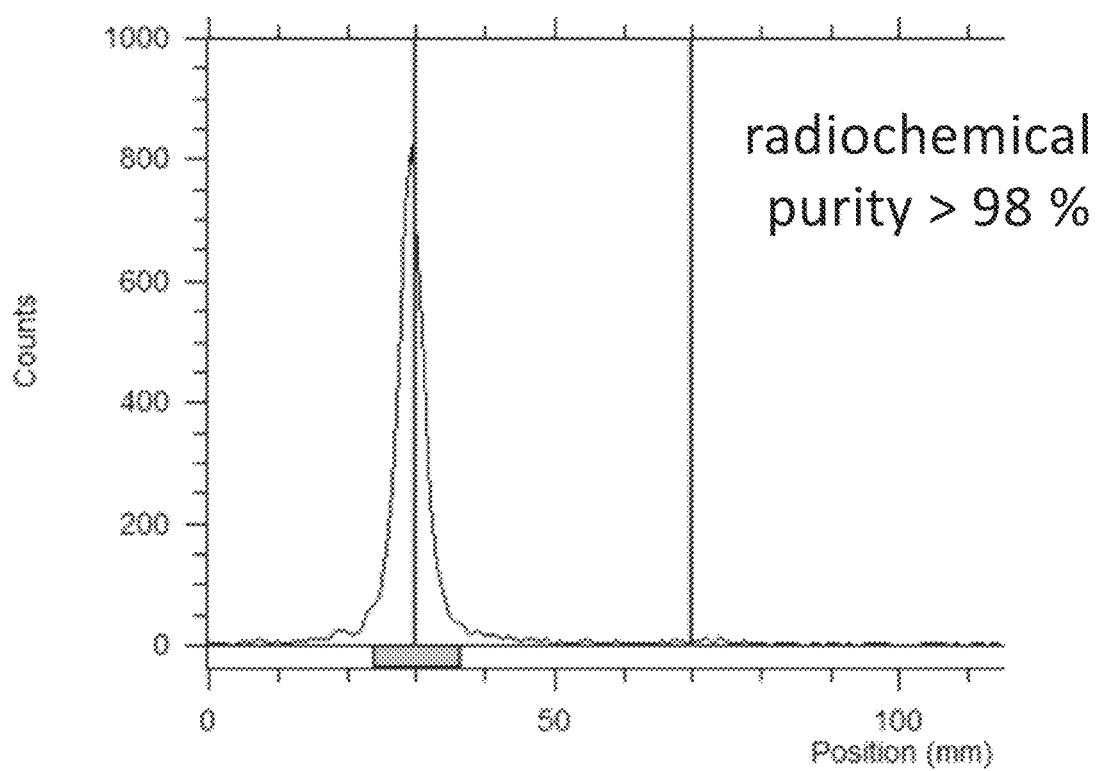
FIG. 26 is the TLC analysis result of radiochemical purity of the stabilized 2-chain (scFv α CD19)-Fc-MBM-1×2 DOTA bundles labeled with $^{111}In$ according to one working example of the present invention.

Radio-Incorporation Assay of $^{111}$In-Labeled 2-Chain (scFv α CD19)-Fc-MBM-1×2 DOTA Bundles Radiochemical purity assessment was carried out with instant thin-layer chromatography (iTLC). The solution of radiolabeled product from Example 24 was diluted 1:10 or 1:20 with the original solvent; then 1 μL of the sample was spotted on one end of a 1×10 cm strip of TLC SG paper. The paper was developed using ascending chromatography using 0.5M sodium citrate (pH 4.5). Radioactivity was determined using a radio-TLC scanner. The protein-associated radioactivity was expressed as a percentage of the total radioactivity. As shown in FIG. 26, the radiochemical purity of $^{111}$In labeled 2-chain (scFv α CD19)-Fc-MBM-1×2 DOTA bundles is greater than 98%.

Example 26

Stability Test of $^{111}$In-Labeled 2-Chain (scFv α CD19)-Fc-MBM-1×2 DOTA Bundles in Serum The in vitro stability of $^{111}$In-labeled 2-chain (scFv α CD19)-Fc-MBM-1×2 DOTA bundles was assessed in mouse serum at 37° C. for 96 hours. The $^{111}$In-labeled molecular construct from Example 24 was suspended in 0.2M ammonia acetate (pH 5). The $^{111}$In-labeled molecular construct was diluted 1:10 with mouse serum and then incubated at 37° C. for a period up to 96 hours. At selected time points (0, 12, 24, 48 and 96 hours), the $^{111}$In-labeled molecule was removed and analyzed using radio-TLC as described in the Example 25.

Figure 27:
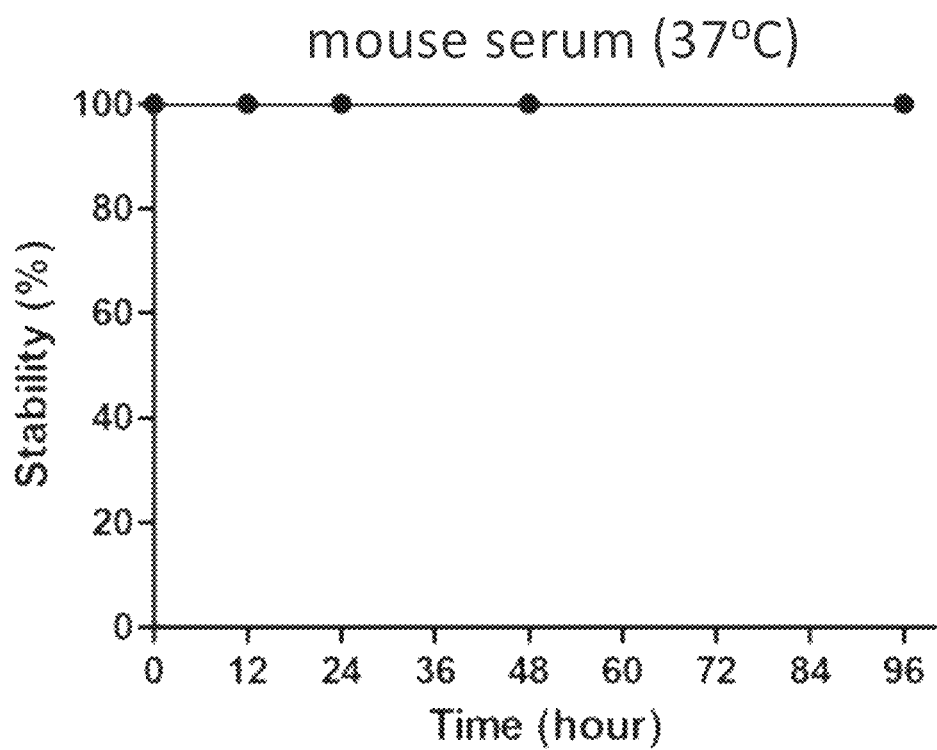
FIG. 27 shows the result of the stability test of the $^{111}In$-laneled stabilized 2-chain (scFv α CD19)-Fc-MBM-1×2 DOTA bundles analyzed by western blotting according to one working example of the present invention.
Figure 28A:
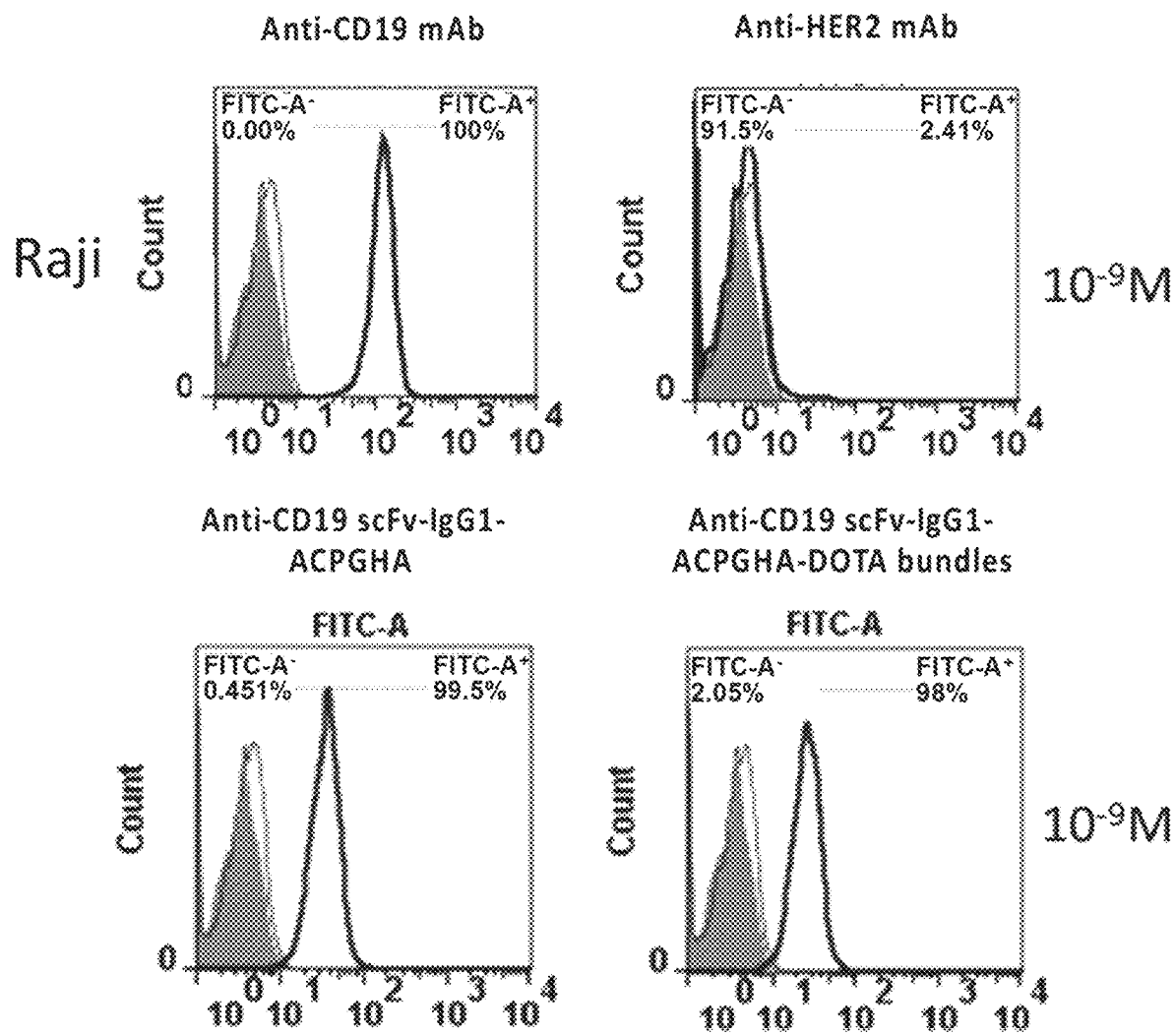
FIG. 28A to FIG. 28D show the results of the staining analysis of the stabilized 2-chain (scFv α CD19)-Fc-MBM-1×2 DOTA bundles according to one working example of the present invention.
Figure 28B:
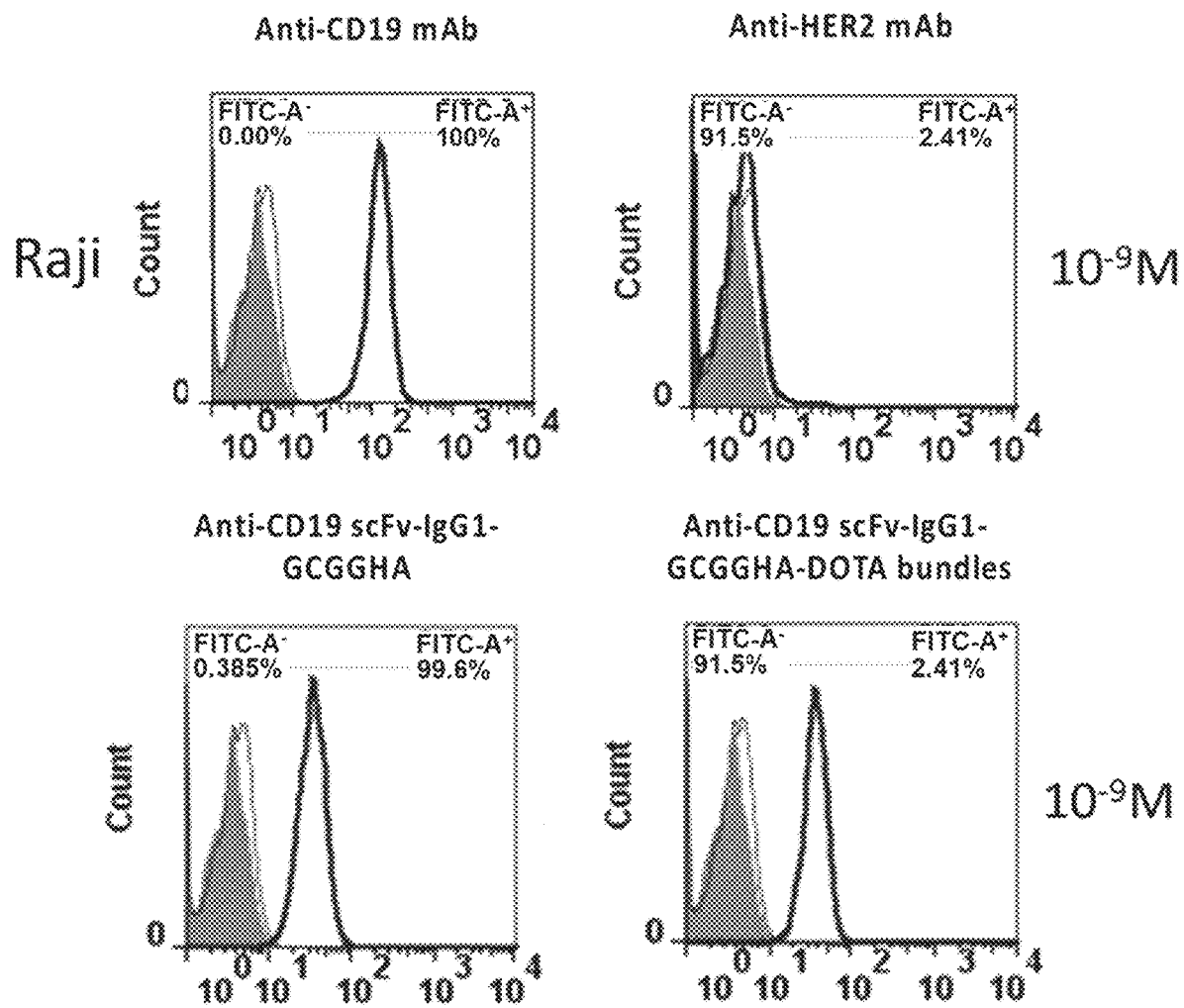
Figure 28C:
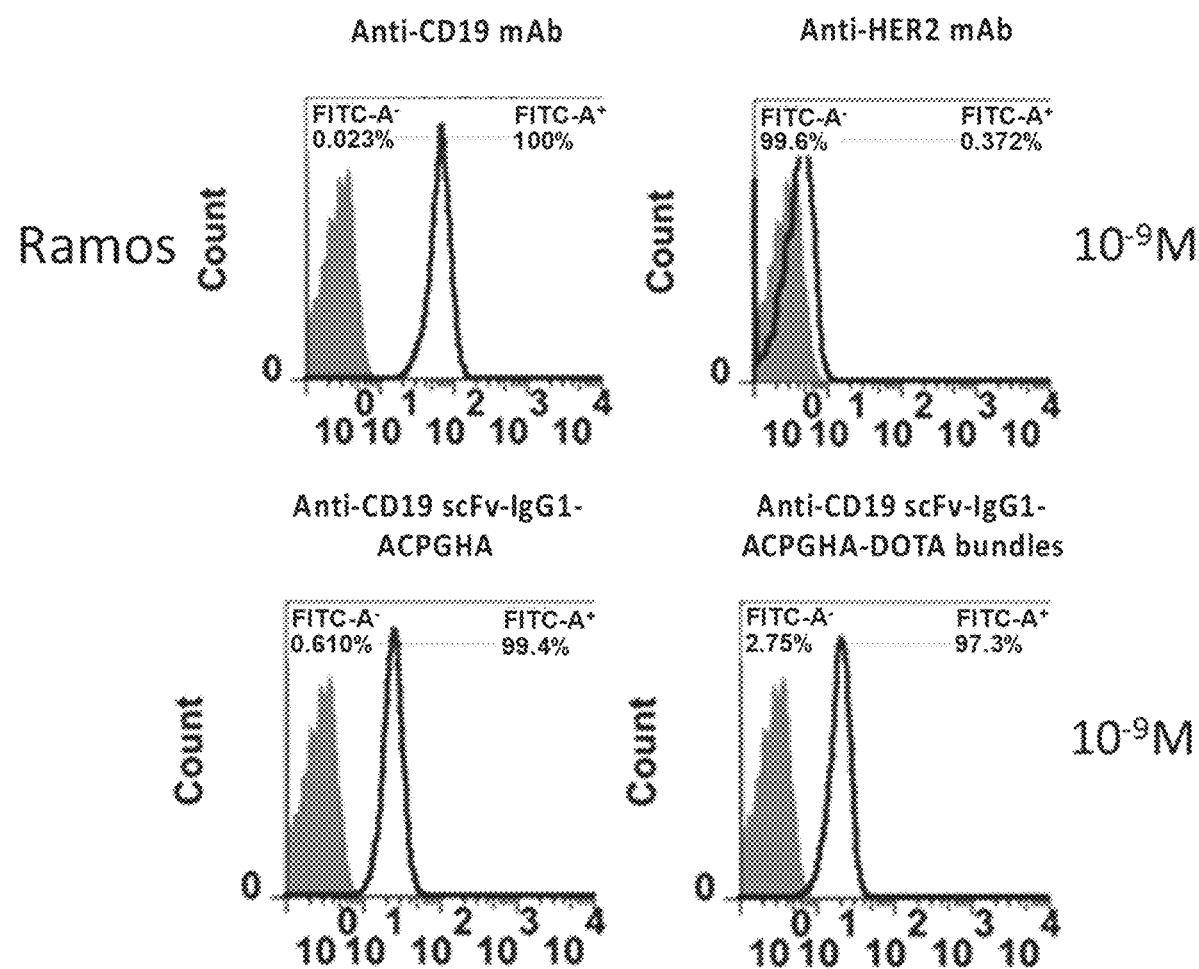
Figure 28D:
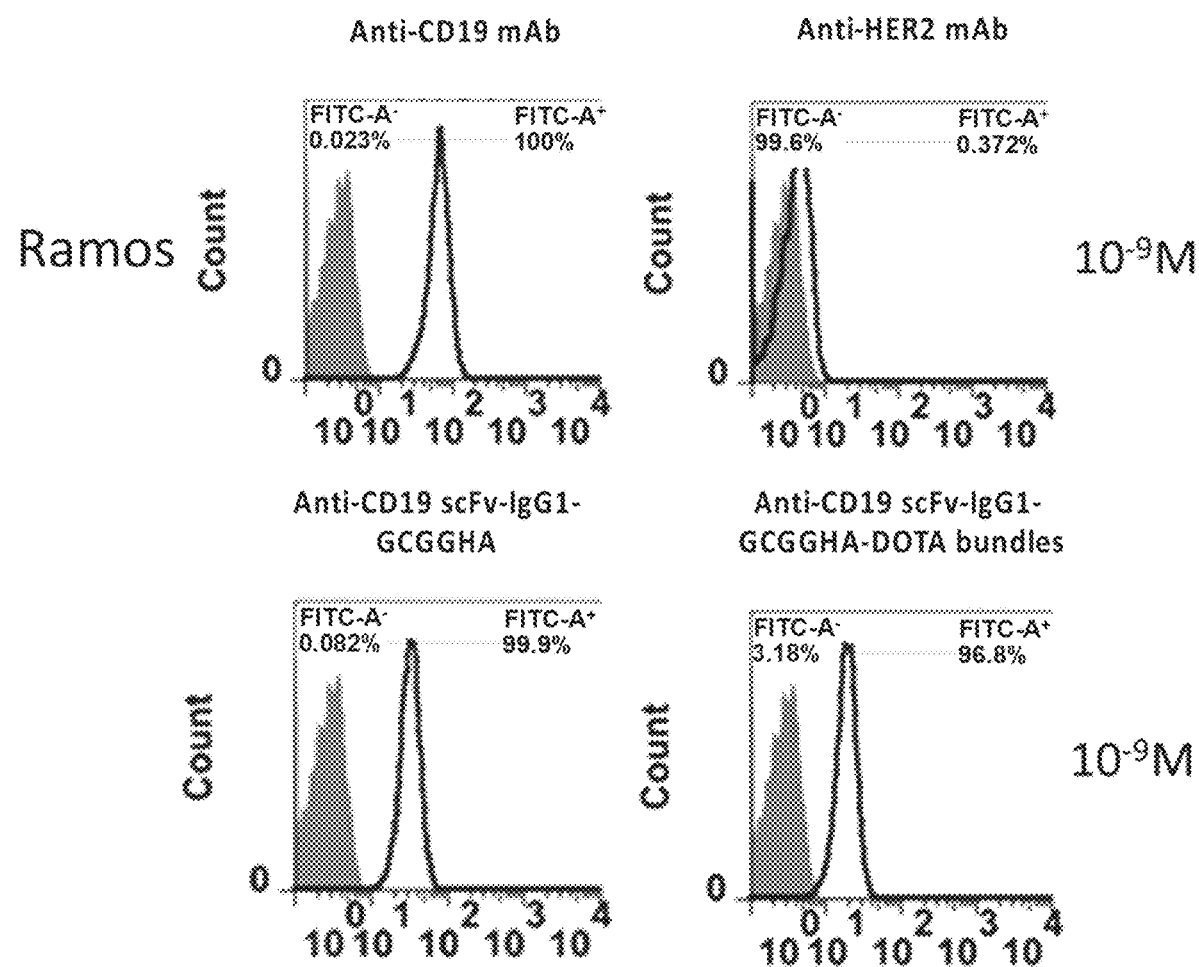

As shown in FIG. 27, the $^{111}$In-labeled 2-chain (scFv α CD19)-Fc-MBM-1×2 DOTA bundles exhibits satisfactory stability while being incubated in mouse serum at 37° C. for 96 hours.

Example 27

Site-Specific Conjugation of Recombinant 2-Chain (scFv α CD19)-Fc-MBM-1×2 DOTA Bundles In order to identify the cysteine residue of the 2-chain (scFv α CD19)-Fc-MBM-1 that is conjugated with the DOTA bundle, the sample was digested and analyzed using LC-MS. Briefly, 5 μl of the sample (0.4 μg/mL) from Example 11 was diluted in the solution containing 15 μl of 25 mM tetraethylammonium tetrahydroborate (TEAB) and 2 μl of 200 mM TCEP, and incubated at 55° C. for 1 hour. Then, the reaction mixture was added by 2 μl of 375 mM iodoacetic acid (IAA) at room temperature for 30 minutes. After the alkylation by IAA, the enzymes, trypsin and Glu-C, were added into the solution at 37° C. overnight for enzymatic digestion.

The mass spectrometric analysis result (data not shown) shows that the m/z value of the fragment in the MS spectrum corresponds to 4,530.99 daltons, which matches the molecular weight of the fragment containing the amino acid sequence of SLSLSPGGGGACPGHA (amino acid residues 468-483 of SEQ ID NO: 13) of the molecular construct and one DOTA bundle.

Example 28

Binding Activity of Stabilized 2-Chain (scFv α CD19)-Fc-MBM-1×2 DOTA Bundles to Human B Lymphoma Cell Lines Two stabilized molecular constructs, (scFv α CD19)-Fc-MBM-1×2 DOTA bundles and (scFv α CD19)-Fc-MBM-3×2 DOTA bundles, were analyzed for their ability to bind to human CD19 on human B lymphoma cell line Raji. The assay was performed by incubating 1×10⁶CD19-expressing Raji cells with 0.001 μg/ml of each construct in PBS, 1% BSA on ice for 30 minutes, using anti-CD19 antibody (RB4v1.2), (scFv α CD19)-Fc-MBM-1×2 DOTA bundles and (scFv α CD19)-Fc-MBM-3×2 DOTA bundles as positive controls. The anti-HER2 antibody (trastuzumab) was used as a negative control. The staining of cells was analyzed by FACS (FACSCanto II; BD Biosciences) using FITC-conjugated goat anti-human IgG.Fc (diluted 1:200 in PBS/BSA) (Caltag, Buckingham, UK) at 4° C. for 20 minutes in the dark. FIGS. 27A and 27B show results of the cell staining analysis of the two molecular constructs containing MBM-1 and MBM-3 on CD19-expressing Raji cells, respectively, which indicate that these two constructs bound to Raji cells substantially positively.

These molecular constructs were also analyzed for their ability to bind to human CD19 on human B lymphoma cell lines Ramos. The assay was performed using the protocol similar to the one used in cell binding assay with Raji cells. The staining of Ramos cells was analyzed by FACS (FACSCanto II; BD Biosciences) using FITC-conjugated goat anti-human IgG.Fc, where anti-CD19 IgG is used as a positive control. The anti-HER2 antibody (trastuzumab) was used as a negative control. FIGS. 27C and 27D show results of the cell staining analysis of the two molecular constructs containing MBM-1 and MBM-3 on CD19-expressing Ramos cells, respectively. These two constructs bound to Ramos cells substantially positively.

Example 29

Stability of Stabilized 2-Chain (scFv α CD19)-Fc-MBM-1×2 DOTA Bundles

To evaluate the stability of the stabilized 2-chain (scFv α CD19)-Fc-MBM-1×2 DOTA bundles, the molecular constructs were placed in Tris buffer (100 mM Tris buffer at pH 7.3, 50 mM Bis-Tris buffer, and 290 mM NaCl) with glutathione or human serum albumin, and then incubated at 37° C. for 30 days.

Figure 29:
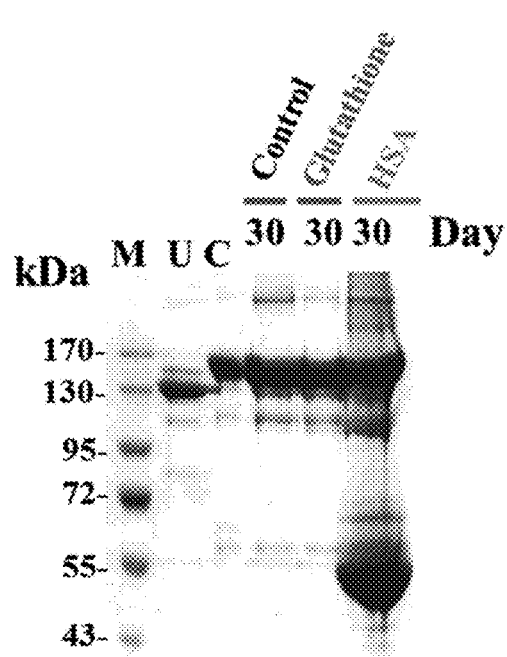
FIG. 29 shows the result of the stability test of the stabilized 2-chain (scFv α CD19)-Fc-MBM-1×2 DOTA bundles analyzed by SDS-PAGE according to one working example of the present invention.

As shown in FIG. 29, the stabilized 2-chain (scFv α CD19)-Fc-MBM-1×2 DOTA bundles exhibits satisfactory stability while being incubated with glutathione or human serum albumin (HSA) at 37° C. for 30 days. As could be seen in FIG. 28, in both glutathione and HAS-treated groups, approximately 90% of the intact molecular construct was still in the solution without retro-Michael addition product. Lane U and C respectively correspond to non-conjugated molecular construct and the stabilized 2-chain (scFv α CD19)-Fc-MBM-1×2 DOTA bundles stocked at 4° C. as controls.

Example 30

Examination of Retro-Michael Addition Product of Stabilized 2-Chain (scFv α CD19)-Fc-MBM-1×2 DOTA Bundles A further confirmation of the stability of the 2-chain (scFv α CD19)-Fc-MBM-1×2 DOTA bundles, the stabilized molecular construct was incubated with glutathione or HSA and then analyzed using Western blot.

For the western blot analysis of the stabilized samples, briefly, the samples were separated on 8% SDS-PAGE gels and transferred to a poly(vinylidene fluoride) (PVDF) membrane (Millipore). The membrane blots were blocked in PBS containing 5% BSA and 0.05% Tween 20 for 1 hour at room temperature. After washing 3 times with phosphate buffered saline tween-(PBST) containing PBS and 0.05% Tween-20, the blots were incubated with goat anti-human IgG.Fc antibody conjugated with horseradish peroxidase (Millipore). Then the membranes were washed 3 times with PBST, and immunoreacted bands were detected using ECL™ western blotting detection reagents (Millipore) and exposed on Fujifilm (Tokyo, Japan).

Figure 30:
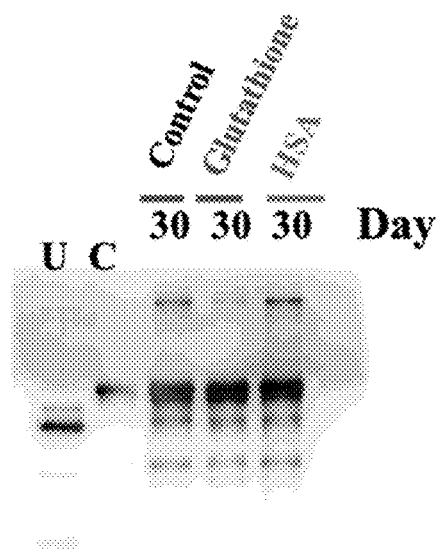
FIG. 30 shows the result of the stability test of the stabilized 2-chain (scFv α CD19)-Fc-MBM-1×2 DOTA bundles analyzed by TLC according to one working example of the present invention.

FIG. 30 shows the result of the stabilized 2-chain (scFv α CD19)-Fc-MBM-1×2 DOTA bundles by western blot analysis. As shown in FIG. 29, the stabilized 2-chain (scFv α CD19)-Fc-MBM-1×2 DOTA bundles exhibits satisfactory stability while being incubated with glutathione or HSA at 37° C. for 30 days, compared with the stabilized molecular construct stocked at 4° C. (lane C). Lane U is the non-conjugated molecular construct as a control.

Example 31

Half-Life of Stabilized 2-Chain (scFv α CD19)-Fc-MBM-1×2 DOTA Bundles

The measurement of half-lives of the stabilized 2-chain (scFv α CD19)-Fc-MBM-1×2 DOTA bundles was carried out in mice after i.v. administration. The (scFv α CD19)-Fc-MBM-1×2 DOTA bundles in the serum sample was observed using ELISA. 8 to 10-week-old BALB/c mice were purchased from BioLasco, Taipei, Taiwan. Mice were grouped into three mice per group, and were injected intravenously with about 200 μL of 3.33 μM protein.

Figure 31:
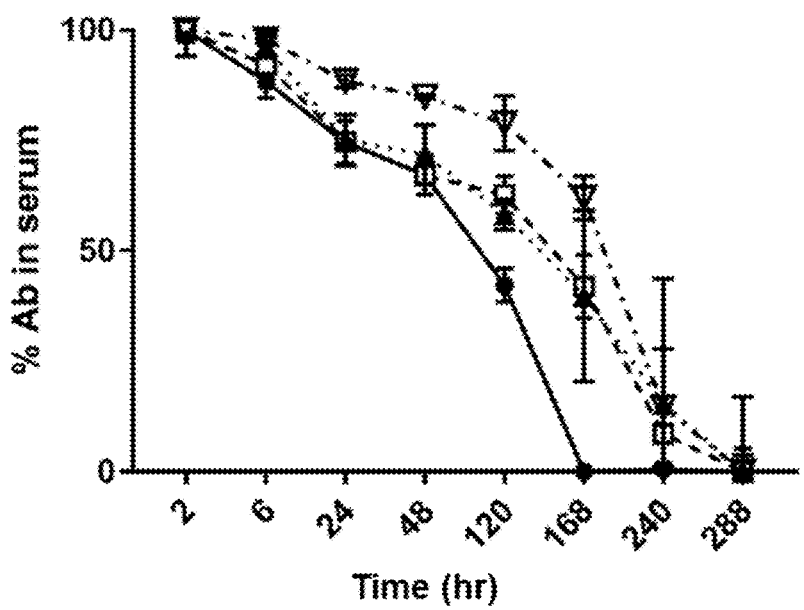
FIG. 31 shows the half-lives of the stabilized 2-chain (scFv α CD19)-Fc-MBM-1×2 DOTA bundles according to one working example of the present invention.

The pharmacokinetic profiles of anti-CD19 antibody (RB4v1.2), the 2-chain (scFv α CD19)-Fc-MBM-1 fusion protein, as shown in FIG. 31, indicate that the half-lives of anti-CD19 antibody (RB4v1.2), the (scFv α CD19)-Fc-MBM-1 fusion protein from Example 3, the molecular construct of (scFv α CD19)-Fc-MBM-1×2 DOTA bundles from Example 18, and the stabilized the molecular construct of (scFv α CD19)-Fc-MBM-1×2 DOTA bundles From Example 19 are about 129, 179.6, 153.6, and 193.5 hours, respectively. In conclusion, the stabilization treatment results in a prolonged half-live of the stabilized molecular construct.

Example 32

Targeting Effect of the Stabilized 2-Chain (scFv α CD19)-Fc-MBM-1×2 DOTA Bundles to CD19-Expressing Xenograft Tumor In this Example, in vivo imaging system (IVIS) was used to investigate the targeting effect of the stabilized 2-chain (scFv α CD19)-Fc-MBM-1×2 DOTA bundles to CD19-expressing tumors in mouse xenograft model. Prior to IVIS imaging, a Dylight 680 Antibody Labeling Kit (Thermo Scientific) was used to conjugate the stabilized 2-chain (scFv α CD19)-Fc-MBM-1×2 DOTA bundles from Example 19 and the anti-CD19 antibody (RB4v1.2), according to the manufacturer's instructions.

8 to 10-week-old NOD-SCID (NOD.CB17-Prkdc$^{scid}$/JNarl) were purchased from Laboratory Animal Facility of Institute of Cellular and Organismic Biology, Academia Sinica, Taipei, Taiwan. The mice were injected intraperitoneally with 1×10$^7$ B-cell lymphoma Raji cells per mouse 2 weeks before the treatment. The mice were grouped into three mice per group, and were injected intravenously with about 200 μL of 6.65 μM labeled molecule. At various time points, mice were anaesthetized with isoflurane in O$_2$ and placed in the IVIS Spectrum In Vivo Imaging System (PerkinElmer) with a supine position. Fluorescent images were captured with ex/em=675/720, using the Living Image Software V3.2. Images were captured at indicated time points using IVIS Spectrum imager and analyzed with Living Image software.

Figure 32:
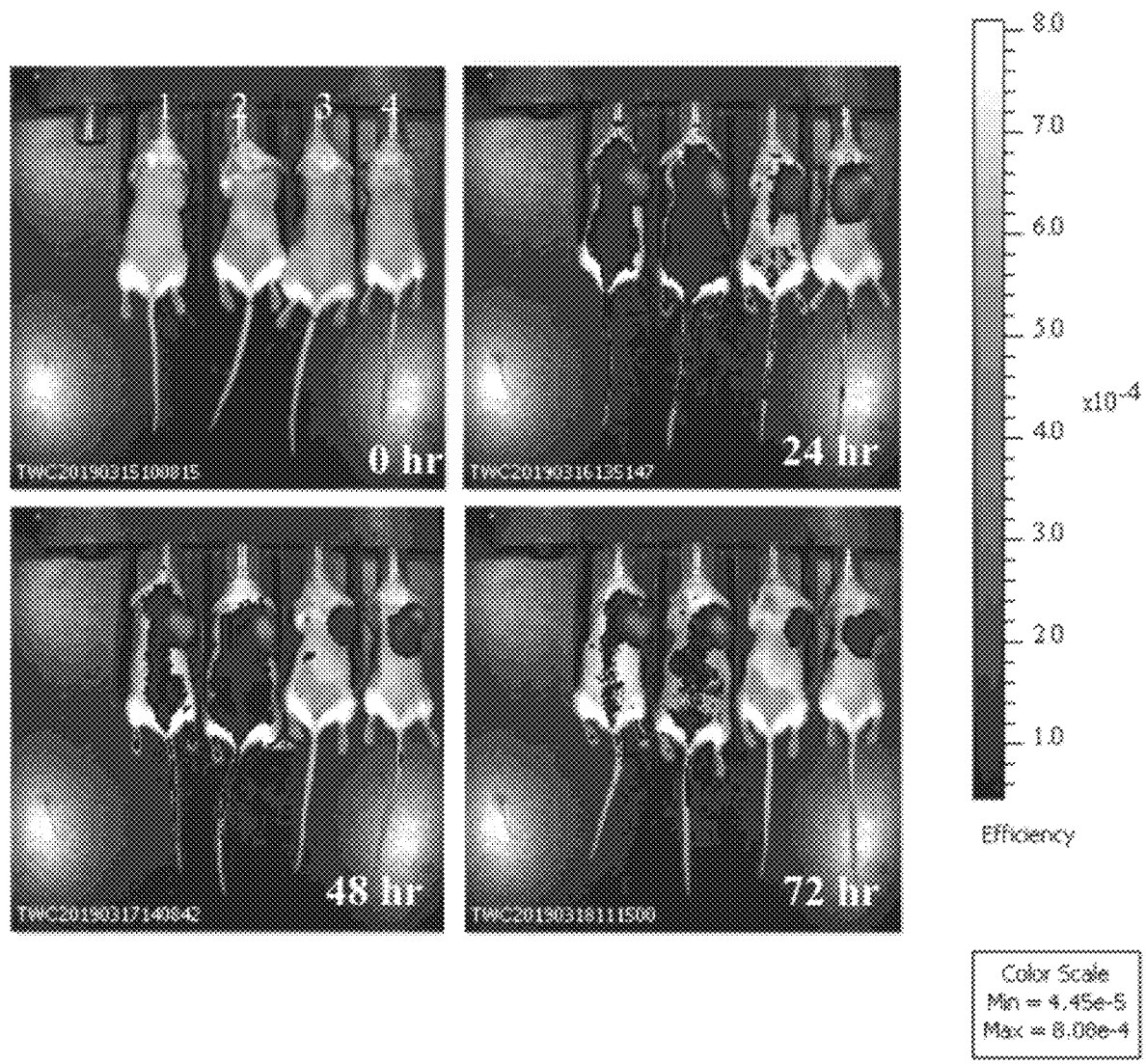
FIG. 32 shows the targeting effect of the stabilized 2-chain (scFv α CD19)-Fc-MBM-1×2 DOTA bundles to CD19-expressing xenograft tumor according to one working example of the present invention.

Fluorescent images from NOD-SCID mice were captured and analyzed at 0 hour, 24 hours, 48 hours, and 72 hours after the administration of DyLight 680-conjugated proteins. FIG. 32 shows the distribution of the fluorescence-labeled molecules in mouse model. NOD-SCID mice were intravenously injected with anti-CD19 antibody (RB4v1.2) (1 and 2) and the stabilized 2-chain (scFv α CD19)-Fc-MBM-1×2 DOTA bundles (3 and 4).

As shown in FIG. 32, at 24, 48, and 72 hours after the i.v. injection, the penetration of the stabilized 2-chain (scFv α CD19)-Fc-MBM-1×2 DOTA bundles and the anti-CD19 antibody (RB4v1.2) into tumors located on the right side is significantly greater than that observed with normal organ on the left side. Thus, the stabilized molecular construct exhibits satisfactory targeting effect to CD19-expressing tumors in mouse xenograft model.

Example 33

Biodistribution of Stabilized 2-Chain (scFv α CD19)-Fc-MBM-1×2 DOTA Bundles in CD19-Expressing Xenograft Tumor For biodistribution analysis of the stabilized (scFv α CD19)-Fc-MBM-1×2 DOTA bundles in xenograft mouse model, the procedure set forth in Example 32 was used with some modifications.

Briefly, the mice were injected subcutaneously with 1×10$^7$ B-cell lymphoma Raji cells per mouse 2 to 3 weeks before the treatment. The mice were grouped into three mice per group, and were injected intravenously with about 200 μL of 6.65 μM labeled molecule.

Biodistribution of NOD-SCID mice were analyzed by tissue ELISA at 7 days after the administration of the stabilized 2-chain (scFv α CD19)-Fc-MBM-1×2 DOTA bundles and the anti-CD19 antibody. Briefly, the animals were sacrificed at day 7 after injection. Blood was hemospasia from the heart, and tissue samples from 11 organs were collected. Tissues samples were homogenized using homogenizer and analyzed further for measuring the concentration of the injected molecules by ELISA.

Figure 33:
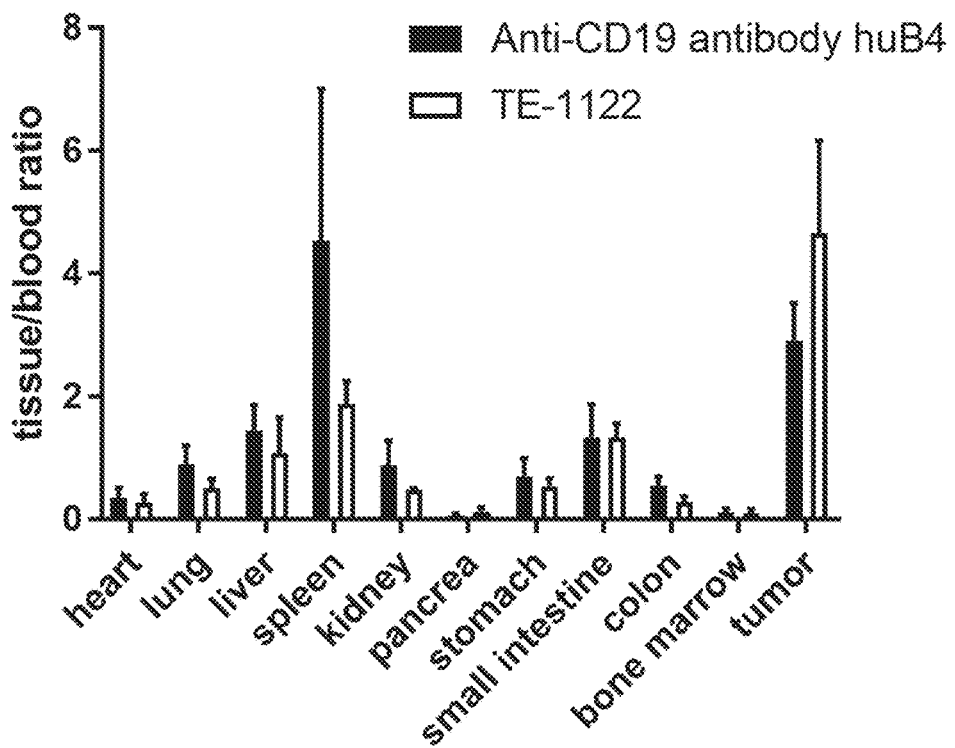
FIG. 33 shows the result of the biodistribution analysis of the stabilized 2-chain (scFv α CD19)-Fc-MBM-1×2 DOTA bundles in CD19-expressing xenograft tumor according to one working example of the present invention.

FIG. 33 shows the distribution of the stabilized 2-chain (scFv α CD19)-Fc-MBM-1×2 DOTA bundles (TE-1122) in the mouse model. The y-axis of the biodistribution diagram represents the tissue-to-blood ratio. The result also shows that the stabilized molecular construct can target CD19-expressing tumors in the mouse xenograft model.

Example 34

Synthesis of Aib-GLP-1 Agonist Having a Terminal Cysteine Residue

Figure 34:
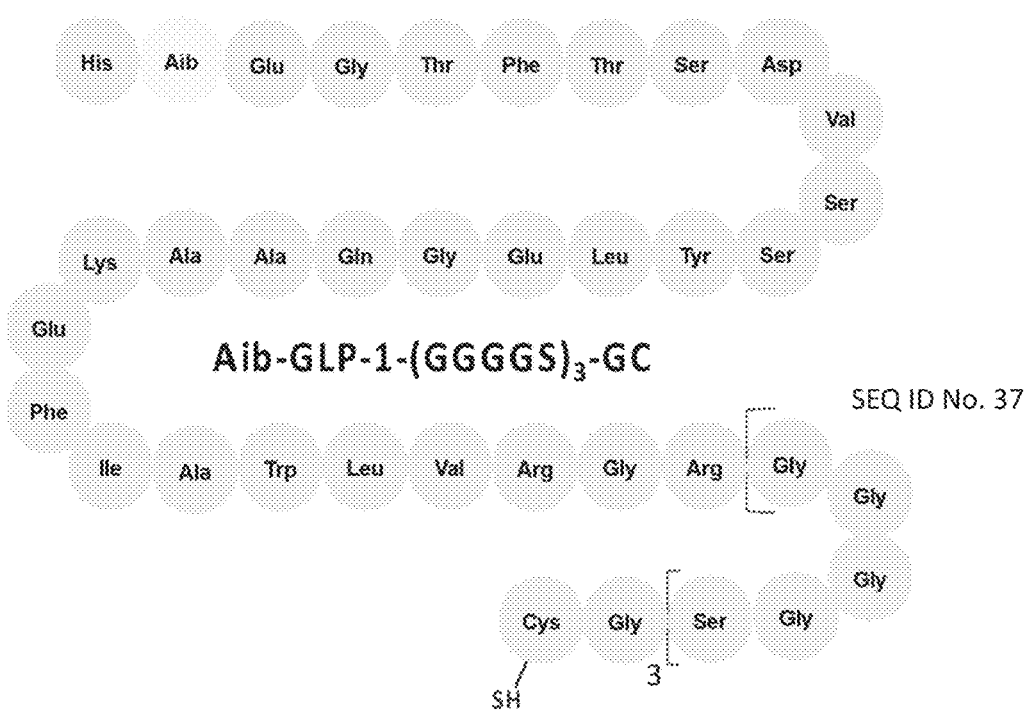
FIG. 34 is a schematic diagram showing the structure of the Aib-GLP-1 agonist-Cys according to one working example of the present invention.

In this example, an ε-aminobutyric acid (Aib)-substituted glucagon-like peptide-1 (GLP-1) agonist having a free cysteine in the C-terminal end was prepared; the amino acid sequence of this Aib-GLP-1 agonist-Cys molecular construct is described in SEQ ID NO: 37. FIG. 34 is a schematic diagram illustrating the structure of this molecular construct. Like semaglutide, the second amino acid residue is substituted with the Aib (or U) residue to improve the resistance to dipeptidyl peptidase IV (DPP 4) degradation; yet, in this molecular construct, a flexible linker of 15 amino acid residues (amino acid residues 31 to 45 of SEQ ID NO: 37) are introduced before the last glycine residue of the semaglutide (i.e., amino acid residue 46 of SEQ ID NO: 37), and a terminal cysteine residue is added to the C-terminus.

The structure of the Aib-GLP-1 agonist-Cys was designed by the present inventors, and the synthesis was outsourced to Shanghai WuXi AppTech Co., Ltd. (Shanghai, China).

The purified sample of Aib-GLP-1 agonist-Cys was analyzed using reverse phase analytical HPLC on a Supelco C18 column (250 mm×4.6 mm; 5 µm), with a mobile phase of acetonitrile and 0.1% trifluoroacetic acid, a linear gradient of 0% to 100% acetonitrile over 30 minutes, at a flow rate of 1.0 ml/min and a column temperature of 25° C.

The identification of the Aib-GLP-1 agonist-Cys product was carried out using mass spectrometry ESI-MS. The sample of the Aib-GLP-1 agonist-Cys product shows a strong molecular ion at 1,483.4, which corresponds to [M+H]*, indicating that the actual molecular weight of the present Aib-GLP-1 agonist-Cys agonist is 1,482.4 daltons.

Example 35

Synthesis of Somatostatin Analog Having a Terminal Cysteine Residue

Figure 35:
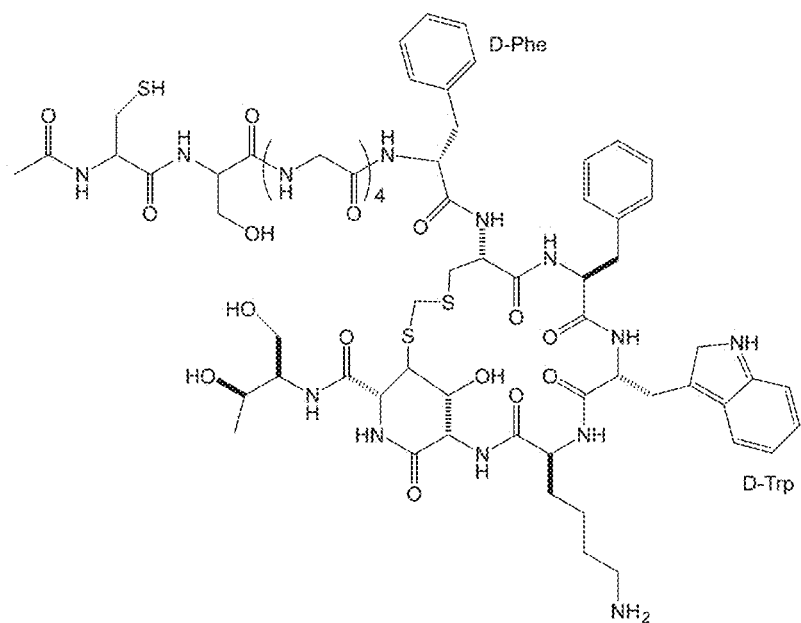
FIG. 35 is a schematic diagram showing the structure of the Cys-octreotide according to one working example of the present invention.

In this example, a somatostatin analog having a free cysteine in the N-terminal end was prepared; the amino acid sequence of this Cys-octreotide molecular construct is described in SEQ ID NO: 38. FIG. 35 is a schematic diagram illustrating the structure of this molecular construct. This molecular construct has 14 amino acid residues, in which an N-terminal Cysteine residue is introduced, followed by a flexible linker of 5 amino acid residues and the octreotide sequence. Like the original octreotide, the seventh amino acid residues (Phe) and the tenth amino acid residue (Trp) of the present Cys-octreotide molecular construct are in D-forms, a disulfide bridge is formed between the eight and thirteen cysteine residues, and the C-terminus threonine residue is in the form of threoninol. Additionally, the N-terminus of the Cys-octreotide molecular construct is modified with an acetyl group.

The structure of the present Cys-octreotide molecular construct was designed by the present inventors, and the synthesis synthesized by a standard solid phase method, which was outsourced to Ontores Biotechnologies Co., Ltd. (Hangzhou, China). The Cys-octreotide product has a purity of greater than 95%.

Figure 36:
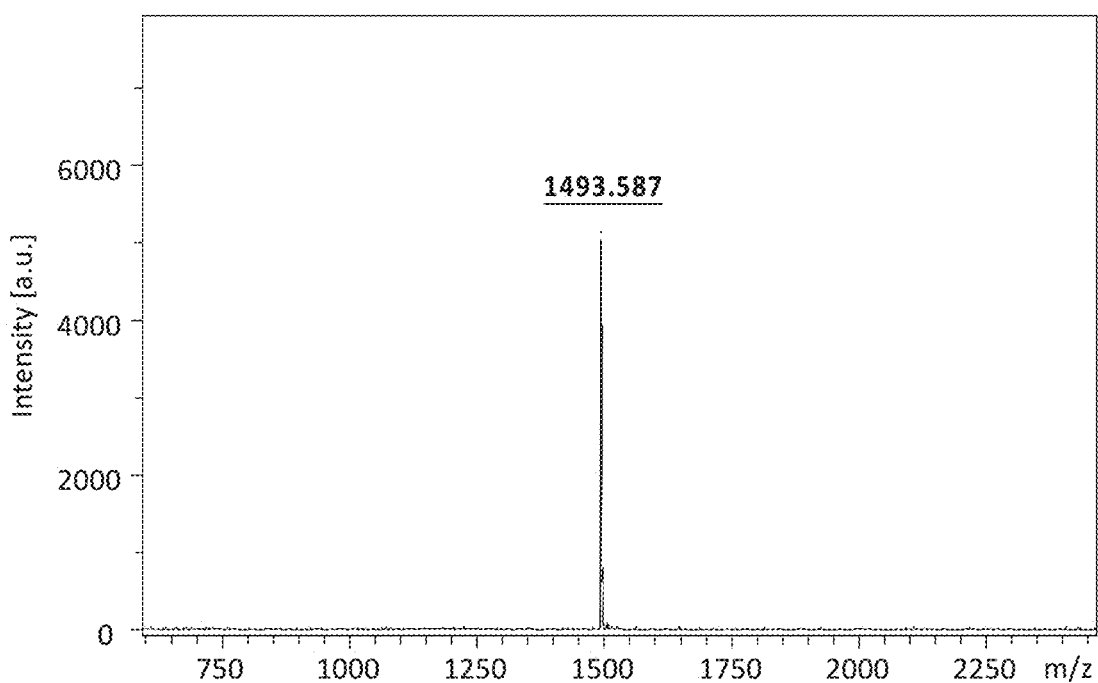
FIG. 36 shows the MALDI-TOF/TOF result of the Cys-octreotide according to one working example of the present invention.

The identification of the Cys-octreotide product was carried out using mass spectrometry MALDI-TOF. Mass spectrometry analyses were performed at the Mass Core Facility at the Institute of Molecular Biology (IMB), Academia Sinica, Taipei, Taiwan. Measurements were performed on a Bruker Autoflex III MALDI-TOF/TOF mass spectrometer (Bruker Daltonics, Bremen, Germany). FIG. 36 shows the result of mass spectrometry MALDI-TOF, which indicates that the present molecular construct has a molecular weight of 1,493.587 daltons.

Example 36

Synthesis of PSMA Ligand Having a Cysteine Residue

In this example, a PSMA ligand containing a free cysteine residue was prepared, the structure of this molecular construct is provided in FIG. 37.

The structure of the present Cys-PSMA ligand molecular construct was designed by the present inventors, and the synthesis was outsourced to Shanghai WuXi AppTech Co., Ltd. (Shanghai, China). The Cys-PSMA ligand product has a purity of greater than 95.0%.

The identification of the Cys-PSMA ligand was carried out using mass spectrometry ESI-MS. FIG. 38 shows the result of mass spectrometry ESI-MS, which indicates that the present molecular construct has a strong molecular ion at 522.4, which corresponds to [M+H]*, indicating that the actual molecular weight of the Cys-PSMA ligand is 521.4 daltons.

Example 37

Synthesis of Calcitonin-MBM-1

In this example, a molecular construct of calcitonin having a metal binding motif at its C-terminus was prepared; the amino acid sequence of this calcitonin-MBM-1 molecular construct is described in SEQ ID NO: 39. FIG. 39 is a schematic diagram illustrating the structure of this molecular construct. Like calcitonin, a disulfide bridge is formed between the first and the seventh cysteine residues; yet, in this molecular construct, a flexible linker of 8 amino acid residues (amino acid residues 33 to 40 of SEQ ID NO: 39) are introduced after the last proline residue of calcitonin (i.e., amino acid residue 32 of SEQ ID NO: 39), and the MBM-1 motif (ACPGHA, SEQ ID NO: 7) is added to the C-terminus of the flexible linker.

The structure of the present calcitonin-MBM-1 molecular construct was designed by the present inventors, and the synthesis was outsourced to Shanghai WuXi AppTech Co., Ltd. (Shanghai, China).

Example 38

Synthesis of Teriparatide-MBM-1

In this example, a molecular construct of teriparatide having a metal binding motif at its C-terminus was prepared; the amino acid sequence of this teriparatide-MBM-1 molecular construct is described in SEQ ID NO: 40. Teriparatide is a form of parathyroid (PTH) hormone consisting of the first 34 amino acids, which is the active portion of the hormone. It is used in the treatment of some forms of osteoporosis. In the teriparatide-MBM-1 molecular construct, a flexible linker of 15 amino acid residues (amino acid residues 35 to 49 of SEQ ID NO: 40) are introduced after the last phenylalanine residue of teriparatide (i.e., amino acid residue 34 of SEQ ID NO: 40), and the MBM-1 motif (ACPGHA, SEQ ID NO: 7) is added to the C-terminus of the flexible linker.

The structure of the present teriparatide-MBM-1 molecular construct was designed by the present inventors, and the synthesis was outsourced to Shanghai WuXi AppTech Co., Ltd. (Shanghai, China).

Example 39

Synthesis of Leuprolide-MBM-3

In this example, a molecular construct of leuprolide having a metal binding motif at its C-terminus was prepared; the amino acid sequence of this leuprolide-MBM-3 molecular construct is described in SEQ ID NO: 41. Leuprolide (also known as leuprorelin) is a gonadotropin-releasing hormone (GnRH) analogue acting as an agonist at pituitary GnRH receptors, which is used in the treatment of prostate cancer and breast cancer. The commercially available leuprolide is an oligopeptide having nine amino acid residues. In the present leuprolide-MBM-3 molecular construct, a flexible linker of 8 amino acid residues (amino acid residues 10 to 17 of SEQ ID NO: 41) are introduced after the last proline residue of calcitonin (i.e., amino acid residue 9 of SEQ ID NO: 41), and the MBM-3 motif (GCGGHA, SEQ ID NO: 6) is added to the C-terminus of the flexible linker.

The structure of the present leuprolide-MBM-3 molecular construct was designed by the present inventors, and the synthesis was outsourced to Shanghai WuXi AppTech Co., Ltd. (Shanghai, China). The identification of the synthesized peptide was carried out using mass spectrometry ESI-MS. The result of mass spectrometry ESI-MS indicates that the present molecular construct has a strong molecular ion at 1,091.97, which corresponds to $[M+2H]^2$, indicating that the actual molecular weight of the leuprolide-MBM-3 molecular construct is 2,181.35 daltons.

Example 40

Syntheses of Lenalidomide Bundles

In this example, two drug bundles having a maleimide-containing peptide with three lysine residues as the center core and three lenalidomide molecules conjugated with the center core were designed by the present investors. The present Lenalidomide bundle was synthesized using the combined method, where the standard Fmoc-based solid-phase synthesis was carried out for synthesizing the center core, and then the liquid-phase synthesis was conducted for conjugating lenalidomide molecules modified with a linking arm to the sidechain of the lysine residues in the center core. The manufacture was outsourced Shanghai WuXi AppTech Co., Ltd. (Shanghai, China).

Figure 40:
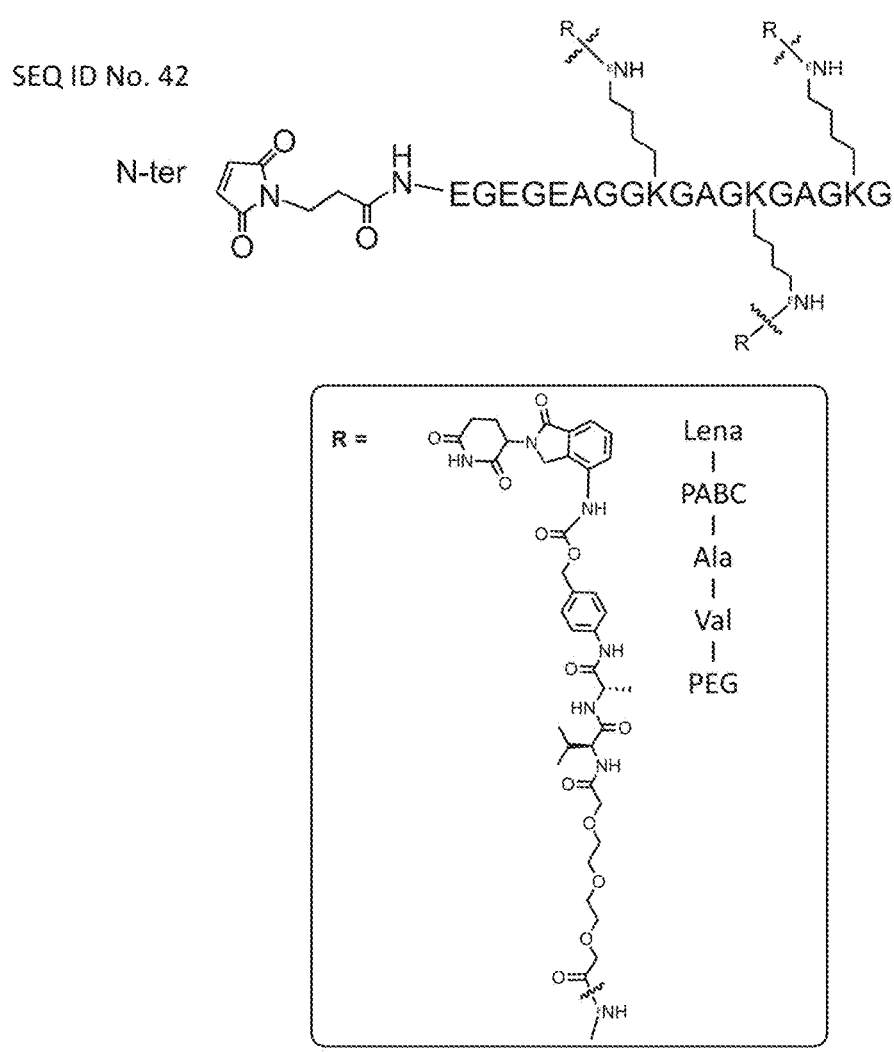
FIG. 40 is a schematic diagram showing the structure of the Mal-Peptide 3-Lenalidomide bundle according to one working example of the present invention.

FIG. 40 illustrates the structure of Mal-Peptide 3-Lenalidomide bundle, wherein the center core has the sequence of EGEGEAGGKGAGKGAGKG (SEQ ID NO: 42), where the first amino acid residue is modified with a maleimido-ethyl group. On the other hand, before being conjugated to the center core, each lenalidomide molecule is modified with a linking arm of para-amino benzyl carbamate (PABC)-alanine-valine-PEG. The lenalidomide molecule is linked to the ε-amino group of the lysine residue in the center core via the free terminus of the linking arm.

Figure 41:
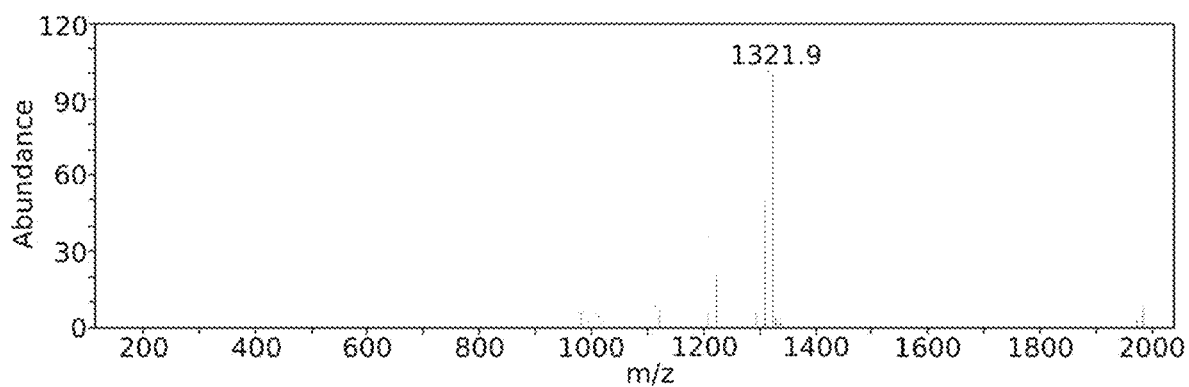
FIG. 41 shows the ESI-MS result of the Mal-Peptide 3-Lenalidomide bundle according to one working example of the present invention.

The identification of the thus-synthesized Mal-Peptide 3-Lenalidomide bundle was carried out using mass spectrometry ESI-MS. FIG. 41 shows the result of mass spectrometry ESI-MS, which indicates that the present drug bundle has a strong molecular ion at 1,321.9, which corresponds to $[M+3H]^{3+}$, indicating that the actual molecular weight of the drug bundle is 3,962.02 daltons.

Figure 42:
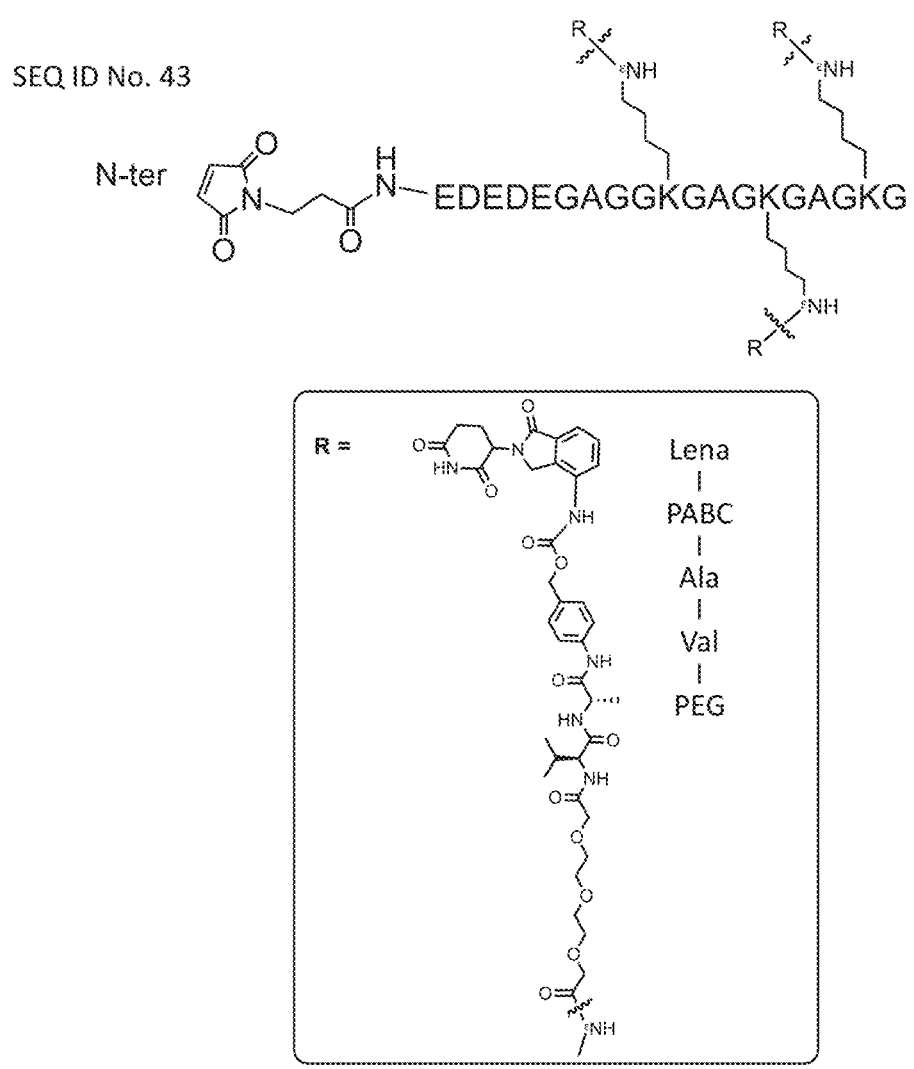
FIG. 42 is a schematic diagram showing the structure of the Mal-Peptide 4-Lenalidomide bundle according to one working example of the present invention.

FIG. 42 illustrates the structure of Mal-Peptide 4-Lenalidomide bundle, wherein the center core has the sequence of EDEDEAGGKGAGKGAGKG (SEQ ID NO: 43), where the first amino acid residue is modified with a maleimido-ethyl group. The lenalidomide molecule is modified with a linking arm as described above, and is linked to the ε-amino group of the lysine residue in the center core via the free terminus of the linking arm.

The identification of the thus-synthesized Mal-Peptide 4-Lenalidomide bundle was carried out using mass spectrometry ESI-MS. The ESI-MS result indicates that the present drug bundle has a strong molecular ion at 1,379.2, which corresponds to $[M+3H]^{3+}$, indicating that the actual molecular weight of the drug bundle is 4,135.15 daltons.

Example 41

Synthesis of Mal-Fatty Acid Bundle

In this example, a molecular construct of a Mal-Peptide 5 core and one stearoyl diacid chain and one palmitoyl acid chain was prepared.

Figure 43:
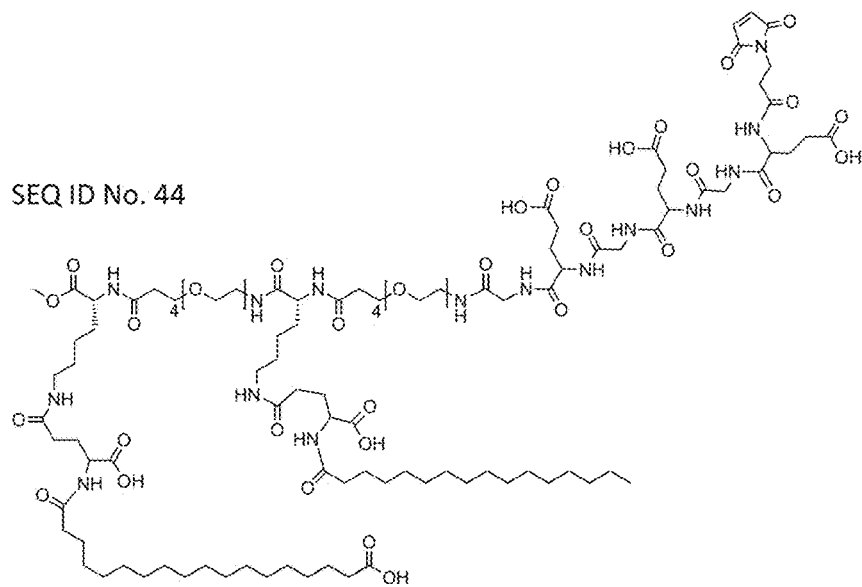
FIG. 43 is a schematic diagram showing the structure of the Mal-Peptide 5-Fatty acid bundle according to one working example of the present invention.

FIG. 43 illustrates the structure of this Mal-Peptide 5-Fatty acid bundle, wherein the center core has the sequence of maleimido-ethyl-EGEGE-$X_1$-K-$X_2$-K-OMe (SEQ ID NO: 44), where the first amino acid residue is modified with a maleimido-ethyl group, the last lysine residue is modified with a methoxy group (-OMe), and both the $X_1$ and $X_2$ are PEGylated amino acids with 4 EG repeats. One stearoyl diacid chain and one palmitoyl acid chain were respectively linked to the K residues of the peptide center core by forming an amide bond between the $CO_2H$ group of the fatty acid and the amine group of the K residue. The structure of the present Mal-Peptide 5-Fatty acid bundle was designed by the present inventors, and the synthesis was outsourced to Shanghai WuXi AppTech Co., Ltd. (Shanghai, China). The Mal-Peptide 5-Fatty acid bundle product has a purity of greater than 97.0%.

Figure 44:
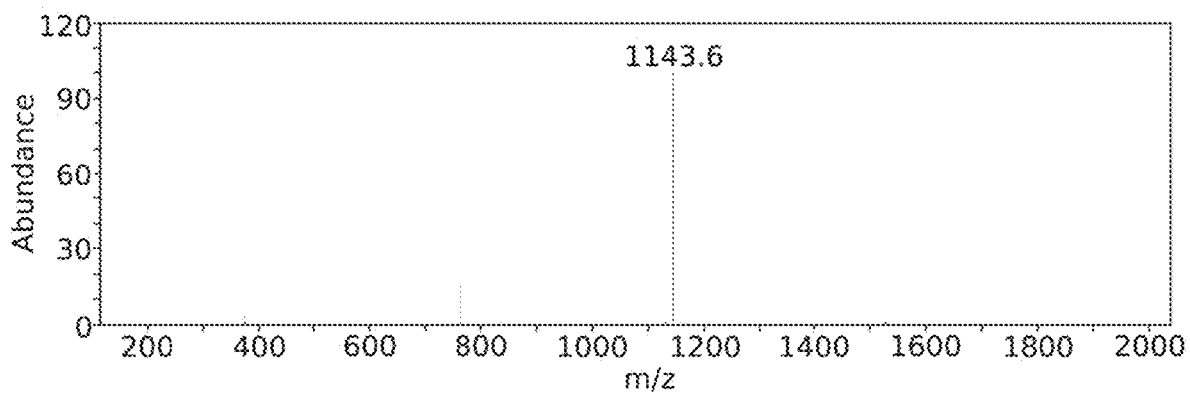
FIG. 44 shows the ESI-MS result of the Mal-Peptide 5-Fatty acid bundle according to one working example of the present invention.

The identification of the synthesized Fatty acid bundle was carried out using mass spectrometry ESI-MS. The ESI-MS result in FIG. 44 indicates that the present molecular construct has a strong molecular ion at 1,143.6, which corresponds to $[M+2H]^{2+}$, indicating that the actual molecular weight of the Mal-Peptide 5-Fatty acid bundle is 2,285.66 daltons.

Example 42

Synthesis of 3-DOTA Arm Linker Unit

Figure 45:
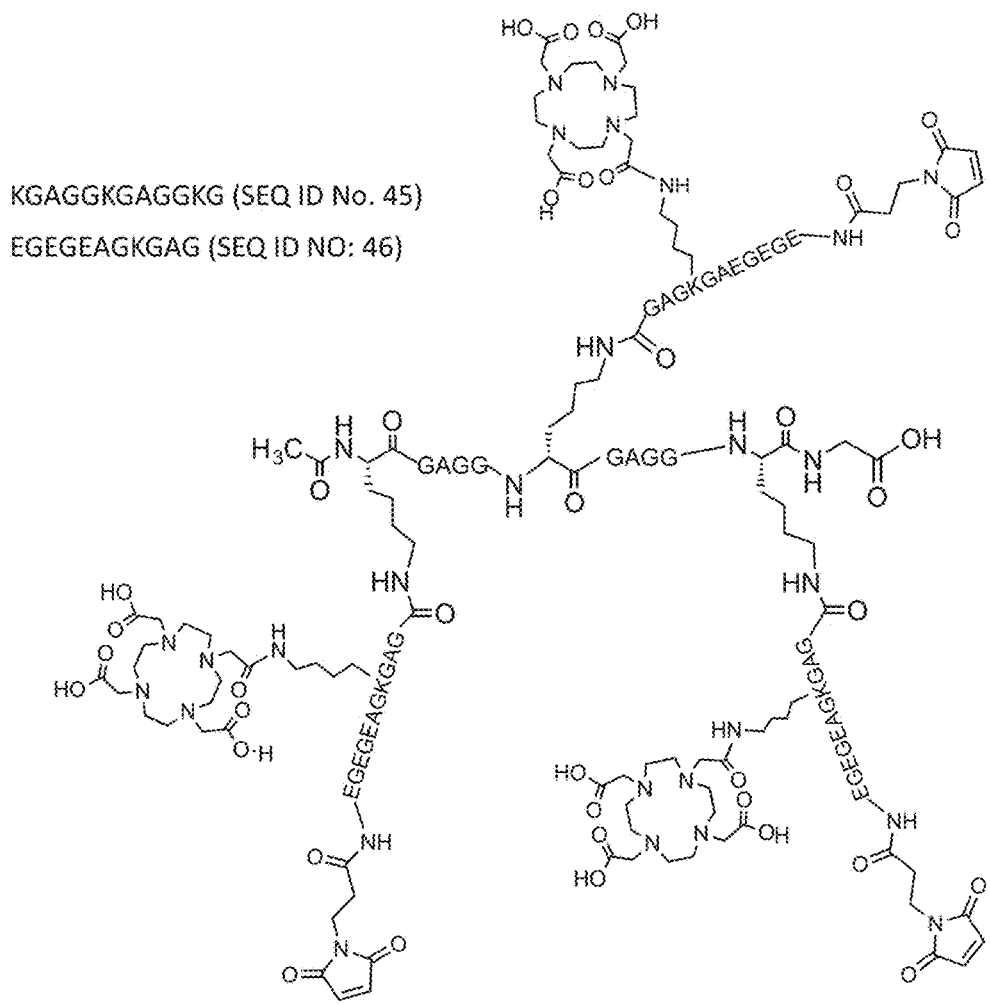
FIG. 45 is a schematic diagram showing the structure of the 3-DOTA arm linker unit according to one working example of the present invention.

In this example, a 3-DOTA arm linker unit for carrying three peptides was prepared. FIG. 45 illustrates the structure of this 3-arm linker. In particular, the linker unit comprise a center core having the sequence of acetyl-KGAGGK-GAGGKG (SEQ ID NO: 45, Peptide core 6), wherein the first lysine residue is modified with an acetyl group. The linker unit also comprises three peptide linking arms having the sequence of maleimido-ethyl-EGEGEAGKGAG (SEQ ID NO: 46), wherein the first glutamate residue is modified with a maleimido-ethyl group and the lysine residue is modified with a DOTA molecule.

Figure 46:
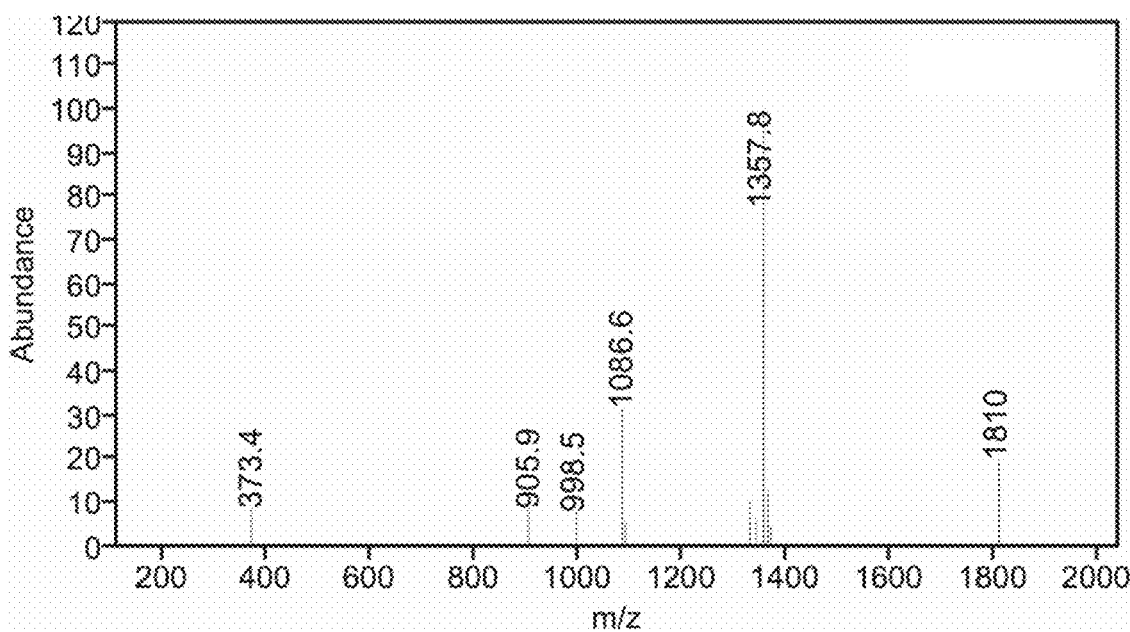
FIG. 46 shows the ESI-MS result of the 3-DOTA arm linker unit according to one working example of the present invention.

The structure of the present 3-DOTA arm linker unit was designed by the present inventors, and the synthesis was outsourced to Shanghai WuXi AppTech Co., Ltd. (Shanghai, China). The identification of the 3-DOTA arm linker unit was carried out using mass spectrometry ESI-MS. The ESI-MS result in FIG. 46 indicates that the present molecular construct has a strong molecular ion at 1,357.8, which corresponds to [M+4H]4+, indicating that the actual molecular weight of the 3-DOTA arm linker unit was 5,427.2 daltons.

Example 43

Construction, Expression and Purification of Recombinant MBM-1-IL-2

In this example, a composite protein having the sequence described in SEQ ID NO: 47 was constructed, expressed and purified using the protocols similar to those set forth in the preceding working examples. In particular, the present MBM-1-IL-2 molecular construct has an MBM-1 motif, followed by a short flexible linker of SEQ ID NO: 9 and the IL-2 sequence.

Culture supernatants were harvested and the expressed recombinant fusion proteins in the media were purified using anion exchange column. Prior to purification, the recombinant MBM-1-IL-2 fusion protein was adjusted to pH 8.5. Then, the protein was applied to pre-equilibrated (50 mM Bis-Tris buffer at pH 8.5) Q sepharose anion exchange resin (GE Healthcare). The MBM-1-IL-2 fusion protein was eluted using a 3-step elution of with 200 mM, 500 mM and 1M NaCl in 4M urea solution at pH 8.5, respectively.

Figure 47:
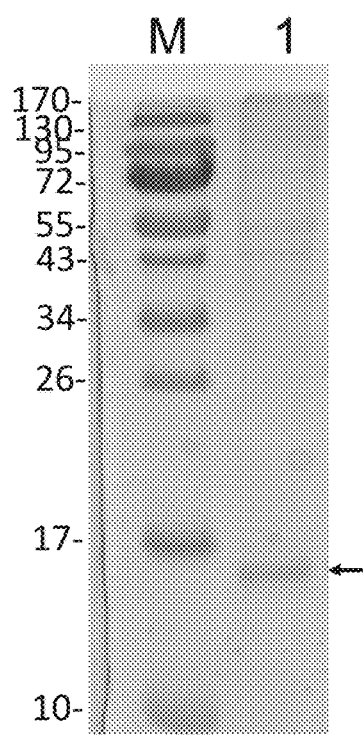
FIG. 47 shows the SDS-PAGE analysis of the MBM-1-IL-2 according to one working example of the present invention.

The eluted samples were analyzed using 10% SDS-PAGE shown in FIG. 47. The MBM-1-IL-2 fusion protein was revealed as the major band at about 16 kDa, which is consistent with the expected size (indicated by an arrow).

Example 44

Synthesis of 2-Chain (scFv α CD38)-Fc-MBM-1×2 Lenalidomide Bundles

In this Example, the (scFv α CD38)-Fc-MBM-1 fusion protein from Example 10 and the Mal-Peptide 4-Lenalidomide bundle from Example 40 were conjugated to produce a molecular construct having 2-chain (scFv α CD38)-Fc-MBM-1 fusion protein and 2 Lenalidomide bundles conjugated to the respective cysteine residue of the metal binding motifs of the fusion protein. Briefly, the purified (scFv α CD38)-Fc-MBM-1 fusion protein was prepared in sodium succinate buffer (30 mM sodium succinate, pH5.3, 0.02% tween 20, and 100 mM sucrose) and reduced by incubating with 45 PM TCEP at room temperature for 30 minutes with gentle shaking. After the reduction reaction, the excess TCEP was removed by dialysis against 10 mM sodium succinate buffer (pH5.3, 0.02% tween 20, and 100 mM sucrose) containing 60 μM Zn (II) ions. Then, the reduced protein samples were treated with 15 μM Mal-Peptide 4-Lenalidomide bundle and then incubated for 1 hour at room temperature. The non-reacted Lenalidomide bundles were removed using a desalting column and the product was analyzed using SDS-PAGE.

Figure 48:
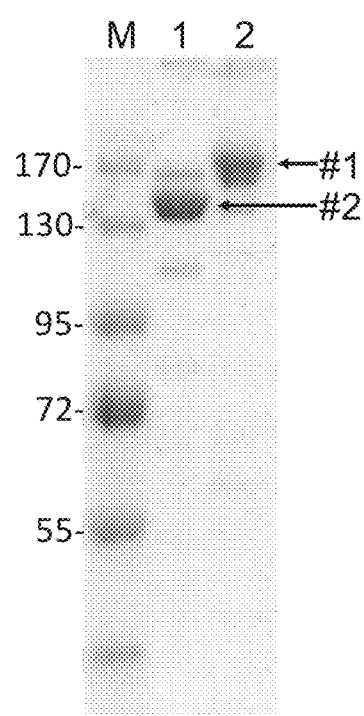
FIG. 48 shows the SDS-PAGE analysis of the 2-chain (scFv α CD38)-Fc-MBM-1×2 Lenalidomide bundles according to one working example of the present invention.

FIG. 48 shows the result of the SDS-PAGE analysis of the present molecular construct. As indicated in FIG. 48, this molecular construct has a molecular weight of about 120 kDa (indicated by an arrow #1 in the lane 2), which is somewhat larger than the expected size. The non-conjugated molecular construct was in lane 3 (indicated by an arrow #2). As shown in FIG. 48, the yield of the conjugation of 2-chain (scFv α CD38)-Fc-MBM-1 with Lenalidomide bundles is approximately 85%.

Example 45

Synthesis of Octreotide×Fatty Acid Bundle

Figure 49:
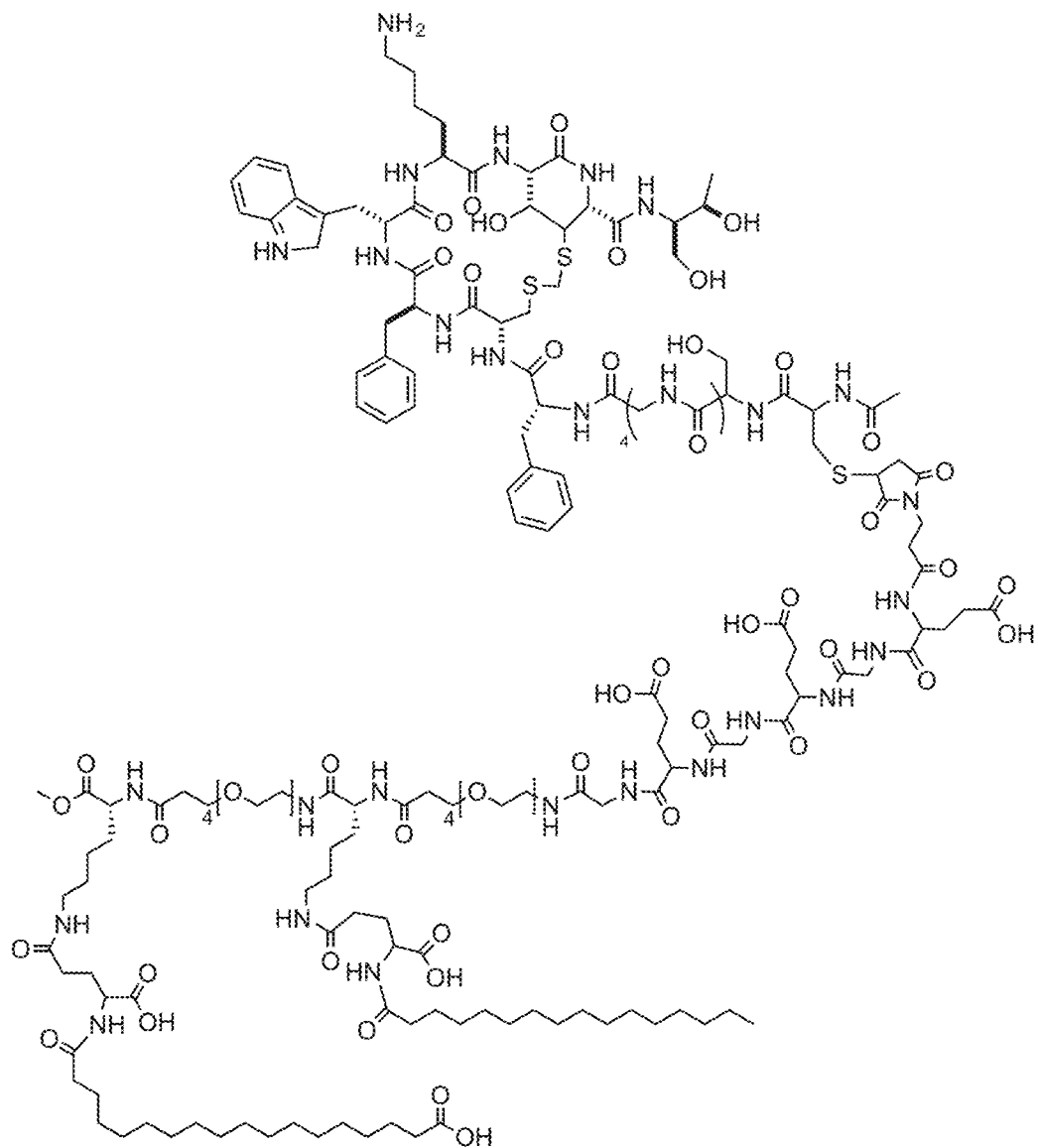
FIG. 49 is a schematic diagram showing the structure of the Octreotide×Fatty acid bundle according to one working example of the present invention.

In this Example, the Mal-Peptide 5-Fatty acid bundle from Example 41 and Cys-octreotide from Example 35 were conjugated using protocols similar to those set forth above, so that the maleimido group of the Mal-Peptide 5-Fatty acid bundle is conjugated with the —SH group of the terminal cysteine residue of the Cys-octreotide, thereby producing a molecular construct of Octreotide×Fatty acid bundle (see, FIG. 49).

Example 46

Synthesis of Aib-GLP-1 Agonist×Fatty Acid Bundle

Figure 50A:
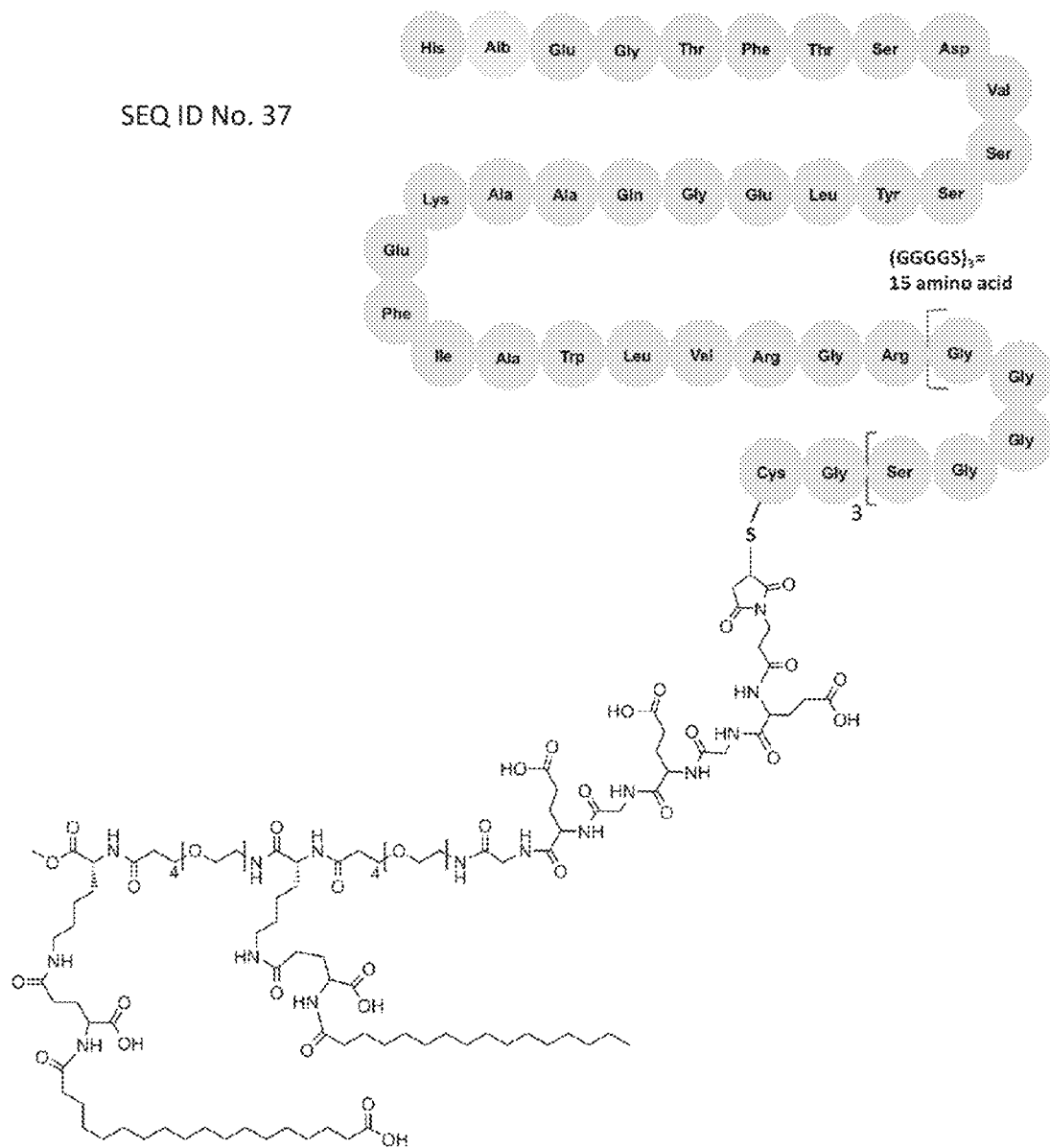
FIG. 50A is a schematic diagram showing the structure of the Aib-GLP-1 agonist×Fatty acid bundle according to one working example of the present invention.

In this Example, the Mal-Peptide 5-Fatty acid bundle from Example 41 and Aib-GLP-1 agonist-Cys from Example 34 were conjugated using protocols similar to those set forth above, so that the maleimido group of the Mal-Peptide 5-Fatty acid bundle is conjugated with the —SH group of the terminal cysteine residue of the Aib-GLP-1 agonist-Cys, thereby producing a molecular construct of Aib-GLP-1 agonist×Fatty acid bundle (see, FIG. 50A).

Example 47

Synthesis of Teriparatide-MBM-1×Fatty Acid Bundle

Figure 50B:
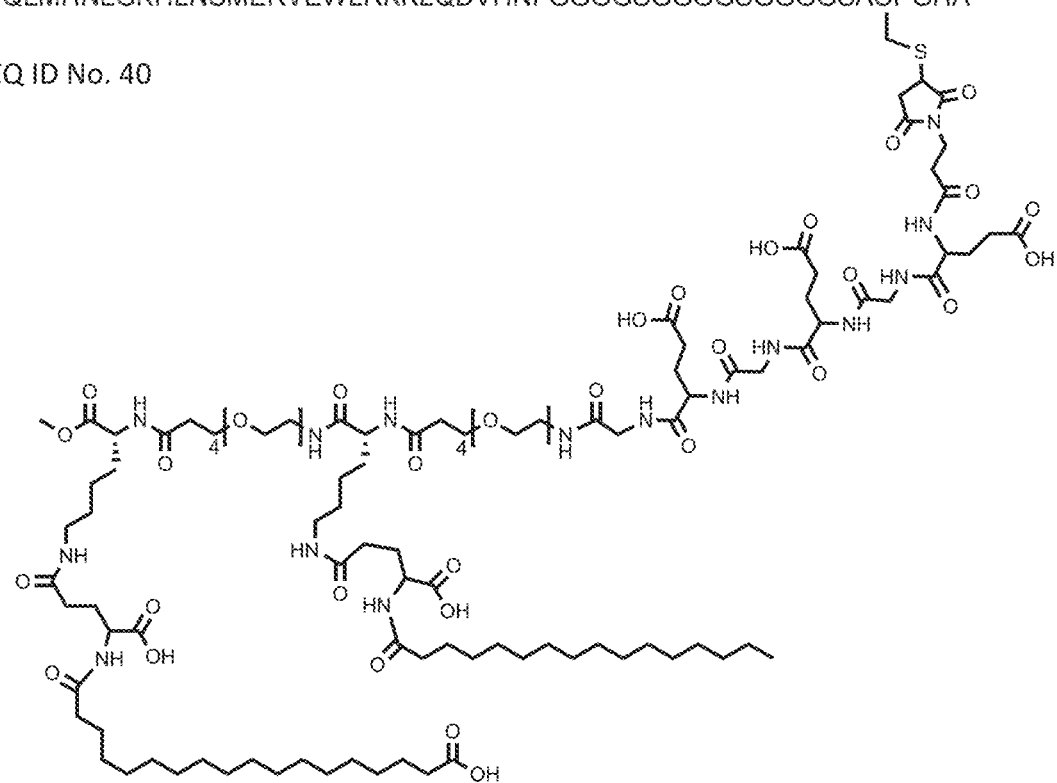
FIG. 50B is a schematic diagram showing the structure of the Teriparatide-MBM-1×Fatty acid bundle according to one working example of the present invention.

In this Example, the Mal-Peptide 5-Fatty acid bundle from Example 41 and teriparatide-MBM-1 from Example 38 were conjugated using protocols similar to those set forth above to produce a molecular construct of Teriparatide-MBM-1×Fatty acid bundle (see, FIG. 50B).

Example 48

Synthesis of Leuprolide-MBM-3×Fatty Acid Bundle

Figure 51A:
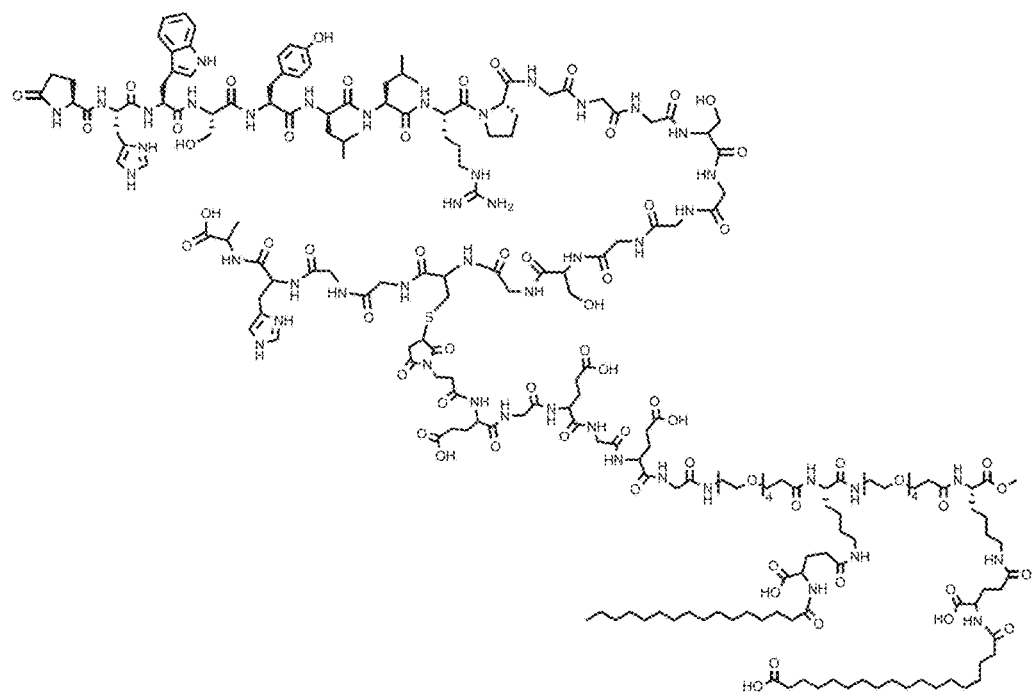
FIG. 51A is a schematic diagram showing the structure of the Leuprolide-MBM-3×Fatty acid bundle according to one working example of the present invention.
Figure 51B:
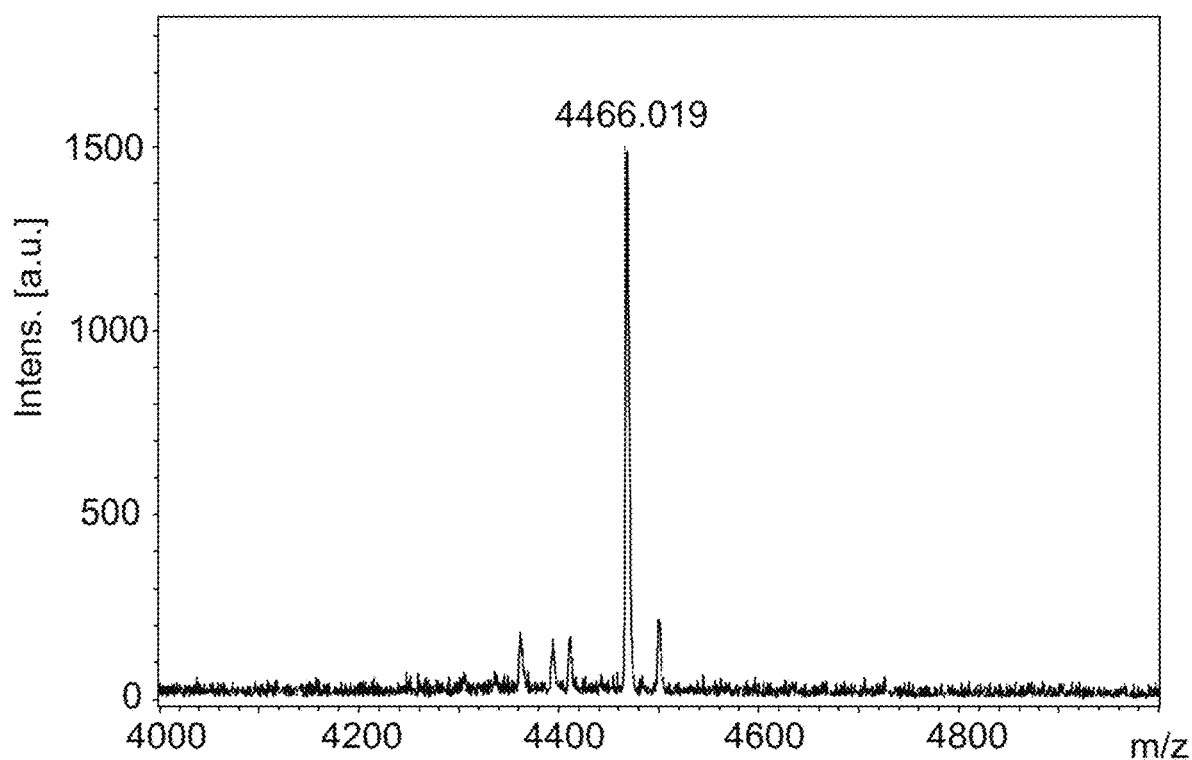
FIG. 51B shows the MALDI-TOF result Leuprolide-MBM-3×Fatty acid bundle according to one working example of the present invention.

In this Example, the Mal-Peptide 5-Fatty acid bundle from Example 41 and Leuprolide-MBM-3 from Example 39 were conjugated using protocols similar to those set forth above to produce a molecular construct of Leuprolide-MBM-3×Fatty acid bundle (see, FIG. 51A). The identification of the synthesized Leuprolide-MBM-3×Fatty acid bundle was carried out using mass spectrometry MALDI-TOF, and the result in FIG. 51B indicates that this molecular construct has a molecular weight of 4,466.019 daltons. The molecular weight of 2,181.038 daltons showed an excess of Leuprolide-MBM-3 molecule at a molar ratio of 1.5:1 [leuprolide-MBM-3:Mal-Peptide 5-fatty acid] of this reaction.

Example 49

Synthesis of 3-DOTA Arm Linker Unit×3 PSMA Ligands

Figure 52A:
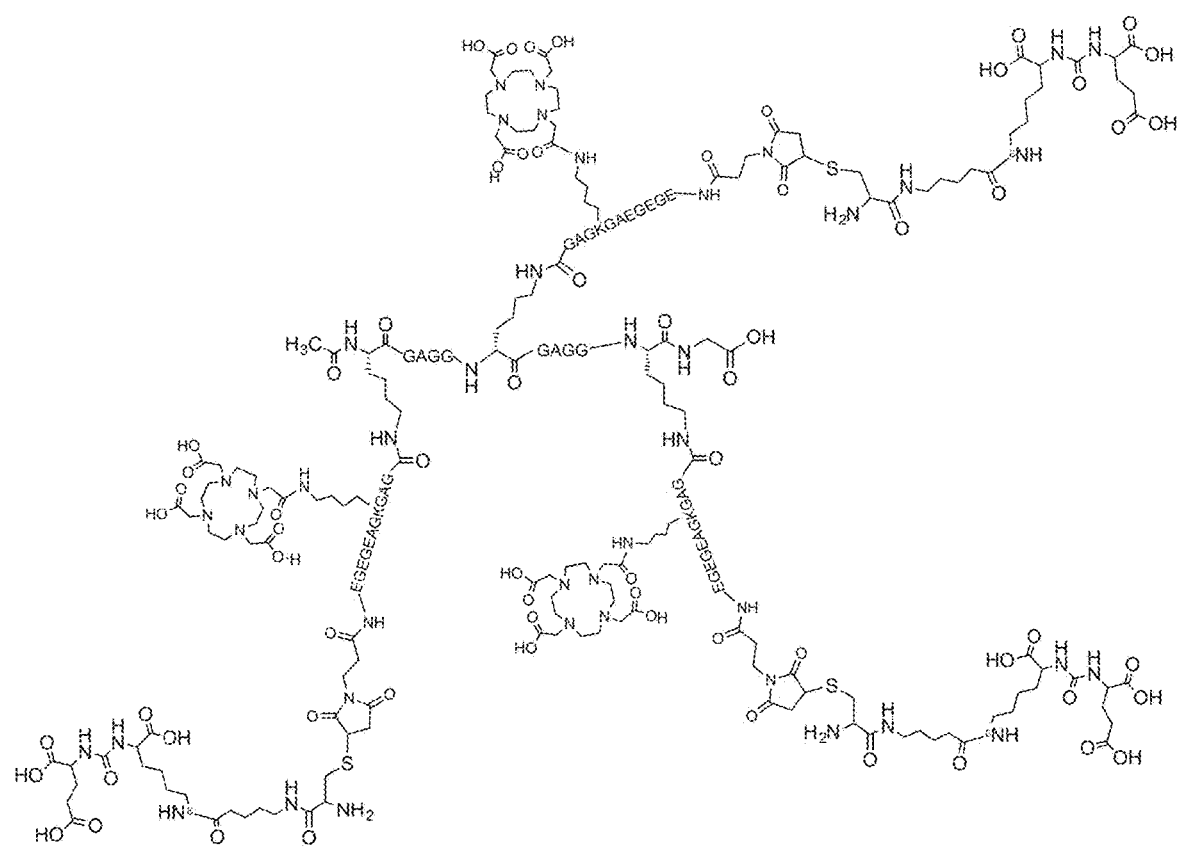
FIG. 52A is a schematic diagram showing the structure of the 3-DOTA arm linker unit×3 PSMA ligands according to one working example of the present invention.
Figure 52B:
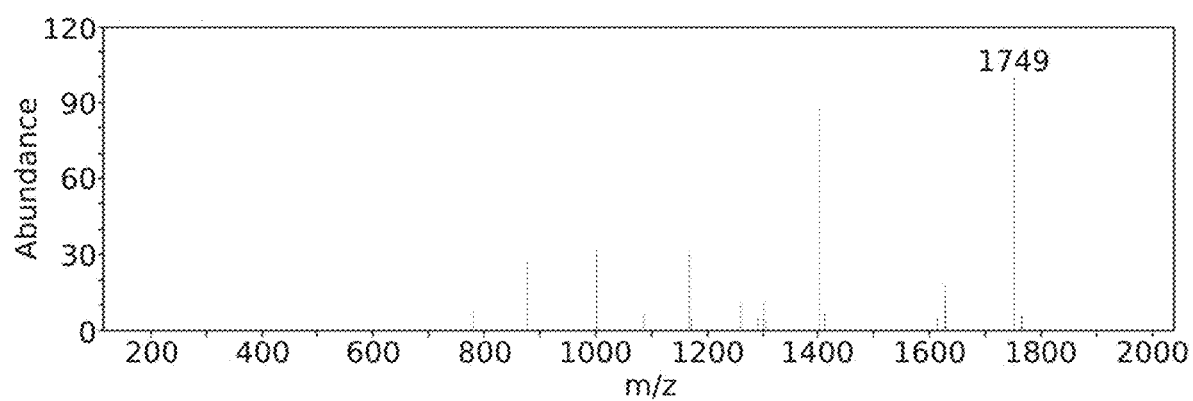
FIG. 52B shows the ESI-MS result of the 3-DOTA arm linker unit×3 PSMA ligands according to one working example of the present invention.

In this Example, the 3-DOTA arm linker unit from Example 42 and three Cys-PSMA ligands from Example 36 were conjugated using protocols similar to those set forth above to produce a molecular construct of 3-DOTA arm linker unit×3 PSMA ligands (FIG. 52A). The identification of the synthesized 3-DOTA arm linker unit×3 PSMA ligands was carried out using mass spectrometry ESI-MS, and the result in FIG. 52B indicates that this molecular construct has a strong molecular ion at 1,749, which corresponds to $[M+4H]^4$, indicating that the actual molecular weight of the 3-DOTA arm linker unit×3 PSMA ligands is 6,992.18 daltons.

Example 50

Purification of Stabilized 2-Chain (scFv α CA19-9)-Fc-MBM-1×2 DOTA Bundles

The procedure to stabilize the recombinant 2-chain (scFv α CA19-9)-Fc-MBM-1×2 DOTA bundles was performed as described in the preceding Examples.

The 2-chain fusion protein conjugated with two DOTA bundles of the preceding examples was adjusted to pH 5.0 and then applied to pre-equilibrated (0.1 mM EDTA, 50 mM Bis-Tris at pH 5.0) Anion exchange column Q sepharose (GE Healthcare). The sample was then eluted using 3-step elution; a first elution of 320 mM NaCl for 70 minutes, followed by a second elution of 330 mM for 100 minutes, and then a final elution of 1,000 mM NaCl for 50 minutes with a flow rate of 1.0 ml/min.

The 2-chain (scFv α CA19-9)-Fc-MBM-1×2 DOTA bundles was separated from the free 2-chain (scFv α CA19-9)-Fc-MBM-1 fusion protein, the 2-chain (scFv α CA19-9)-Fc-MBM-1 conjugated with three or four DOTA bundles, and aggregated material using the anion exchange column Q sepharose.

Figure 53:
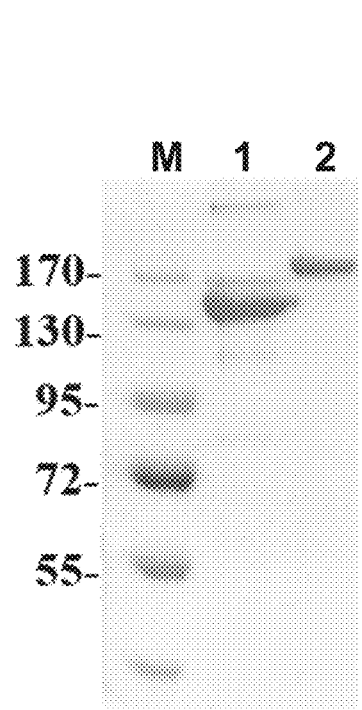
FIG. 53 shows the SDS-PAGE analysis of the purified 2-chain (scFv α CA19-9)-Fc-MBM-1×2 DOTA bundles according to one working example of the present invention.

The purified product, the 2-chain (scFv α CA19-9)-Fc-MBM-1×2 DOTA bundles, was collected. Lane 1 and lane 2 shown in FIG. 53 respectively correspond to non-conjugated molecular construct and the molecular construct conjugated with two DOTA bundles.

Example 51

Purification of Stabilized 2-Chain (scFv α CD38)-Fc-MBM-1×2 Lenalidomide Bundles The molecular construct of 2-chain (scFv α CD38)-Fc-MBM-1×2 Lenalidomide bundles from Example 44 was stabilized using the protocols similar to those set forth in the preceding Examples.

The stabilized molecular construct of 2-chain (scFv α CD38)-Fc-MBM-1×2 Lenalidomide bundles was adjusted to pH 7.0 and then applied to pre-equilibrated (50 mM $Na_2HPO_4$ at pH 7.0, 1M NaCl) hydrophobic interaction column (HIC) Phenyl HP (GE Healthcare). The stabilized molecular construct was eluted using a linear gradient from 1000 mM to 0 mM NaCl in the flow rate of 1.0 ml/min for 80 minutes.

Figure 54:
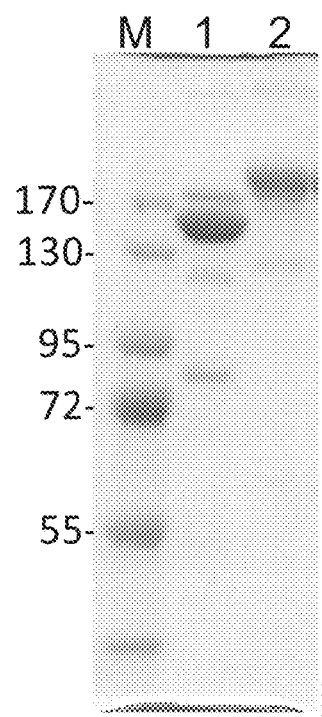
FIG. 54 shows the SDS-PAGE analysis of the purified 2-chain (scFv α CD38)-Fc-MBM-1×2 Lenalidomide bundles according to one working example of the present invention.

The collected samples of the preceding HIC purification were applied to a size exclusion chromatography column ENrich™ SEC650 (Bio-Rad) to separate the stabilized molecular construct from aggregated material. The purified product was collected. Lane 1 and lane 2 of 10% non-reducing SDS-PAGE shown in FIG. 54 respectively correspond to non-conjugated molecular construct and molecular construct conjugated with two lenalidomide bundles.

Figure 55:
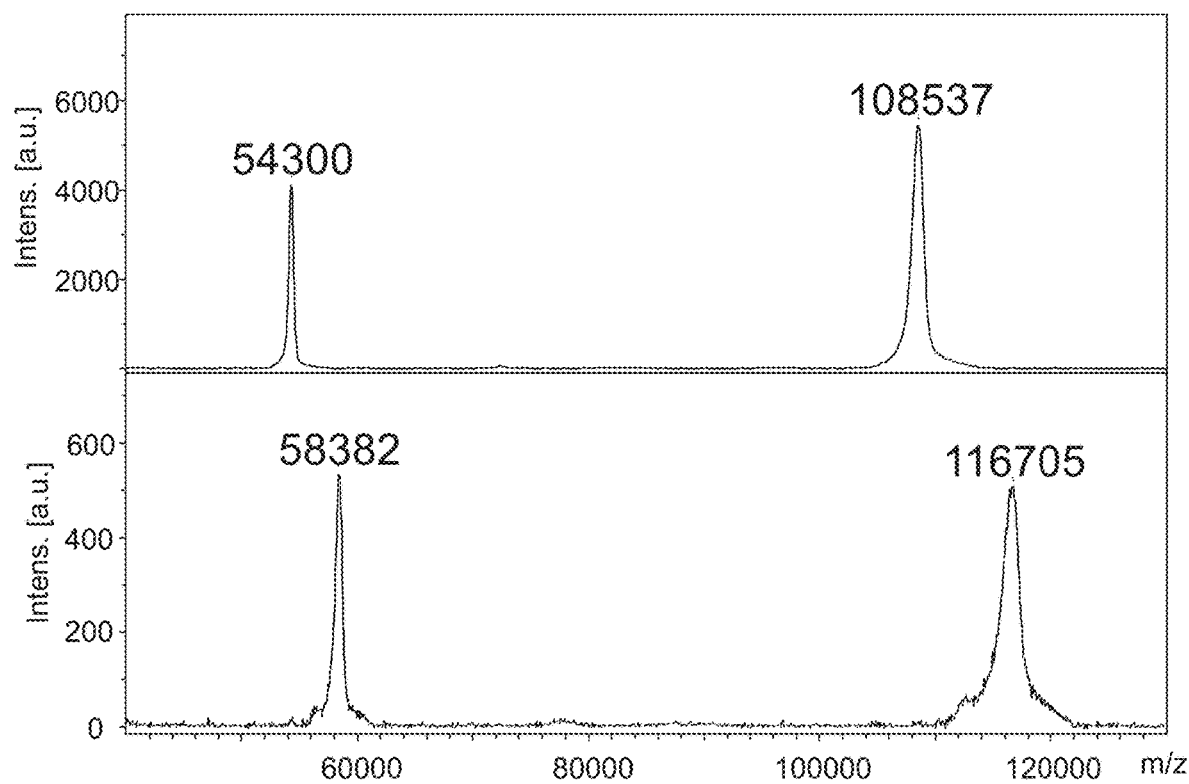
FIG. 55 shows the MALDI-TOF result of the purified 2-chain (scFv α CD38)-Fc-MBM-1×2 Lenalidomide bundles according to one working example of the present invention.

The purified stabilized molecular construct of 2-chain (scFv α CD38)-Fc-MBM-1×2 Lenalidomide bundles was further analyzed using mass spectroscopy MALDI-TOF. Mass spectrometric analysis result in the lower scheme of FIG. 55 shows that the sample has a molecular weight of 58,382 and 116,705 daltons, which correspond to m/z (z=1): $[M+H]^+$ and m/z (z=2): $[M+2H]^{2+}$, respectively.

Mass spectrometric analysis result of the 2-chain (scFv α CD38)-Fc-MBM-1 as a control shown in the upper scheme of FIG. 55 indicates that the sample has a molecular weight of 54,300 and 108,537 daltons, which correspond to m/z (z=1): $[M+H]^+$ and m/z (z=2): $[M+2H]^2$, respectively.

Example 52

Half-Life of Stabilized 2-Chain (scFv α CD38)-Fc-MBM-1×2 Lenalidomide Bundles in NOD-SCID Mice The measurement of half-lives of the stabilized 2-chain (scFv α CD38)-Fc-MBM-1×2 Lenalidomide Bundles was carried out in mice after i.v. administration. The molecular construct in the serum sample was observed using ELISA method. 8 to 10-week-old NOD-SCID mice are purchased from BioLasco, Taipei, Taiwan. Mice were grouped into three mice per group, and were injected intravenously via intravenous bolus with 100 μl of 7.6 μM molecules.

Figure 56A:
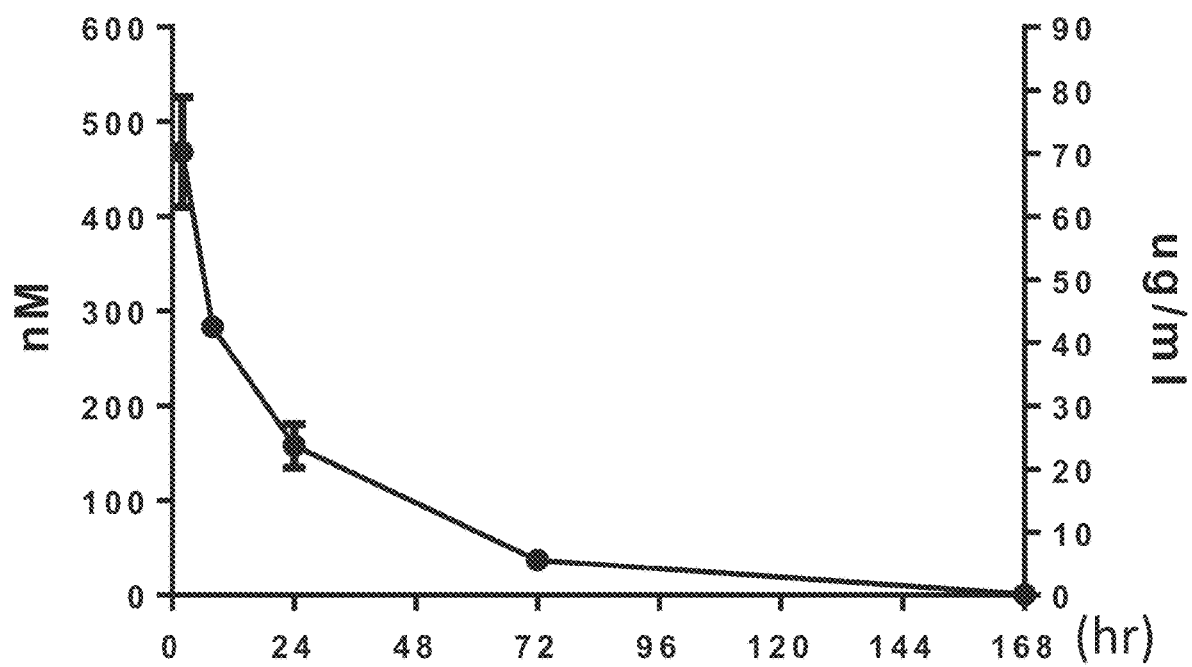
FIG. 56A and FIG. 56B show the half-lives of parental anti-CD38 hIgG1.Fc antibody and the 2-chain (scFv α CD38)-Fc-MBM-1×2 Lenalidomide bundles according to one working example of the present invention.
Figure 56B:
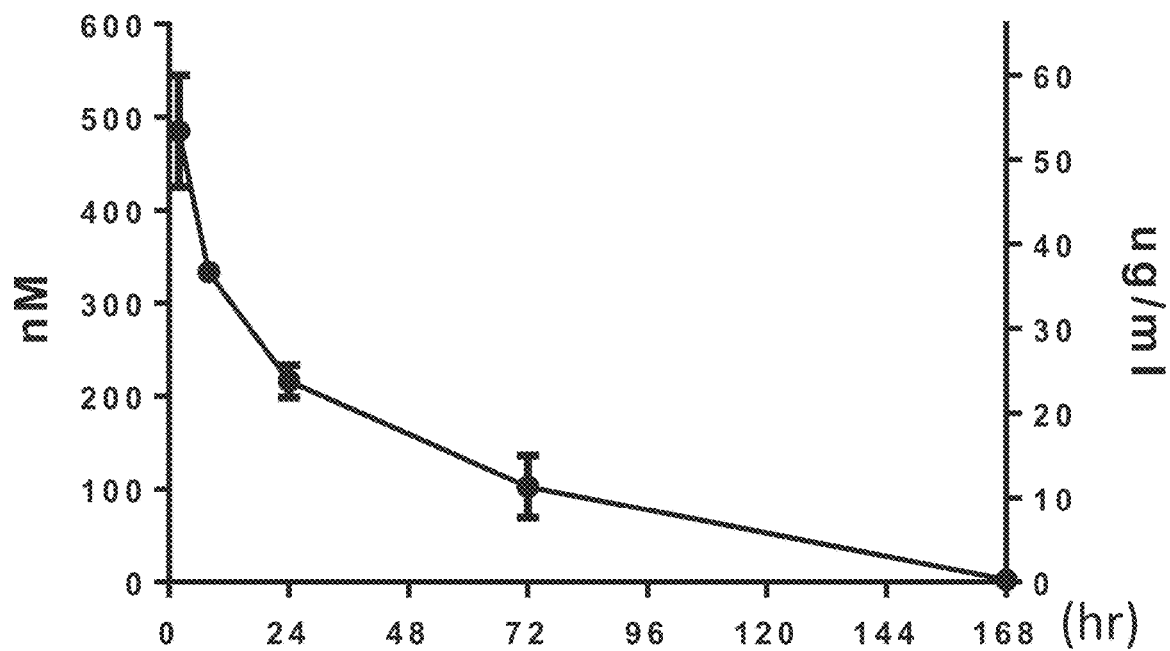

The results indicate that the half-lives of the parental anti-CD38 hIgG1.Fc antibody (FIG. 56A) and 2-chain (scFv α CD38)-Fc-MBM-1×2 Lenalidomide bundles (FIG. 56B) are about 13.1 and 23.9 hours, respectively. The results of using non-compartment pharmacokinetic model show that the present 2-chain (scFv α CD38)-Fc-MBM-1×2 Lenalidomide bundles has a longer half-life than that of the conventional anti-CD38 antibody.

Example 53

Cytotoxic Activities of Purified 2-Chain (scFv α CD38)-Fc-MBM-1×2 Lenalidomide Bundles to H929 and CD38-Positive U266 Cells H929 cells ($5\times10^3$/well) were added into wells of 96-well plates in RPMI1640 medium containing 10% fecal bovine serum. After 2 hours, cells were treated with different concentrations (2-fold dilutions from 20 μM) of the purified the 2-chain (scFv α CD38)-Fc-MBM-1 (without Lenalidomide bundle) and the 2-chain (scFv α CD38)-Fc-MBM-1×2 Lenalidomide bundles. After being incubated for 2 hours, the culture medium was removed by centrifuging at 400 g for 5 minutes and replaced with a fresh medium, and the cells were further incubated for another 120 hours (5 days) and 168 hours (7 days). Cell viability was then determined using the alamarBlue cell viability reagent kit (Invitrogen) in accordance with the manufacturer's instruction.

The protocols for determining cytotoxic activities of purified the 2-chain (scFv α CD38)-Fc-MBM-1 with or without 2 Lenalidomide bundles on CD38-positive U266 were similar to those described above with respect to H929 cells.

Figure 57A:
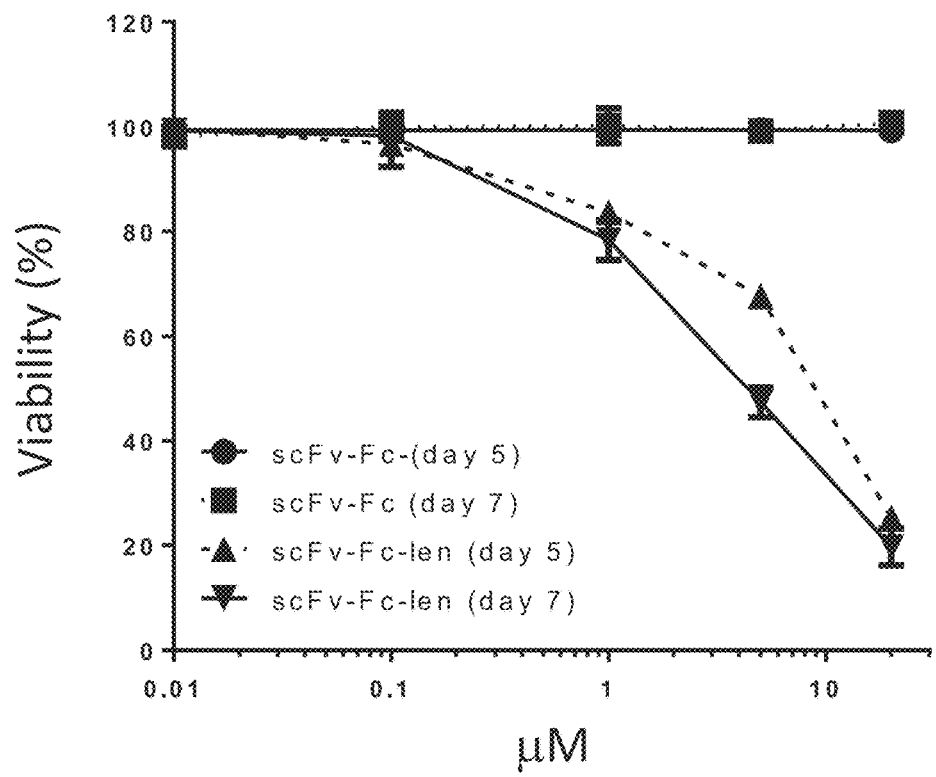
FIG. 57A to FIG. 57C show the targeting effect of the 2-chain (scFv α CD38)-Fc-MBM-1×2 Lenalidomide bundles according to one working example of the present invention.

FIG. 57A shows the viability of H929 cells of the four treatments groups. The 2-chain (scFv α CD38)-Fc-MBM-1×2 Lenalidomide bundles (labeled as "scFv-Fc-len") caused approximately 80% of cytolysis of H929 cells at 20 μM after incubation for 5 days. The 2-chain (scFv α CD38)-Fc-MBM-1 (labeled as "scFv-Fc"), which was used as a negative control, showed no cytotoxic effect.

Figure 57B:
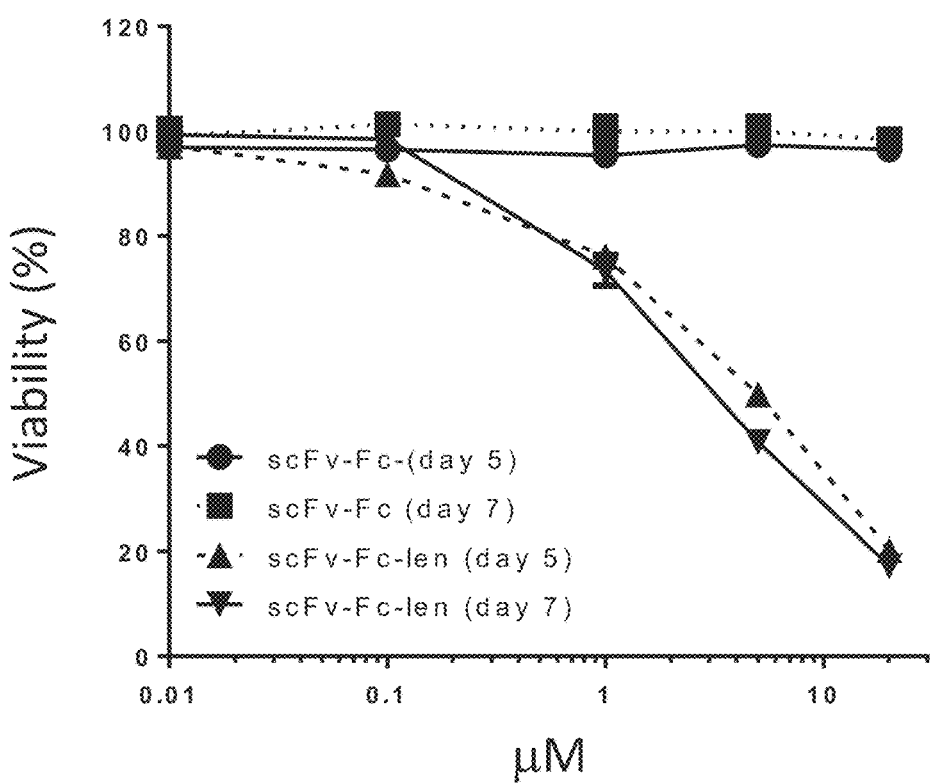

FIG. 57B shows the viability of CD38-positive U266 cells of the four treatments groups. The 2-chain (scFv α CD38)-Fc-MBM-1×2 Lenalidomide bundles caused approximately 80% of cytolysis of CD38-positive U266 cells at 20 μM after incubation for 5 days.

Figure 57C:
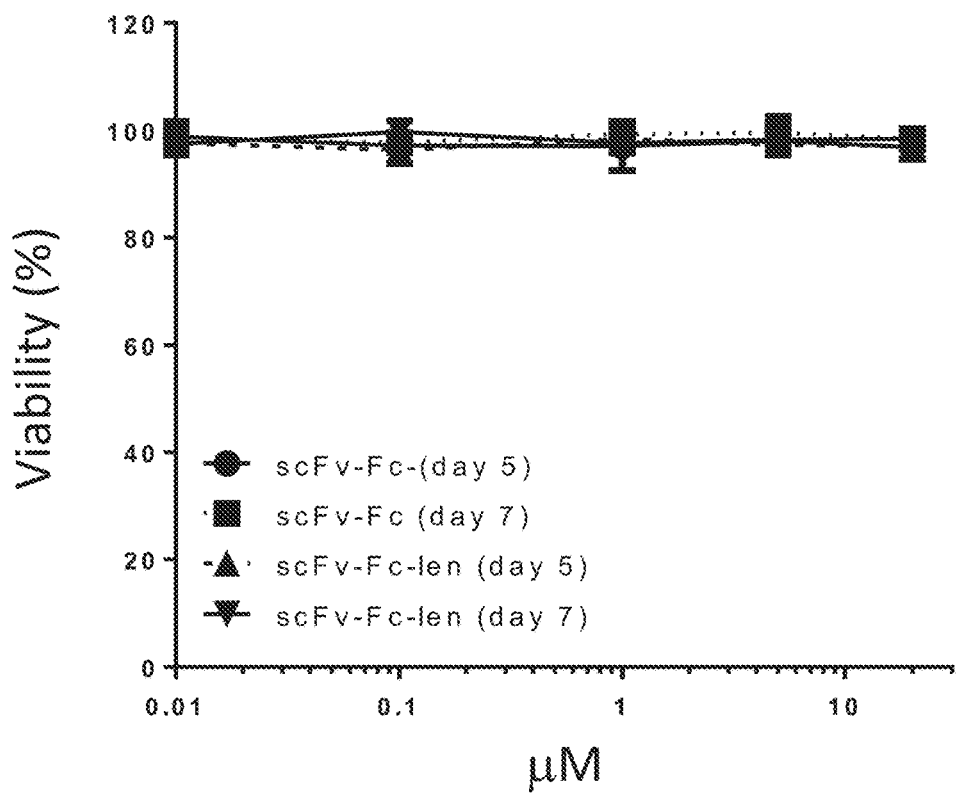

FIG. 57C shows the viability of CD38-negative U266 cells of the four treatments groups. The 2-chain (scFv α CD38)-Fc-MBM-1×2 Lenalidomide bundles (labeled as "scFv-Fc-len") can not cause any cytolysis of CD38-negative U266 cells at each molar concentration.

In sum, the results in FIG. 57A to 57C indicated that the 2-chain (scFv α CD38)-Fc-MBM-1×2 Lenalidomide bundles has a strong effect of targeting.

Example 54

Antibody-Dependent Cell-Mediated Cytotoxicity (ADCC) of Purified 2-Chain (scFv α CD38)-Fc-MBM-1×2 Lenalidomide Bundles on CD38-Expressing H929 and U266 Cells In this example, in vitro analysis was carried out to investigate the antibody-dependent cell-mediated cytotoxicity (ADCC) effect of the 2-chain (scFv α CD38)-Fc-MBM-1×2 Lenalidomide bundles on the cell lysis of CD38-expressing H929 and CD38-positive U266 cells.

Human total peripheral blood mononuclear cell (PBMC) was isolated from donors to examine the ADCC function. H929 cells or CD38-positive U266 cells were incubated with the 2-chain (scFv α CD38)-Fc-MBM-1×2 Lenalidomide bundles at a final concentration of 200, 40, 8, 1.6, 0.32, or 0.064 nM, and then mixed with human PBMC at an E:T ratio of 25 and incubated at 37° C. for 5 hours. The parental anti-CD38 mAb was used as a positive control. Cytolysis was analyzed using an LDH Cytotoxicity Assay Kit (Enzo Life Sciences).

Figure 58A:
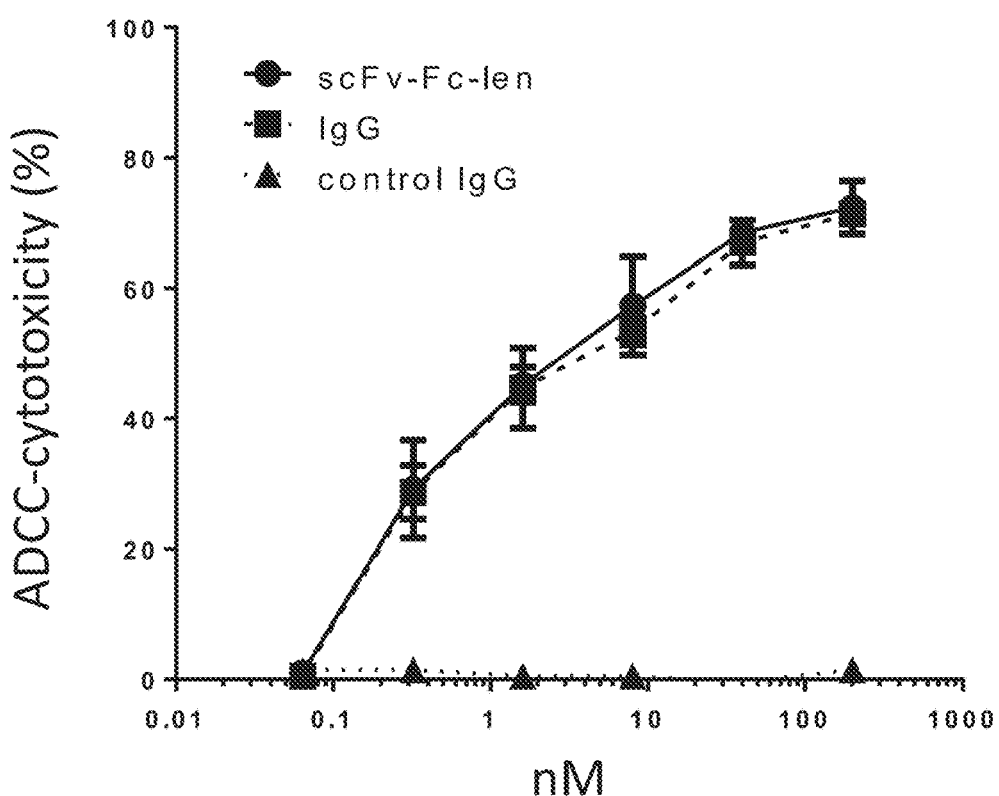
FIG. 58A and FIG. 58B show the ADCC effect of the 2-chain (scFv α CD38)-Fc-MBM-1×2 Lenalidomide bundles according to one working example of the present invention.

The data shown here indicate that the purified 2-chain (scFv α CD38)-Fc-MBM-1×2 Lenalidomide bundles (labeled as "scFv-Fc-len") recruited effector cells in a way similarly to its parental anti-CD38 mAb to manifest the cytolytic activity (FIG. 58A). The parental anti-CD38 antibody was used as a positive control (labeled as "IgG"), and an isotype control antibody (labeled as "control IgG") was also used.

Figure 58B:
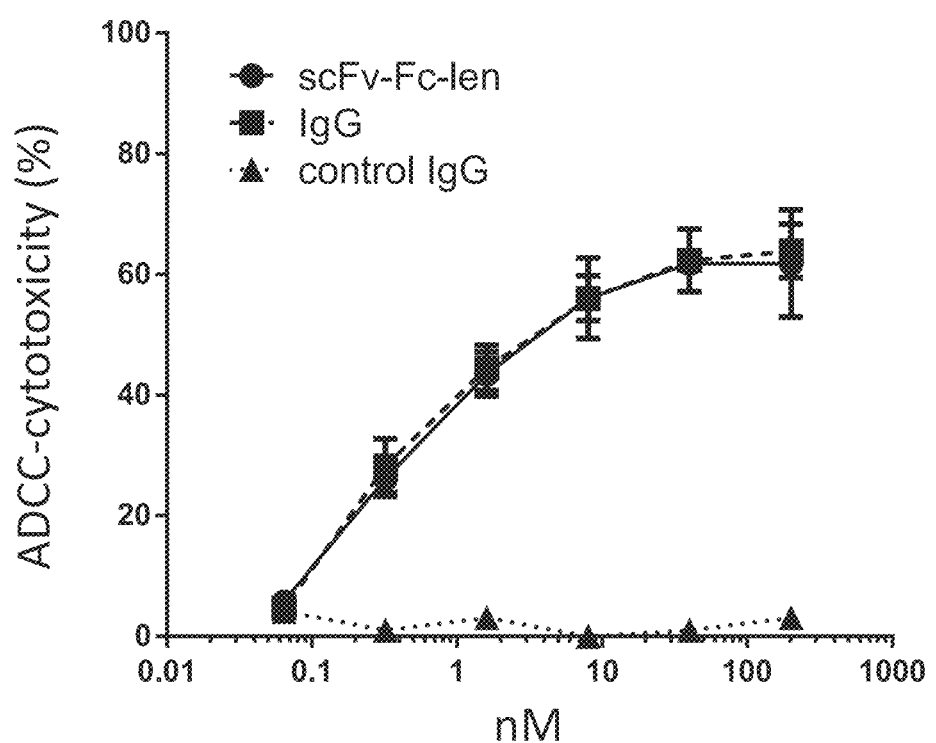

FIG. 58B shows that the purified 2-chain (scFv α CD38)-Fc-MBM-1×2 Lenalidomide bundles (labeled as "scFv-Fc-len") also manifest the cytolytic activity to CD38-positive U266 cells in a way similar to its parental counterpart.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A composite polypeptide, comprising a parent polypeptide and a metal binding motif, wherein the metal binding motif comprises the amino acid sequence of $CX_1X_2HA$ (SEQ ID NO: 1) in the order from N-terminus to C-terminus, where $X_1$ is glycine or proline, and $X_2$ is glycine or alanine, and the metal binding motif is located at the N- or C-terminus of the parent polypeptide, wherein the parent polypeptide is a peptide hormone, receptor-binding peptidomimetic ligand, antibody, antibody fragment or cytokine.

2. The composite polypeptide according to claim 1, wherein the amino acid sequence of the metal binding motif is CGGHA (SEQ ID NO: 2), CPGHA (SEQ ID NO: 3), CGAHA (SEQ ID NO: 4), CPAHA (SEQ ID NO: 5), GCGGHA (SEQ ID NO: 6), ACPGHA (SEQ ID NO: 7), and or GCPGHA (SEQ ID NO: 8).

3. A molecular construct, comprising a composite polypeptide according to claim 1 and a functional element, wherein the functional element has a sulfhydryl (SH)-reactive group, which is conjugated to the thiol group of the cysteine residue in the metal binding motif.

4. The molecular construct according to claim 3, wherein the SH-reactive group is maleimide, iodoacetyl, bromoacetyl, vinyl sulfone, mono-sulfone, methyl sulfonyl benzothiazole, or 2-pyridyldithiol group.

5. The molecular construct according to claim 3, wherein the composite polypeptide is in a dimer form, each having one functional element conjugated thereto.

6. The molecular construct according to claim 3, wherein the functional element comprises,
   a center core, wherein the center core comprises,
      2 to 10 lysine (K) residues,
      optionally, one or more fillers, wherein any two of the K residues are adjacent to each other or are separated by the filler,
      optionally, a terminal spacer, wherein the terminal spacers is an N-terminal spacer linked to the N-terminus of the first K residue or a C-terminal spacer linked to the C-terminus of the last K residue, and each of the filler and the terminal spacer comprises, independently, (1) 1 to 12 non-K amino acid residues, or (2) a PEGylated amino acid having 1 to 12 repeats of ethylene glycol (EG) unit, and
      the SH-reactive group, linked to the first or last K residue of the center core by forming an amide bond therewith, or when the terminal spacer is present, the SH-reactive group is linked to the terminal amino acid residue of the terminal spacer by forming an amide bond therewith; and
   2 to 10 targeting, effector or pharmacokinetic elements, wherein,
      each targeting, effector or pharmacokinetic element is linked to the K residue of the core, or
      when the molecular construct further comprises 2 to 10 linking arms, one terminus of each linking arm is linked to the K residue of the core via forming an amide bond with the ϵ-amino group of the K residue, and the other terminus of each linking arm is linked to each targeting, effector or pharmacokinetic element, wherein the linking arm is a peptide comprising 2-12 non-K amino acid residues; or a polyethylene glycol (PEG) chain having 2-24 repeats of EG units.

7. The molecular construct according to claim 6, wherein the center core carries a local negative charge at or near the amino acid residue linked with the SH-reactive group.

8. The molecular construct according to claim 7, wherein the center core has at least one glutamate (E) residue or aspartate (D) residue at or near the amino acid residue linked with the SH-reactive group.

9. The molecular construct according to claim 7, wherein the local negative charge is present in the first 5 to 15 amino acid residues starting from the amino acid residue linked with the SH-reactive group.

10. The molecular construct according to claim 7, wherein the effector elements are negatively charged chemical moieties.

11. The molecular construct according to claim 7, wherein the pharmacokinetic element is a $C_{8-28}$ fatty acid derivative or $C_{8-28}$ dioic fatty acid derivative, wherein the ϵ-amino group of the K residue is linked with the $C_{8-28}$ fatty acid derivative or $C_{8-28}$ dioic fatty acid derivative.

* * * * *